United States Patent [19]

Katz

[11] Patent Number: 6,024,746
[45] Date of Patent: Feb. 15, 2000

[54] METHOD AND APPARATUS FOR LOCATING BONE CUTS AT THE DISTAL CONDYLAR FEMUR REGION TO RECEIVE A FEMORAL PROTHESIS AND TO COORDINATE TIBIAL AND PATELLAR RESECTION AND REPLACEMENT WITH FEMORAL RESECTION AND REPLACEMENT

[75] Inventor: Lawrence Katz, Upper Saddle River, N.J.

[73] Assignee: Lawrence Katz, Monsey, N.Y.

[21] Appl. No.: 09/049,781

[22] Filed: Mar. 27, 1998

Related U.S. Application Data

[63] Continuation-in-part of application No. 08/956,015, Oct. 22, 1997, which is a continuation-in-part of application No. 08/455,985, May 31, 1995, Pat. No. 5,776,137.

[51] Int. Cl.[7] .................................................. A61B 17/58
[52] U.S. Cl. ............................... 606/88; 606/87; 606/102
[58] Field of Search .................................. 606/88, 87, 102

[56] References Cited

U.S. PATENT DOCUMENTS

| | | |
|---|---|---|
| 4,950,298 | 8/1990 | Gustilo et al. . |
| 5,047,058 | 9/1991 | Roberts et al. . |
| 5,053,037 | 10/1991 | Lackey . |
| 5,100,408 | 3/1992 | Lackey . |
| 5,234,433 | 8/1993 | Bert et al. . |
| 5,282,803 | 2/1994 | Lackey . |
| 5,354,075 | 10/1994 | Marik et al. . |
| 5,364,401 | 11/1994 | Ferrante et al. . |
| 5,417,694 | 5/1995 | Marik et al. . |
| 5,454,816 | 10/1995 | Ashby . |
| 5,484,446 | 1/1996 | Burke et al. . |
| 5,486,178 | 1/1996 | Hodge . |
| 5,514,140 | 5/1996 | Lackey . |
| 5,549,688 | 8/1996 | Ries et al. . |
| 5,578,039 | 11/1996 | Vendrely et al. ......................... 606/88 |
| 5,681,316 | 10/1997 | DeOrio et al. ............................ 606/88 |

OTHER PUBLICATIONS

Genesis II Total Knee System Primary Surgical Technique.
Smith & Nephew Richards, The Profix Total Knee System.

*Primary Examiner*—Gary Jackson
*Assistant Examiner*—Julian W. Woo
*Attorney, Agent, or Firm*—Ostrolenk, Faber, Gerb & Soffen, LLP

[57] ABSTRACT

An apparatus and method of using same to form planar resections on the medial and lateral condyles of a femur and a corresponding resection of a tibia in a knee includes a caliper feeler and measurement plate to measure for the size of the femoral prosthesis to be received and a tibial resection guide. The caliper feeler and measurement plate are used to determine a first distance between an anterior surface of the femoral cortex and a plane tangent to a posterior surface of the medial and lateral condyles of a femur. A graduated scale between the caliper feeler and the measurement plate compares the first distance to at least two standard femoral prosthesis sizes so that the most suitable size can be selected, and measures a second distance between the first distance and the size of the selected standard femoral prosthesis size to determine a thickness or thickness to be resected at the posterior surface of the femoral condyles. The tibial resection guide includes a pair of styli which slide and rotate in the resection guide to contact the proximal tibial surface. The styli include incremental markings to properly place the guide for resection.

55 Claims, 44 Drawing Sheets

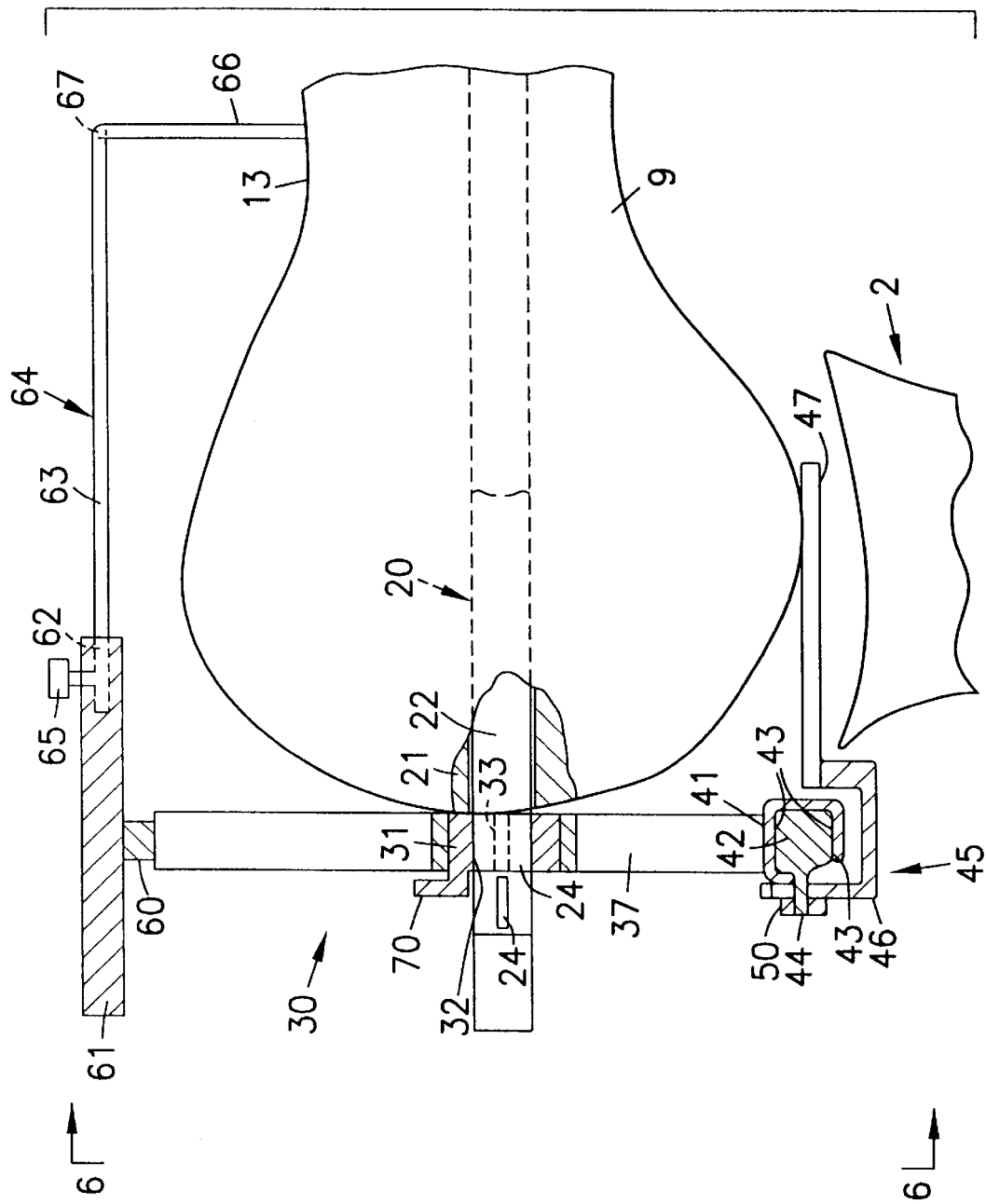

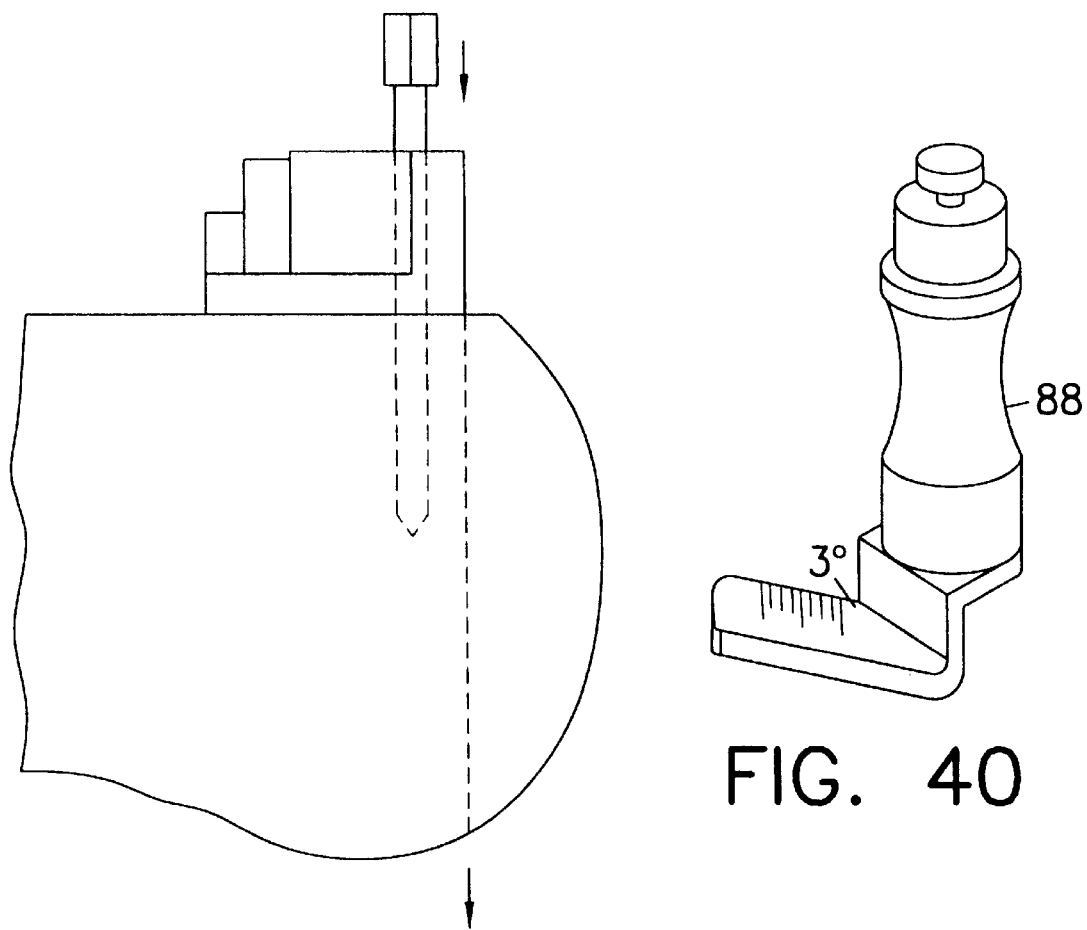
FIG. 39
FIG. 40
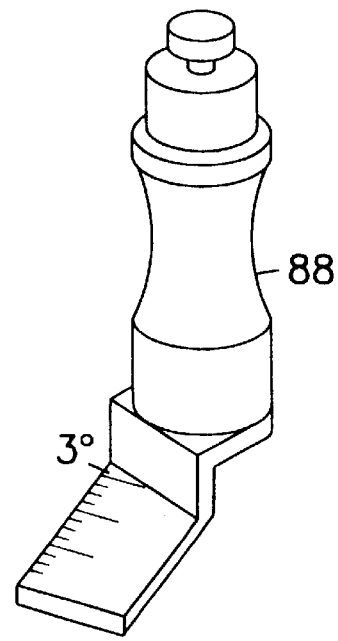
FIG. 41

FIG. 46B
FIG. 46
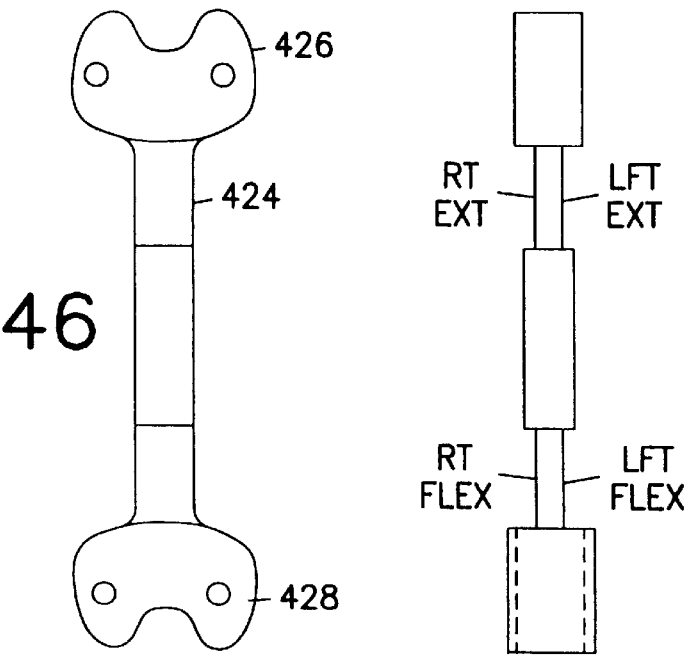
FIG. 47
FIG. 46A
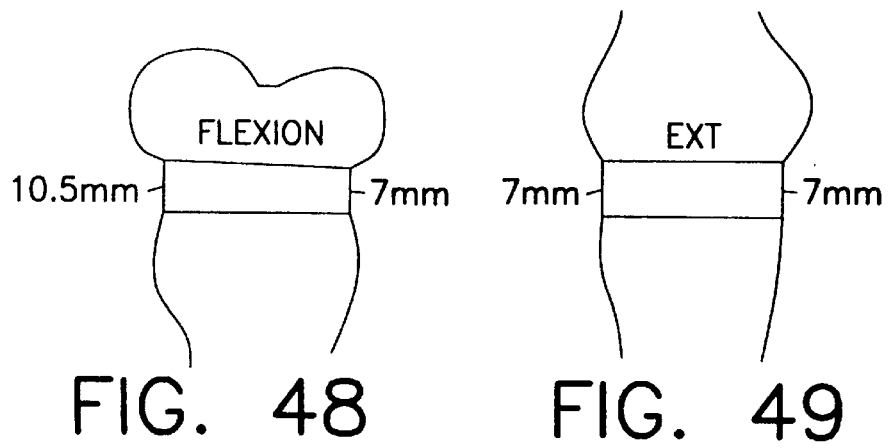
FIG. 48
FIG. 49 ic FEMUR REGION TO RECEIVE A FEMORAL
PROTHESIS AND TO COORDINATE TIBIAL
AND PATELLAR RESECTION AND
REPLACEMENT WITH FEMORAL
RESECTION AND REPLACEMENT

CROSS-REFERENCE TO RELATED APPLICATIONS

This application is a continuation-in-part application to U.S. patent application Ser. No. 08/956,015, filed Oct. 22, 1997 entitled METHOD AND APPARATUS FOR LOCATING BONE CUTS AT THE DISTAL CONDYLAR FEMUR REGION TO RECEIVE A FEMORAL PROTHESIS AND PROPERLY ARTICULATED WITH PATELLAR AND TIBIAL PROTHESIS, now pending, which is a continuation-in-part application to U.S. patent application Ser. No. 08/455,985, filed May 31, 1995, entitled METHOD AND APPARATUS FOR LOCATING BONE CUTS AT THE DISTAL CONDYLAR FEMUR REGION TO RECEIVE A FEMORAL PROSTHESIS, now U.S. Pat. No. 5,776,137, both disclosures of which are incorporated by reference herein.

FIELD OF THE INVENTION

The invention relates to methods and apparatus for locating bone cuts on the medial and lateral femoral condyles to form seating surfaces for a femoral knee prosthesis, and to coordinate tibial and patellar resection and replacement with femoral resection and replacement.

The invention further relates to a tool for locating said cuts.

BACKGROUND OF THE INVENTION

Over the years, the concepts of designs for the total knee arthroplasty have evolved to the point where with few exceptions, most are quite comparable in the design of femoral, tibial and patellar prostheses.

Major discrepancies and problems encountered are caused by physician error and failure to understand the principles of more complex alignment or ligament problems to be corrected at surgery. With the more complex alignment or "routine" degenerative knee, the major differences are the ease and consistency of instrumentation for alignment and proper bone cuts allowing proper ligament balance. This allows satisfactory motion and stability post operatively.

The distal femoral cuts must be placed to provide the knee prosthesis with a proper flexion and extension gap, proper varus-valgus alignment, proper patellofemoral relationship and proper rotation. It is customary to use an intramedullary rod placed in a retrograde fashion between the medial and lateral femoral condyles just anterior to the intercondylar notch to establish a single point of reference for subsequent bone cuts. A major problem is in the instrumentation to indicate the location of the femoral cuts which relies upon the "experience" or "eyeballing" of the surgeon. Over the years, two basic instrument system designs have become popular.

In one design (anterior referencing), the total knee alignment system takes its point of reference from a centrally placed rod and careful attention is given to the patellofemoral joint by using an anteriorly placed feeler gage. The distal femoral cut is consistent with the thickness of the prosthesis.

This instrument system operates on the principle of anatomic anterior and distal femoral cuts to allow proper ligament balancing and stability in extension as well as consistent patellofemoral placement on the anterior surface. The femur is not notched, and the anterior surface of the femoral prosthesis not elevated above the anterior surface of the femur. Notching the femur may cause a decrease in strength of the distal femur. Elevation of the anterior surface of the prosthesis will cause extremely high patellofemoral pressures in a joint that seems to be prone to a high rate of post-operative failure.

By establishing the anterior femoral cut as the benchmark or datum starting point, however, the anterior referencing instruments result in the installation of a knee prosthesis which sacrifices consistent stability in flexion due to the formation of a posterior femoral condylar cut that may leave the posterior space either too wide or too narrow. This can cause instability in flexion, or restrict flexion and cause increased wear.

The second type of instrument design (posterior referencing) is based on the concept that the flexion and extension stability are more important and the patellofemoral joint is of secondary importance. This system also uses an intramedullary rod for referencing. Although I consider all three joints as "important", when a compromise must be made, the posterior referencing systems compromise the patellofemoral joint while the anterior reference systems sacrifice stability in flexion (the posterior tibial femoral joint). Both systems allegedly equally address the distal tibial-femoral space. Neither consistently addresses the distal rotation of the femoral component.

Neither system tries to preserve the joint line at or near an "anatomic" level. By elevating the jointline, the patella is distalized. The femur is also shortened. Since the arthritic knee often has a loss of cartilage, there may be a patella infera of 2–3 mm initially. Elevating the distal femoral resection beyond this will:

1) Further alter the patellofemoral relationship.
2) Change the isometric and rotational balance of the MCL and the LCL.
3) Shorten the femur in flexion and may cause increased roll back, anterior lift off, and increased posteromedial wear.
4) Elevate the level of tibial resection necessitating a major amount of posterior femoral resection to achieve a satisfactory flexion space.

When performing a unicompartmental knee replacement, it is imperative to maintain the jointline. As a consequence, it is desirable to maintain a full range of motion.

SUMMARY OF THE INVENTION

An object of the invention is to provide methods and apparatus for locating bone cuts on the medial and lateral femoral condyles to form seating surfaces for a femoral knee prosthesis, and to coordinate tibial and patellar resection and replacement with femoral resection and replacement which reliably and anatomically provide:

1. Consistent distal tibio-femoral stability.
2. Consistent distal femoral rotation.
3. Consistent placement of the anterior cut flush with the anterior surface of the femoral cortex, i.e., without notching or elevation.
4. Consistent placement of the posterior femoral cut such that the distal and posterior cuts are equal (when indicated) allowing for satisfactory extension and flexion stability and motion.

The method and apparatus of the invention contemplate placement of the anatomic joint line which, in extreme cases, vary up to the difference between the anterior-posterior A-P internal measurements of the size prostheses. Based on my knowledge of total knee replacement, personal experience with numerous routine total knee replacements, numerous more complicated cases consisting of knees with flexion deformities and revision surgery, a maximum of a few mm proximal displacement of the joint line is considerably less harmful than:

1. A lax flexion gap;
2. Sloping the proximal tibial cut to accommodate for an inconsistent posterior femoral condylar cut;
3. Significantly notching the femur anteriorly;
4. Raising the anterior flanges of the prosthesis and thus the patellofemoral joint;
5. Not allowing full extension;
6. Raising the joint line;
7. Tightness in flexion;
8. Malrotation; and
9. Patient pain.

With an understanding of the measurements involved in total knee replacement, a new instrument system and methodology has been developed to allow flexion 120–130 degrees; to perform less soft tissue releasing; and decrease surgical time. Starting with a "normal" knee, the goal should be to maintain the anatomic landmarks as close to normal as possible. Then, if deformities are present, the procedure can be modified to accommodate the situation.

In accordance with the invention, a method is provided for forming planar cuts on the medial and lateral condyles of the femur to form seating surfaces to receive a femoral knee prosthesis, comprising:

determining a prospective planar cut at the posterior of the condyles of the femur at which the distance between the anterior surface of the femoral cortex and the prospective planar cuts is substantially equal to the interior dimension of a knee prosthesis to be fitted on said femur at the anterior surface and the cut planar surface, determining the thickness of the posterior lateral or medial condyle which will be resected by said prospective planar cut, cutting the distal ends of the condyles along a plane at which the maximum thickness of resection of the more prominent condyle at said distal end is substantially equal to the thickness determined to be resected at the posterior medial or lateral condyle by said prospective planar cut, and cutting the condyles along a plane substantially flush with the anterior surface of the femoral cortex, and along said prospective planar cut.

The method further contemplates loosely placing a longitudinal intramedullary rod in the femur such that an end of the rod projects from the femur, mounting a tool on the projecting end of the rod, establishing, by said tool, an angular position of said prospective planar cut along a plane rotated at an angle of between 0 and 15" with respect to a tangential plane at the posterior of the lateral and medial condyles about an axis located in said tangential plane.

In further accordance with the method, the tool is rotated with said rod through said angle and a datum or benchmark is established by the rotated rod or by pins installed in the condyles on the basis of the rotated position of the tool. A cutting guide can be mounted on said tool, to enable the distal end of the condyles to be cut along said plane. Thereafter, the tool is removed and a second A-P cutting guide is mounted on the selected benchmark, i.e., the rod or the pins and the posterior and anterior cuts are made. The axis about which the plane of the prospective cut is rotated is located in said tangential plane at the posterior surfaces of the medial and lateral condyles and can be located at either of the condyles or at any location therebetween. It is a feature of the invention that the tool remains on the rod both for the measurements and for the cutting of the distal end of the femur.

The invention also contemplates that the cutting guide supports a means which enables the cutting guide to be secured to the condyles during the cutting of the distal ends of the condyles.

The invention further contemplates an apparatus for forming planar resections on the medial and lateral condyles of a femur to form seating surfaces to receive a femoral prosthesis and to properly articulate with a tibial and patellar prosthesis comprising:

a caliper feeler and measurement plate to measure for the size of the femoral prosthesis to be received, said caliper feeler and measurement plate adapted to determine a first distance between an anterior surface of the femoral cortex and a plane tangent to a posterior surface of the medial and lateral condyles of a femur, the caliper feeler referencing the anterior surface of the femoral cortex and the measurement plate referencing the plane tangent to the posterior surface of the medial and lateral condyles;

a graduated scale to compare the first distance to at least two standard femoral prosthesis sizes and to determine the smaller of the at least two standard femoral prosthesis sizes;

a graduated scale to measure a second distance between the first distance and the size of the smaller standard femoral prosthesis size, so that a thickness or thicknesses can be measured to be resected at the posterior surface of the medial and lateral condyles of the femur by adding the average thickness of the posterior condyles of the smaller standard femoral prosthesis and the second distance;

a tool to resect the medial and lateral condyles along a plane at the anterior surfaces thereof flush with the anterior surface of the femoral cortex; and a tool to resect distal ends of the medial and lateral condyles at a resected thickness equal to the average thickness of the distal condyles of the smaller standard femoral prosthesis plus the second distance.

The apparatus further contemplates a tool to resect the measured thickness at the posterior surface of the medial and lateral condyles of the femur.

The invention also contemplates a method for forming planar resections on the medial and lateral condyles of a femur to form seating surfaces to receive a femoral prosthesis and to properly articulate with a tibial and patellar prosthesis comprises:

measuring for the size of the femoral prosthesis to be received by determining a first distance between an anterior surface of the femoral cortex and a plane tangent to a posterior surface of the medial and lateral condyles of a femur;

using a graduated scale to compare the first distance to at least two standard femoral prosthesis sizes;

measuring a second distance between the first distance and the size of the smaller standard femoral prosthesis size; and measuring a thickness or thicknesses to be resected at the posterior surface of the medial and lateral condyles of the femur, the thickness being equal to the average thickness of the posterior condyles of the smaller standard femoral prosthesis plus the second distance.

The method further contemplates the steps of resecting the medial and lateral condyles along a plane at the anterior surfaces thereof substantially flush with the anterior surface of the femoral cortex; and measuring a thickness or thicknesses to be resected at the distal ends of the medial and lateral condyles, the thickness being equal to the average thickness of the distal surface of the smaller standard femoral prosthesis plus the second distance, and resecting the distal ends of the medial and lateral condyles at the measured thickness.

Other features and advantages of the present invention will become apparent from the following description of the invention which refers to the accompanying drawings.

BRIEF DESCRIPTION OF THE DRAWINGS

FIG. 5 is a side view similar to FIG. 1 in which the tibia has been turned 90° to expose the distal end of the femur, an intramedullary rod has been inserted into the femur and a tool placed on the rod, the tool being partly broken away and shown in section.

FIG. 39 is a top view of the femur with the distal femoral cutting block mounted thereon.

FIGS. 40 and 41 are perspective views of distal femoral resection calipers for use in right and left femurs.

FIG. 46 is a top view of a spacer of the present invention.

FIG. 46a is an end view of the top extension portion of the spacer of FIG. 46.

FIG. 46b is an end view of the bottom flexion top extension portion of the spacer of FIG. 46.

FIG. 47 is a side view of the spacer of FIG. 46.

FIG. 48 is a front view of the knee space including a spacer in flexion.

FIG. 49 is a front view of the knee space including a spacer in extension.

DETAILED DESCRIPTION OF THE INVENTION

When performing a unicompartmental knee replacement, it is imperative to maintain the jointline at or near anatomic level. As a consequence, this maintains a full range of motion. The instrument system of the present invention has been developed which combines the advantages of anterior and posterior referencing systems to maximize motion in a reproducible fashion and can easily be incorporated into an operative protocol. With the instrument system of the present invention, orthopedic surgeons can reconstruct a knee and retain "anatomic" landmarks. This makes it possible to deal with many of the deformities confronting the orthopedic surgeon on an arthritic knee.

There are three ways that joint surgeons can insert a total knee replacement:

1) Resect the distal femur to accommodate the thickness of the femoral prosthesis. Resect the proximal tibia to accommodate the thickness of the tibial prosthesis. This recreates any lost motion and requires major soft tissue releasing. The flexion and extension resection spaces are not coordinated.

2) Rebuild the "normal" knee by compensating for loss articular cartilage and bone in the measurements for bony resection; then soft tissue releases can be performed to accommodate the proper dimensions. This places even greater demands on contracted soft tissues. Although this may be most anatomically correct, it requires such major tissue releases as to make it impractical.

3) Accept bony and articular cartilage loss. Resect the amount of bone in flexion and extension to accommodate full extension and as much flexion as deemed necessary. This method relies on a coordinated resection of the flexion-extension spacing. It relies on accurate measurements to allow for the resection of bone and minor soft tissue release. Within certain parameters, this method is preferable and can only be possible with better instrumentation, such as the instrumentation of the present invention.

Figure 1:
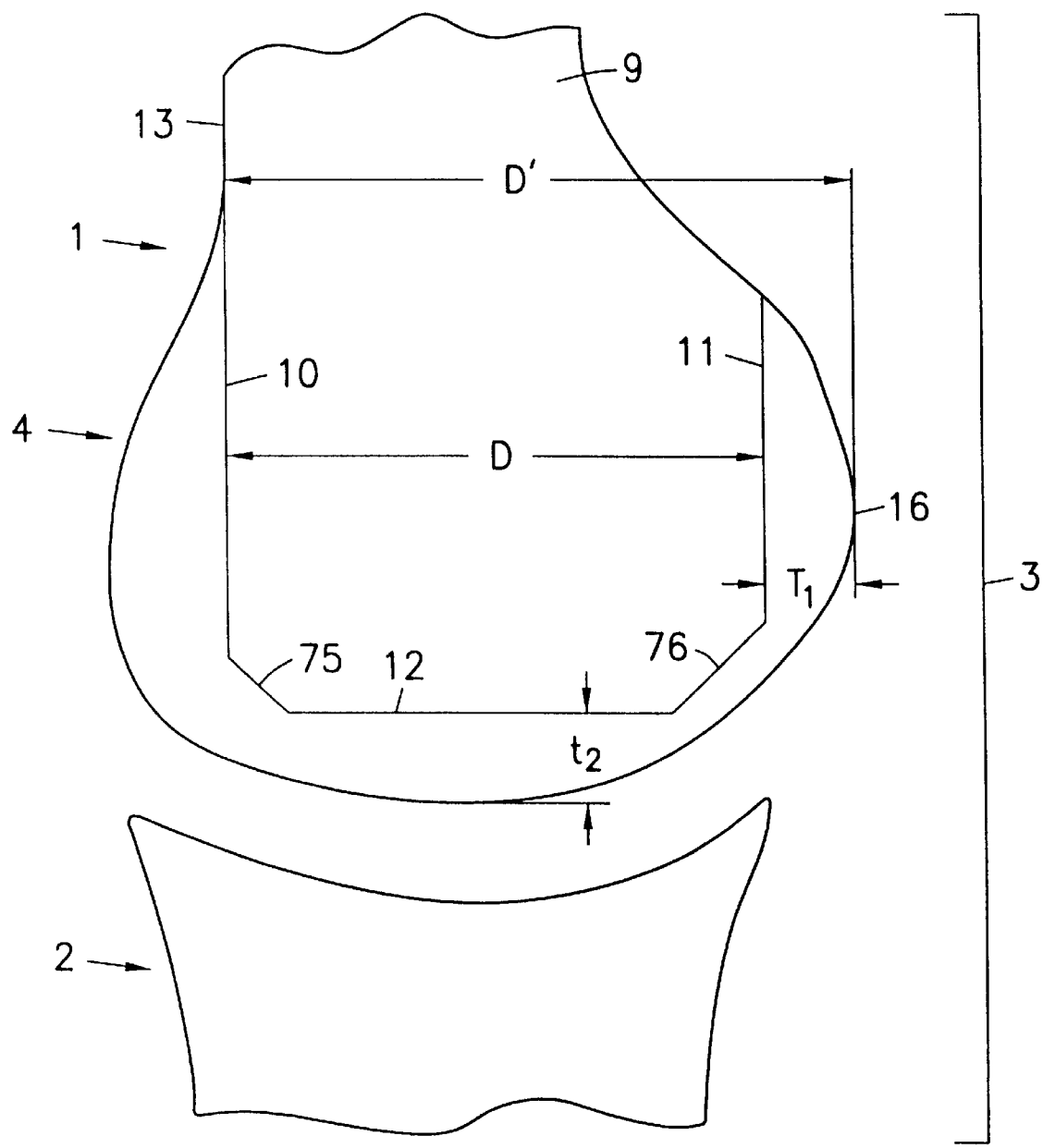
FIG. 1 is a diagrammatic, lateral view of the femur and tibia at a knee joint showing prospective cuts to be made on the femur for installation of a femoral prosthesis.
Figure 4:
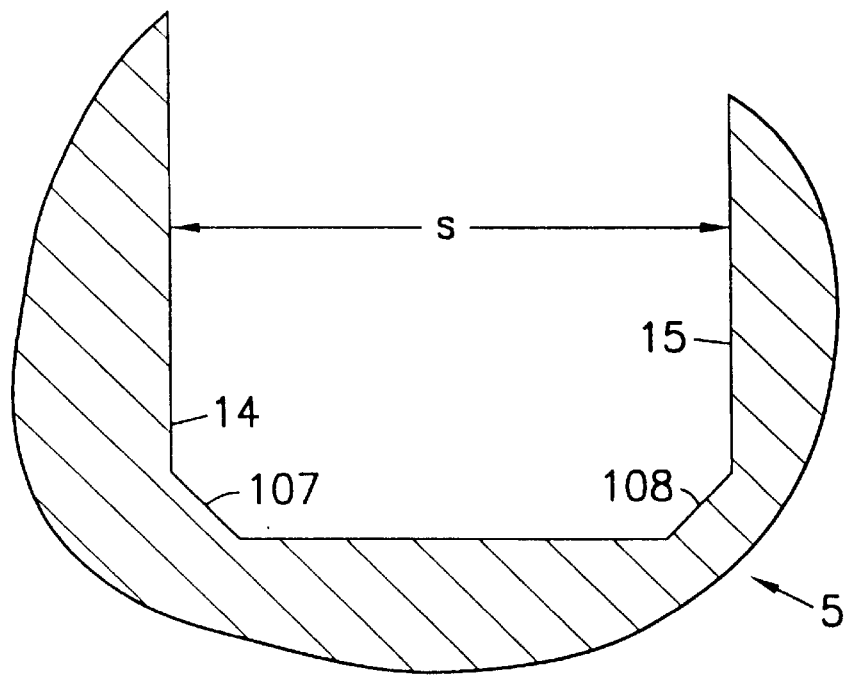
FIG. 4 is a sectional view of a femoral knee prosthesis adapted for placement on the femur after the planar cuts have been made on the femur.

Referring now to FIG. 1, the drawing diagrammatically illustrates the femur 1 and tibia 2 of a knee joint 3. The invention is concerned with the placement of planar resections or cuts at the distal condylar region 4 of the femur 1 to receive a femoral knee prosthesis 5 (FIG. 4). Typically, a total knee replacement also requires placing a planar cut at the proximal tibia of the tibia 2 to receive a tibial prosthesis, not shown. The tibial prosthesis typically consists of a tibial baseplate, not shown, that is fitted on the proximal tibia after the tibial cut is made, and an articular insert, not shown, secured to the baseplate to articulate with the femoral prosthesis 5.

The cut made on the tibia 2 and installation of the tibial knee prosthesis should be as close to the anatomic level as possible and should be substantially parallel to the floor in the mediolateral plane. This maintains the joint line at or close to anatomic level. Moreover, the angle of the proximal tibial resection should correspond to the angle of the distal femoral resections 12. For example, the proximal tibial is in mild varus and is resected such that the resection in the mediolateral plane is parallel to the floor and oriented posteriorly about 3°. Accordingly, the cuts made on the femoral prosthesis, discussed below, must also take into account this 3° mediolateral orientation in order to align the femoral prosthesis with the tibial prosthesis as will be explained later.

It is also important that the resected space medially in extension between the tibia 2 and the femur 1 of the knee equals the combined thickness of the medial tibial prosthesis and the distal medial femoral prosthesis; that the resected space laterally in extension between the tibia 2 and the femur 1 of the knee equals the combined thickness of the lateral tibial prosthesis and the distal lateral femoral prosthesis; that the resected space medially in flexion between the tibia 2 and the femur 1 of the knee equals the combined thickness of the medial tibial prosthesis and the posterior medial femoral prosthesis; that the resected space laterally in flexion between the tibia 2 and the femur 1 of the knee equals the combined thickness of the lateral tibial prosthesis and the posterior lateral femoral prosthesis; and that the resected space between the tibia 2 and the femur 1 of the knee in flexion must be equal to or greater than the resected space between the tibia 2 and the femur 1 of the knee laterally in extension, assuming normal ligament balance.

The condylar region 4 of the femur 1 is formed with a medial condyle 6 and a lateral condyle 7 separated by an intercondylar notch 8. The femur 1 includes a shaft 9 forming the femoral cortex, the condylar region 4 being at the distal end of the shaft 9.

In order to install the femoral knee prosthesis 5 on the distal condylar region 4 of the femur 1, three planar cuts are made in the condylar region 4 to form seating surfaces for the prosthesis 5. These cuts consist of an anterior cut 10, a posterior cut 11 and a distal end cut 12. The placement of these cuts 10, 11, 12 is crucial to the installation of the prosthesis 5 and its effect on the overall function of the prosthetic knee joint.

The invention is based on complying with the following conditions.

1. Forming the planar cut 10 at the anterior surface of the femoral condylar region flush with the anterior surface 13 of the femoral cortex so as to form a continuous surface therewith free of formation of either a notch or elevation at the juncture of cut 10 and surface 13.

2. Forming the planar cut 11 at the posterior surface of the femoral condylar region at a distance D from planar cut 10 equal to the interior dimension S between the anterior and posterior mounting surfaces 14, 15 of the prosthesis 5. The dimension S is the so-called A-P distance of the prosthesis and this distance varies for different size prosthesis. For example, prosthesis are categorized as small, small(+), medium, large, large(+) and extra large and the A-P distance increases in proportion to the size increase.

Figure 3:
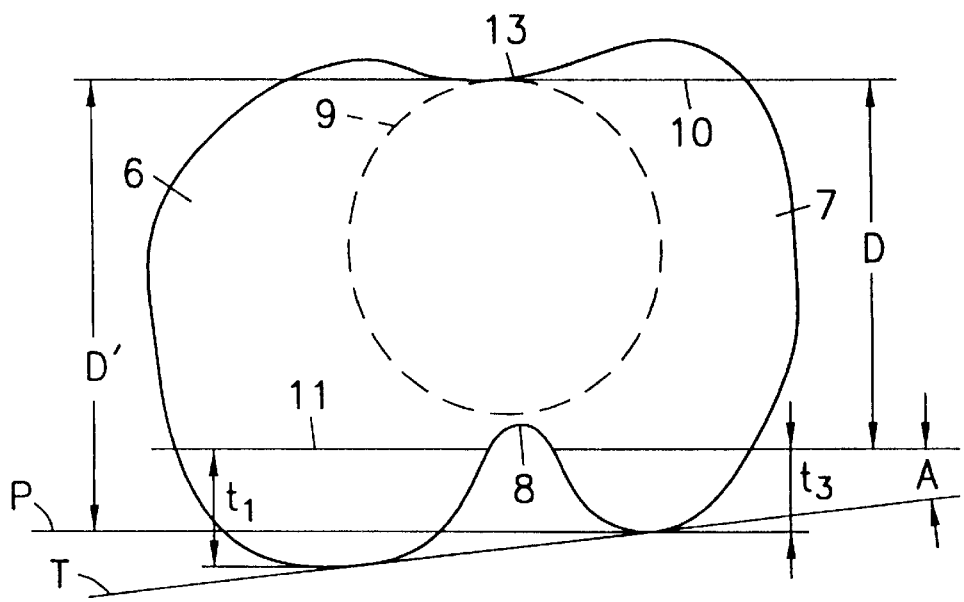
FIG. 3 is an end view from the distal end of the femur of the knee joint.

With reference to FIG. 3, therein is seen a plane T tangential to the medial and lateral condyles at the posterior surface 16 of the condylar region. The planar cut 11 is made at an angle A, with respect to plane T to angularly align the femoral prosthesis with the tibial prosthesis. Normally, the angle would be 3° to match the angle of the tibial prosthesis, however, due to anatomical conditions of the patient such as wear of the medial or lateral condyles posteriorly the angle A can vary substantially, generally between 0 and 15°. The planar cut 11 will result in resection of bone of a thickness $t_1$ at the medial condyle 6 and a thickness $t_3$ at the lateral condyle. The thickness $t_3$ is usually less than $t_1$ and controls the location of planar cut 11 so that a minimum thickness of bone is resected at the posterior surfaces of the condyles. In this regard, the thickness $t_3$ is established as the difference between distance D' between the anterior surface 13 of the femoral cortex and a plane P tangent to the posterior surface of the lateral condyle 7 and parallel to planar cut 11 and distance D between the anterior surface of the femoral cortex 13 and planar cut 11.

The thickness $t_3$ and the location of the prospective planar cut 11 therefore can be established based on measurement of the distance D and the A/P dimension of the selected size of the prosthesis. The size of the prosthesis is determined on the basis of the measurement of the distance D' and in general, the prosthesis size will be selected so that the thickness $t_3$ falls within a relatively narrow range, generally at least 6 mm and between 6 and 11 mm. The resected thickness of bone $t_1$ and $t_3$ at the medial and lateral condyles are generally unequal.

The distal end cut 12 is made so that the maximum thickness $t_2$ of bone resected at the distal end is substantially equal to $t_3$, i.e., the maximum thickness $t_2$ of bone resected at the more prominent condyle at the distal end (the medial condyle 6 in FIG. 2) is equal to the minimum thickness $t_3$ of bone resected at the posterior surface.

Referring now to FIG. 5, in order to establish the precise positions of the three planar cuts 10, 11, 12 to be made on the femur 1, a referencing or datum system is utilized which in the description herein is in the form of an intramedullary rod 20 installed in a bore 21 formed in the femur 1. The use of the intramedullary rod 20 as a benchmark or datum is known in the art and is illustrated herein by way of example. Other referencing or datum systems can be employed as well, for example, utilizing two pins placed in the condyles as set distance below the anterior femoral cut to position an AP cutting guide thereon. This will be described later.

Figure 7:
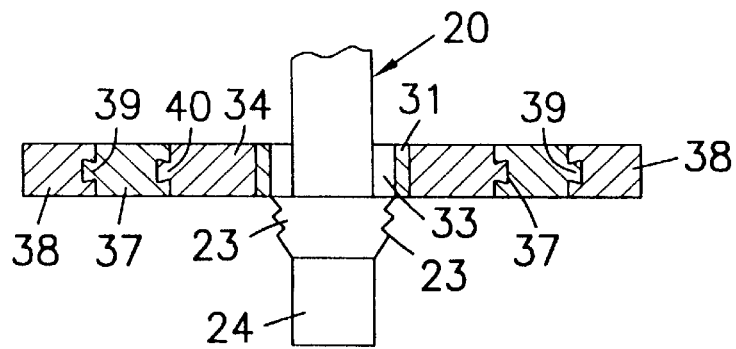
FIG. 7 is a sectional view taken on line 7—7 in FIG. 6.

The bore 21, which is approximately 8 mm in diameter, is formed longitudinally in the shaft 9 and in the condylar region 4 of the femur 1 at a location which is slightly anterior and medial of the intercondylar notch 8. The rod 20 has a cylindrical portion 22 which snugly fits in the bore 21 but is able to be rotated in the bore 21. The rod 20 may include radial flutes 23 extending outwardly a distance slightly greater than the diameter of the bore 21. The flutes 23 are initially outside the bore 21 and are intended to be driven into the bore 21 to fixedly secure the rod 20 in the bore 21. For this purpose, the flutes 23 are tapered to facilitate driving them into the bore 21 and grip the bore tightly in the distal femur 1 when driven therein. The outer ends of the flutes 23 can be saw-tooth or jagged as shown in FIG. 7 to provide a resilient gripping action.

The rod 20 includes an adjunct end or stub 24 which is non-circular in cross-section. The stub 24 may extend at an angle with respect to the longitudinal axis of the rest of the shaft so as to be substantially perpendicular to the joint and the prospective distal end cut 12 and parallel to the weight bearing axis of the leg. Shafts having stubs with different angles varying about 5–7° may be provided and selection is made on the sex, anatomical condition, and other conditions of the patient. This is conventional in prior usage.

The angular position of the non-circular stub 24 in bore 21 when the flutes 23 are driven into the bore 21 is a measure of the angle A at which the posterior and anterior cuts 11, 10 are made and, consequently, of the angular position of the knee prosthesis 5 on the femur 1 relative to the weight bearing axis of the leg.

The anatomical conditions governing the angular position of the rod 20 in the bore 21 is based on anatomy to maintain a straight line between the hip joint or the center of the femoral head in neutral rotation, the center of the knee joint and the midmedial third of the tibial plafond.

If the rod 20 initially assumes an angular position parallel to plane T, the rod is rotated by angle A to reach its datum position from which the cuts 10, 11, 12 will eventually be made. Nominally, the rotation is at an angle 3° to match the angle of the tibia prosthesis. However, due to wear of the condyles, and anatomical conditions of the patient the rotation of the rod must be varied from 3° to match the tibia prosthesis. The surgeon is readily able to estimate this angle based on the anatomy and on X-rays of the patient. Heretofore, however, the surgeon had to estimate the angle at which to set the rod 20 when the rod is driven into the bore 21. An imprecise estimate of the rotational orientation of the stub 24 can lead to angulation and placement errors of the prosthesis. Stated succinctly, the estimate of the surgeon of the angulation of cut 11 based on patient anatomy is accurate, but the "eyeballing" of the rotational position of the stub is often inaccurate.

The invention provides a tool or instrument 30 which is fitted on the stub 24 of rod 20 and accurately establishes rotation of the rod 20 when it is driven into the bore 21 and which measures the distance D' which in turn will determine the location of the planar cuts 10, 11, 12.

The tool 30 includes a sleeve 31 having a circular-like bore 32 of the same shape as the stub 24 in order to be fitted on the stub 24 for common rotation therewith. The bore 32 should include longitudinal slots or striations, e.g., star-shaped. The sleeve 31 has grooves 33 aligned with flutes 23 to permit passage of the flutes 23 through the sleeve 31 when the rod 20 is driven into the bore 21 in the shaft 9 of the femur 1. The sleeve 31 is rotatably supported in a slider 34 which is slidably supported by a lower half 35 of a caliper means whose upper half 36 is slidably engaged with lower half 35. The upper and lower halves 36, 35 are formed as open U-shaped members forming adjacent legs 37, 38 which are slidably engaged by tongue and groove engagement means 39. The slider 34 is slidably engaged in the legs 37 of the lower half 35 of the caliper means by a tongue and groove engagement means 40.

A cross leg 41 at the closed end of the lower half 35 of the caliper means engages a bar 42 for slidable movement in a direction substantially perpendicular to the direction of slidable movement of slider 34. The bar 42 is formed with opposed flats 43 on which the cross leg 41 can slide without undergoing rotation. The bar 42 is provided with forwardly facing pins 44 at end regions thereof.

Figure 8:
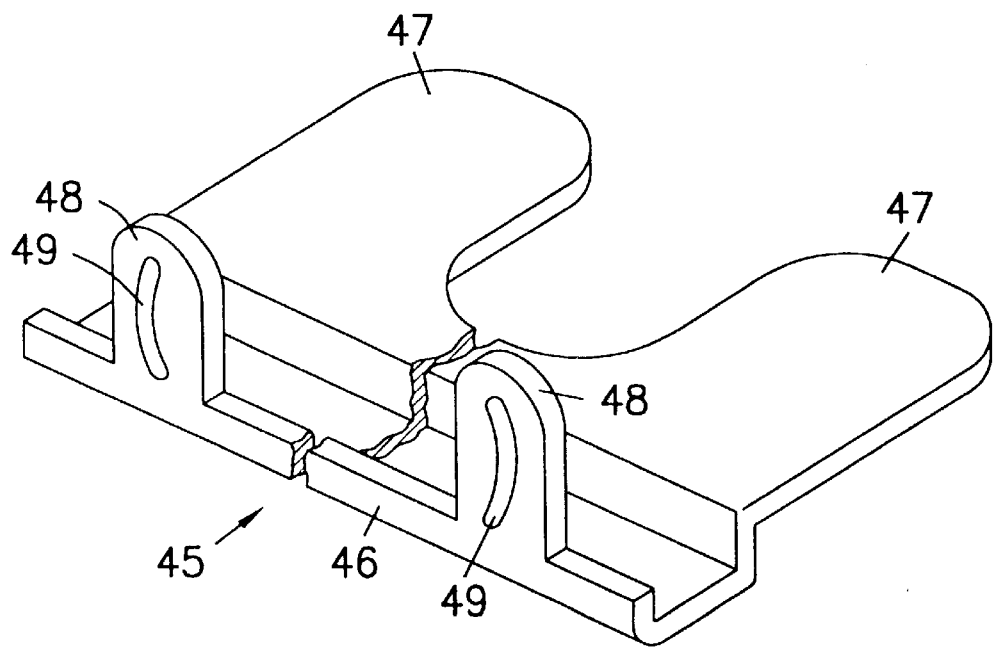
FIG. 8 is a broken, perspective view of a lower caliper feeler of the tool.

A posterior caliper 45 is mounted on the pins 44. The posterior caliper 45 includes a caliper plate 46 with spaced caliper feelers 47 (FIG. 8) for respectively contacting the posterior surfaces of the medial and lateral condyles. A pair of upright legs 48 are provided on plate 46 and the legs 48 are provided with respective slots 49 to receive respective pins 44 of bar 42. The slots 49 are part-circular in extent and have a common center such that either pin 44 can ride its respective slot 49 and change the angle of bar 42 relative to the caliper plate 46. The ends of the pins 44 are threaded and nuts 50 are engaged on the threaded ends to lock the position of the pins 44 in the slots 49.

At the top of upper half 36 of the caliper means is an integral upstanding projection 60 which is integral with a guide bar 61. The guide bar 61 extends substantially perpendicular to the plane of the caliper halves 36, 37. The guide bar 61 has a bore 62 at one end thereof in which is slidably fitted an end of a rod 63 of an anterior caliper feeler 64 for extension and retraction adjustment movement of the anterior caliper feeler 64. A nut 65 secures the position of the rod 63. At the end of the rod 63 of the anterior caliper feeler 64 is a sector plate 66 which is pivotally supported at 67 by the rod 63. The sector plate 66 has a part-circular surface 68 adapted to contact the anterior surface 13 of the femoral cortex. The surface 68 has its center at the pivotable support point 67.

Figure 2:
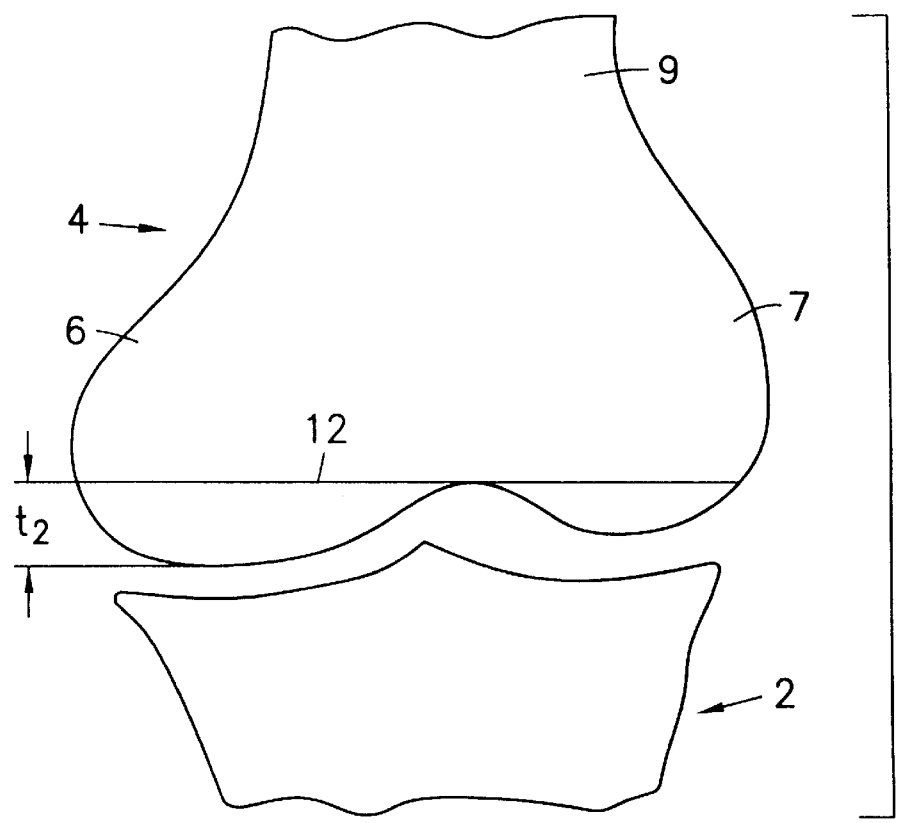
FIG. 2 is a diagrammatic illustration of the knee joint of FIG. 1 seen anteriorly of the joint.

In operation, the femur 1 is rotated 90° from the position shown in FIG. 2 to the position in FIG. 3 or 5 so that the distal end of the femur 1 is exposed. The bore 21 is formed in the femur 1 and the rod 20 is inserted into the bore 21. The tool 30 is then installed in the rod 20 by fitting the bore 32 in sleeve 31 on the stub 24 of the rod 20 projecting from the distal end of the femur 1. The posterior caliper feelers 47 are respectively brought into contact with the posterior surfaces of the respective medial and lateral condyles. This effectively establishes the position of plane T as described in FIG. 3.

Figure 9:
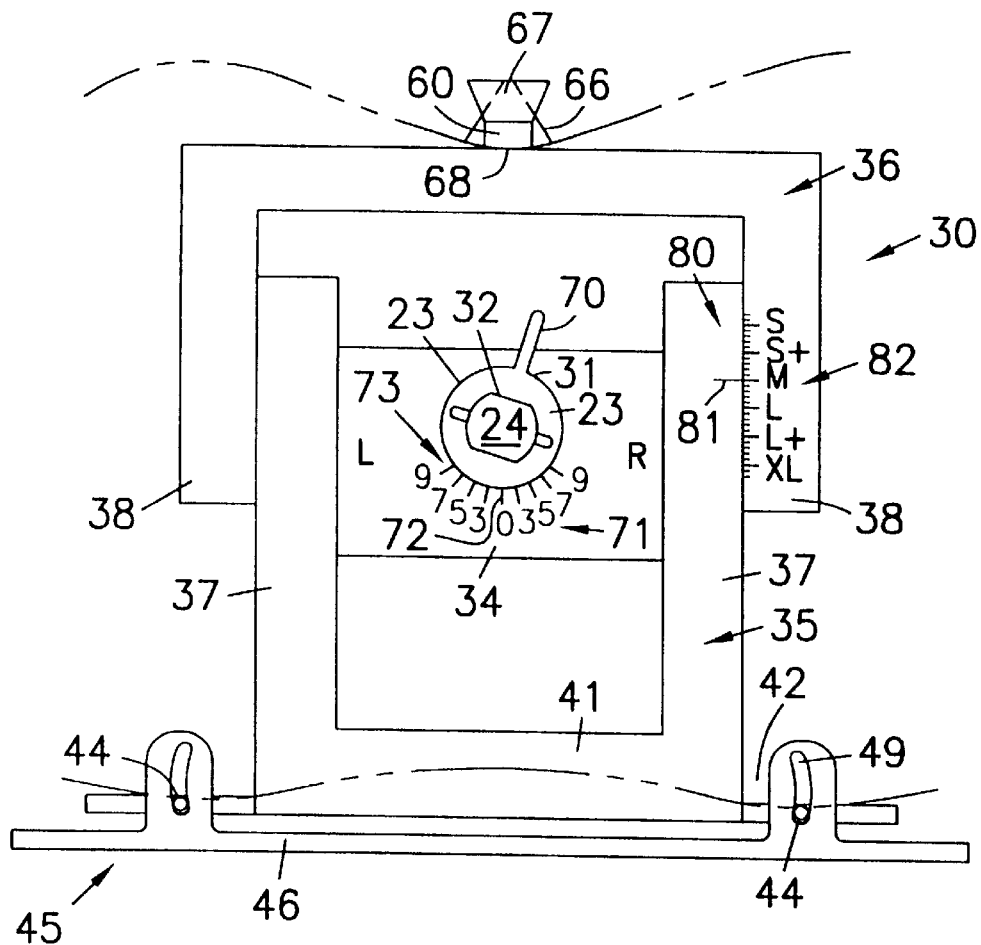
FIG. 9 is similar to FIG. 6 and illustrates a first stage in which the rod is angularly rotated by a specific amount.
Figure 27:
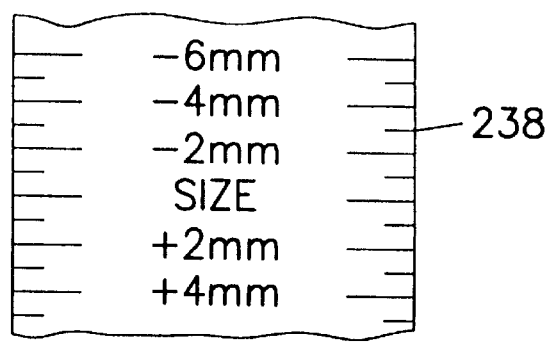
FIG. 27 is an enlarged fragmentary view of the sliding scale of the distal cutting block.

A radially projecting tab 70 on the sleeve 31 is manually engaged to rotate the sleeve 31 through angle A representing the angle determined by the surgeon as explained previously. A scale 71 is provided to indicate the angle through which the sleeve 31, and thereby the rod 20, has been turned. The scale 71 comprises an index marker 72 on the sleeve and an angle scale 73 on the slider 34. The scale 73 is marked for left and right femurs. For left femurs (described and illustrated in the drawing) the sleeve and rod are rotated to the right (clockwise) whereas when the tool is mounted on a rod in the right femur, the sleeve and rod are rotated to the left (counter clockwise). When the scale 71 indicates the desired angle of rotation, the sleeve 31 is rotatably locked in the slider 34 by suitable means (not shown) and the rod 20 is driven into the bore 21 of the femur 1 to be angularly secured thereon in the desired rotational position relative to the plane T tangential to the posterior surfaces of the medial and lateral condyles. This is the position shown in FIG. 9.

Figure 10:
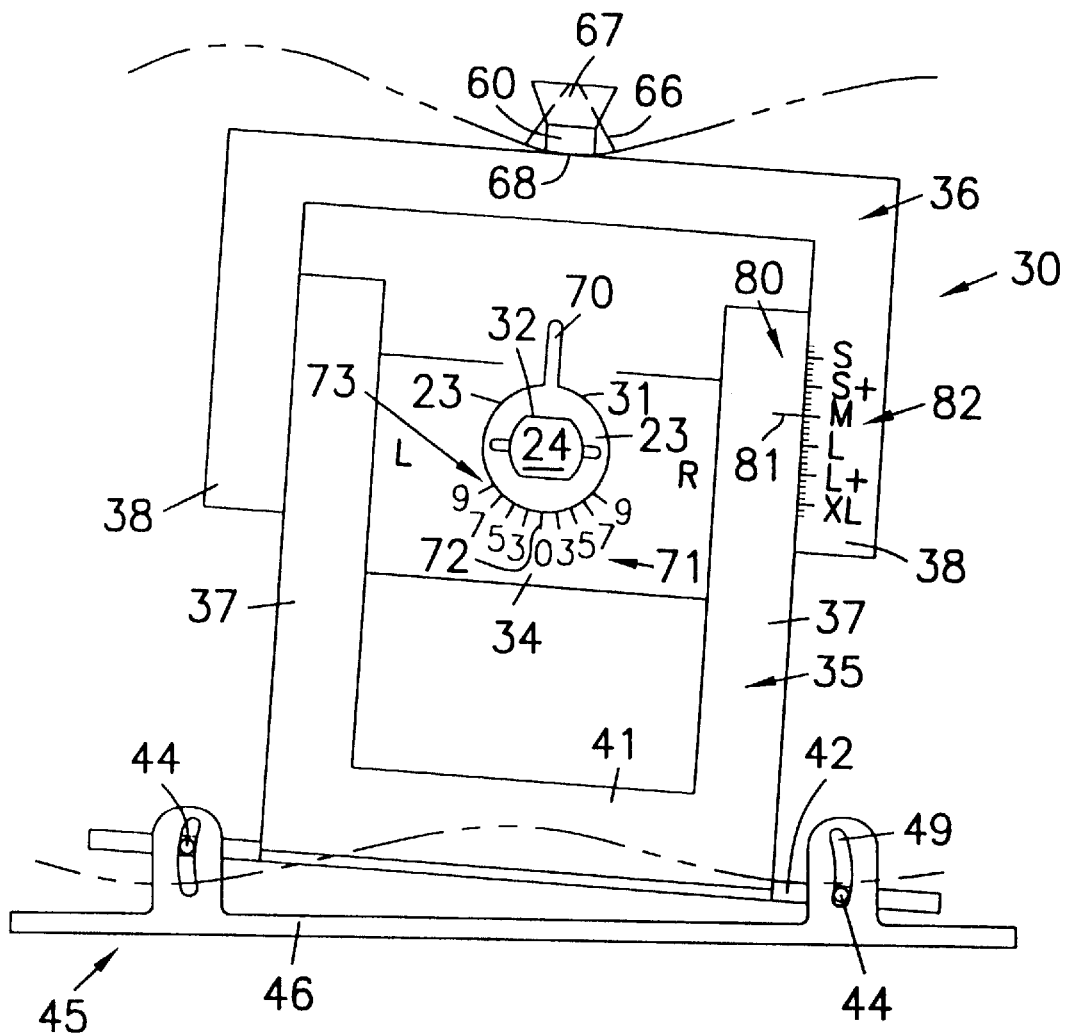
FIG. 10 is similar to FIG. 9 in a subsequent stage.
Figure 11:
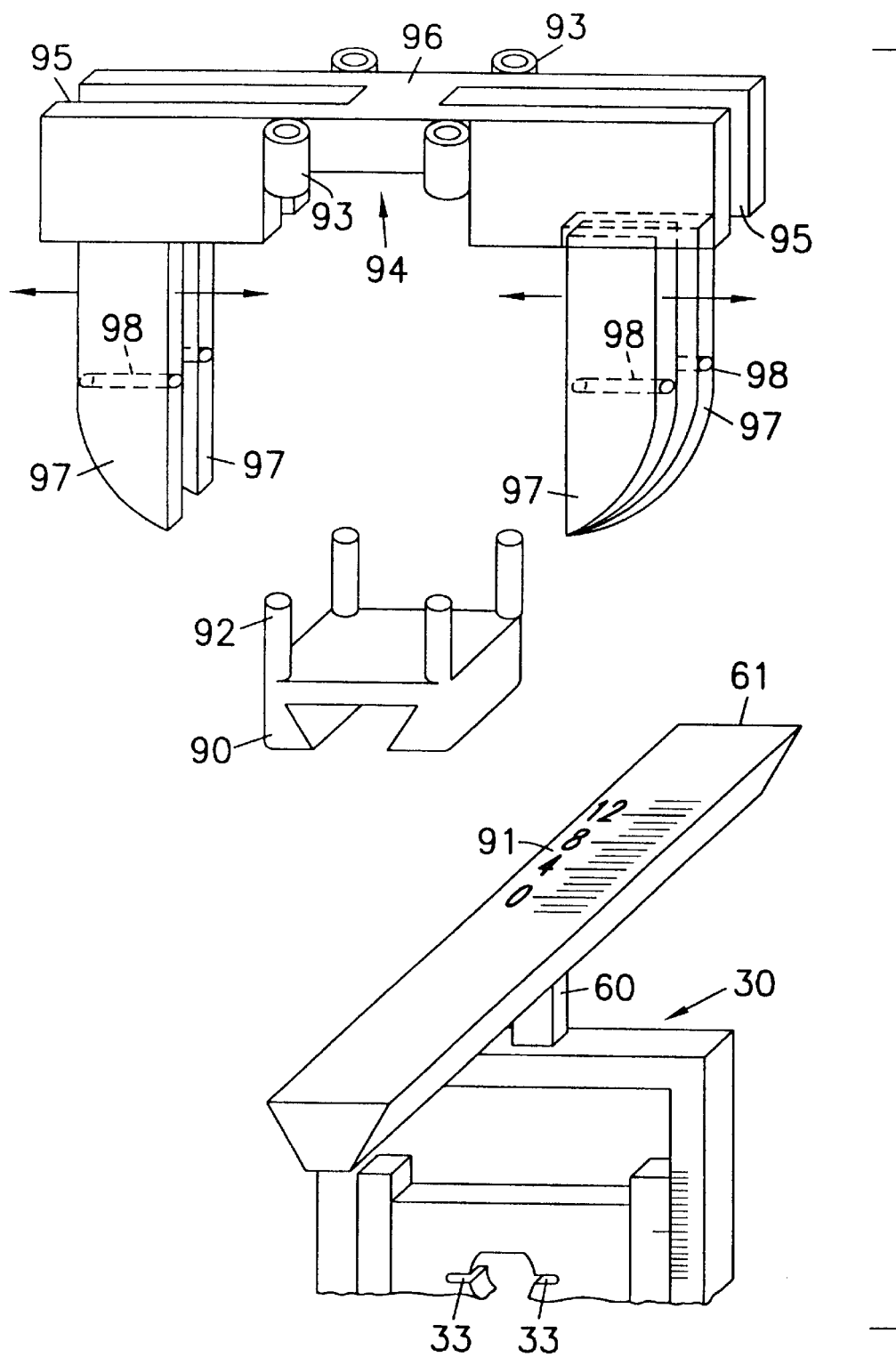
FIG. 11 is an exploded view showing a cutting guide to be installed on the tool.
Figure 12:
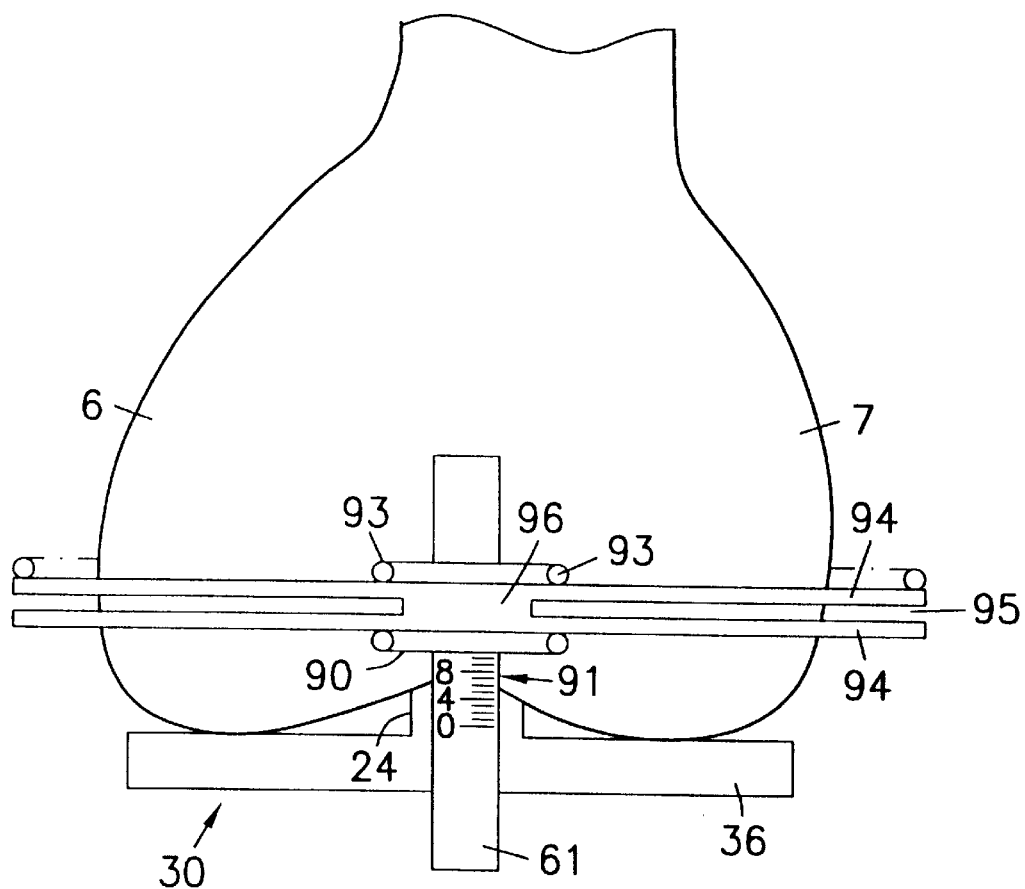
FIG. 12 is a top, plan view showing the cutting guide installed on the tool.

In order to set the caliper means in position to measure the distance D', the nuts 50 on pins 44 are loosened and the upper and lower caliper halves 36 and 37 are rotated as a unit around pin 44 at the lateral femoral condyle until the index marker 72 returns to its zero setting on the scale 73 as shown in FIG. 10. The nuts 50 are then tightened and the caliper halves are now in a position to measure distances perpendicular to the plane P tangent to the posterior surface of the lateral condyle. The capability of slidable movement of the slider 34 on the lower caliper half 35 and of the caliper half 35 relative to bar 42 and posterior caliper feeler 45 permits the rotation of the caliper halves about pin 44 at the lateral condyle while the sleeve 31 and the slider 34 are engaged with the stub 24 of rod 20.

The anterior feeler 64 is then positioned so that sector plate 66 contacts the anterior surface 13 of the femoral cortex. A distance scale 80 is provided between the upper and lower caliper halves 36, 35 and comprises a marker 81 on leg 37 and a scale 82 on leg 38. The scale 82 indicates the prosthesis size and hence is a measure of the distance D. The calibration is such that when the marker 81 is in correspondence with a mark on scale 82 for a particular prosthesis, when this prosthesis is utilized, the difference between D and D' (the thickness $t_3$ resected at the posterior condyle) will be substantially equal to the thickness of the prosthesis to be inserted. If the scale falls between prosthesis markings on scale 82, generally the smaller prosthesis is selected and the resected thickness of the lateral condyle will be slightly increased accordingly. The scale markings can also be calibrated with reference to the resected thickness $t_1$ at the medial condyle to reflect the normally greater thickness resected thereat.

With the tool still mounted on the rod 20, the anterior feeler 64 is removed and a guide 90 is slidably fitted on guide bar 61. At the top of the guide bar 61 another scale 91 is provided. The scale 91 is marked in millimeters and represents the distance from a plane perpendicular to the rod and tangent to the high point of the distal end surface of the more prominent of the medial or lateral condyles. In other words, when the tool 30 remains on the rod 20 and is brought into abutment with the condyles, this is the zero position of the scale 91. The guide 90 has four upstanding pegs 92 which fit into four holes 93 of a distal end cutting guide 94.

The cutting guide 94 is provided with slots 95 extending in a plane substantially perpendicular to the axis of stub 24. The slots 95 extend from the medial and lateral side surfaces of the cutting guide 94 towards the center thereof. The slots 95 are adapted to guide a narrow cutting blade (not shown) for respectively cutting the medial and lateral condyles 6, 7 along planar cut 12. The slots 95 are separated by a solid, intermediate section 96.

The position of the slots 95 relative to the scale indicate the thickness $t_2$ to be resected by the planar cut 12 at the distal end of the femur 1. The invention contemplates that the thickness $t_2$ may be equal to the thickness $t_3$ determined by the measurement of distance D'. Therefore, the guide 90 is moved until the slots 95 are aligned with the distance on scale 91 equal to the determined thickness $t_3$. The guide 90 is then locked on guide bar 61 by suitable means (not shown).

Depending feet 97 are slidably mounted on cutting guide 94 in respective pairs on opposite sides of each slot 95. After the cutting guide 94 has been moved to its cutting position as indicated on scale 91, the depending feet 97 are slidably moved to abut against respective portions of the condyles. The feet 97 are provided with nail holes 98 and nails (not shown) are driven into the holes 98 to secure the cutting guide 94 to the femur 1. A conventional cutting blade is then inserted in guide slots 95 to cut the distal ends of the condyles 6, 7 along the planar cut 12. The feet 97 nailed to the condyles prevent skewing or sliding of the cutting guide during the cutting operation.

Figure 13:
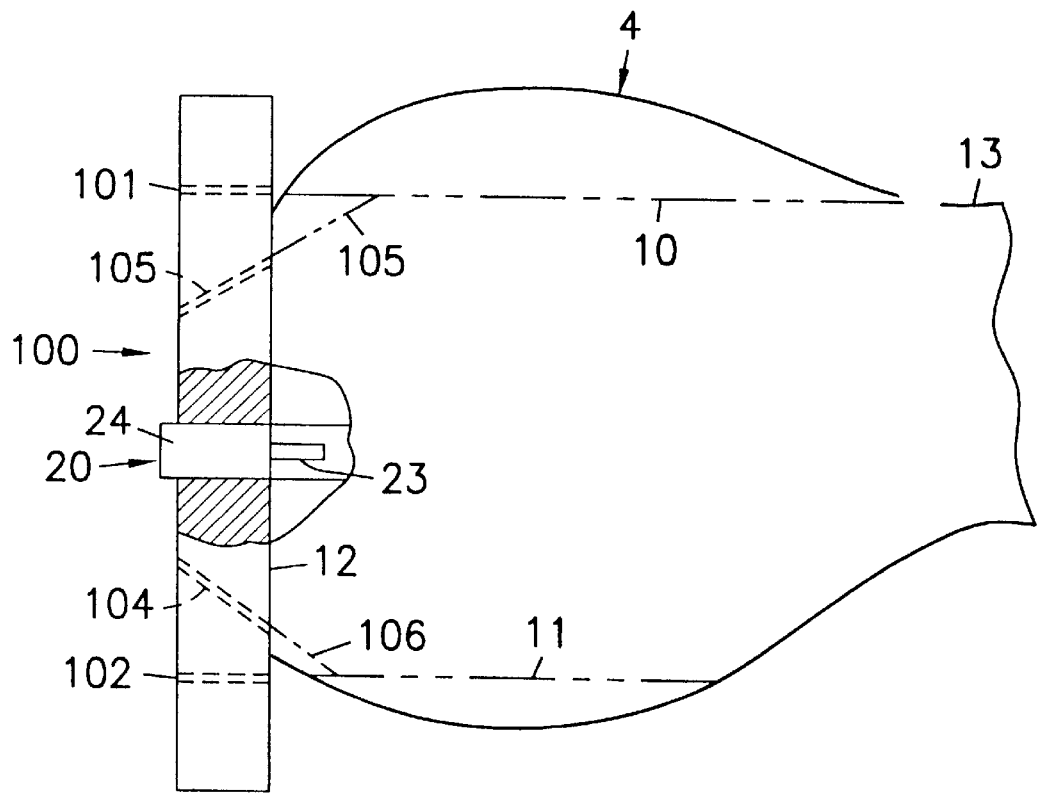
FIG. 13 illustrates the distal end of the femur after the distal end has been cut and an AP cutting guide has been placed on the rod.
Figure 24:
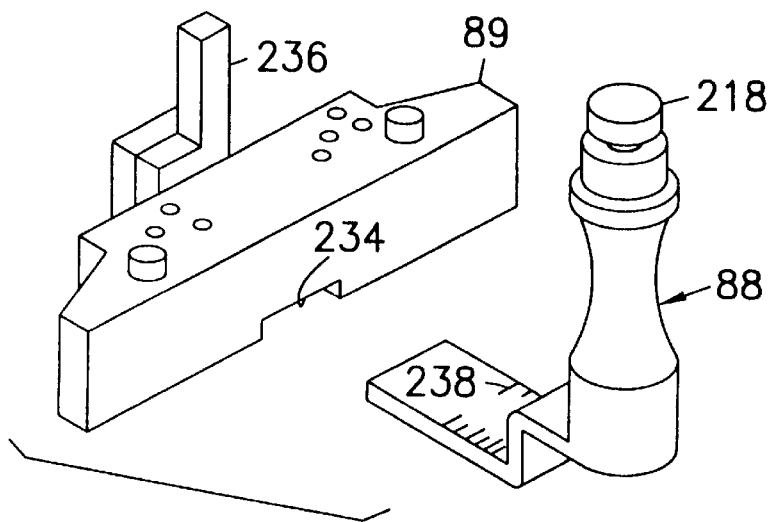
FIG. 24 is an exploded view of a distal cutting block to be installed on the tool of FIG. 21.

The tool 30 is then removed from the rod 20 and a conventional AP cutting guide 100 (FIG. 13) is fitted on the end of the rod 20 and abutted against the planar surface 12 now cut at the distal end of the femur 1. The cutting guide 100 is provided with guide slots 101 and 102 which can be precisely placed for guiding a cutting blade to produce the anterior and posterior cuts 10, 11 respectively. The cut 10 will be flush with anterior surface 13 of the femoral cortex and the cut 11 will be at distance D therefrom. The AP cutting guide 100 also includes angular slots 103, 104 to form chamfer cuts 105, 106 on the femur 1 which match corresponding angular surfaces 107, 108 on the knee prosthesis 5.

Figure 14:
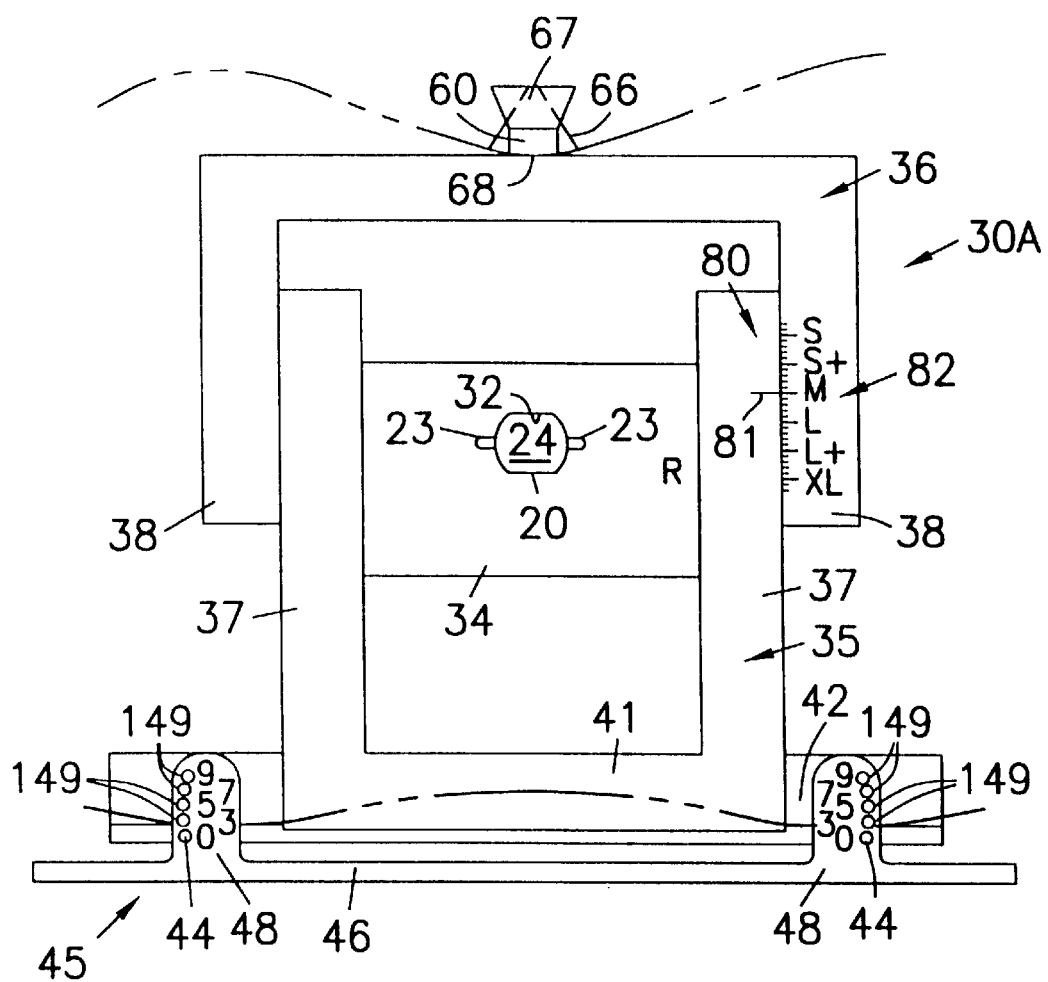
FIG. 14 is an end view similar to FIG. 6 of a second embodiment of the tool.
Figure 15:
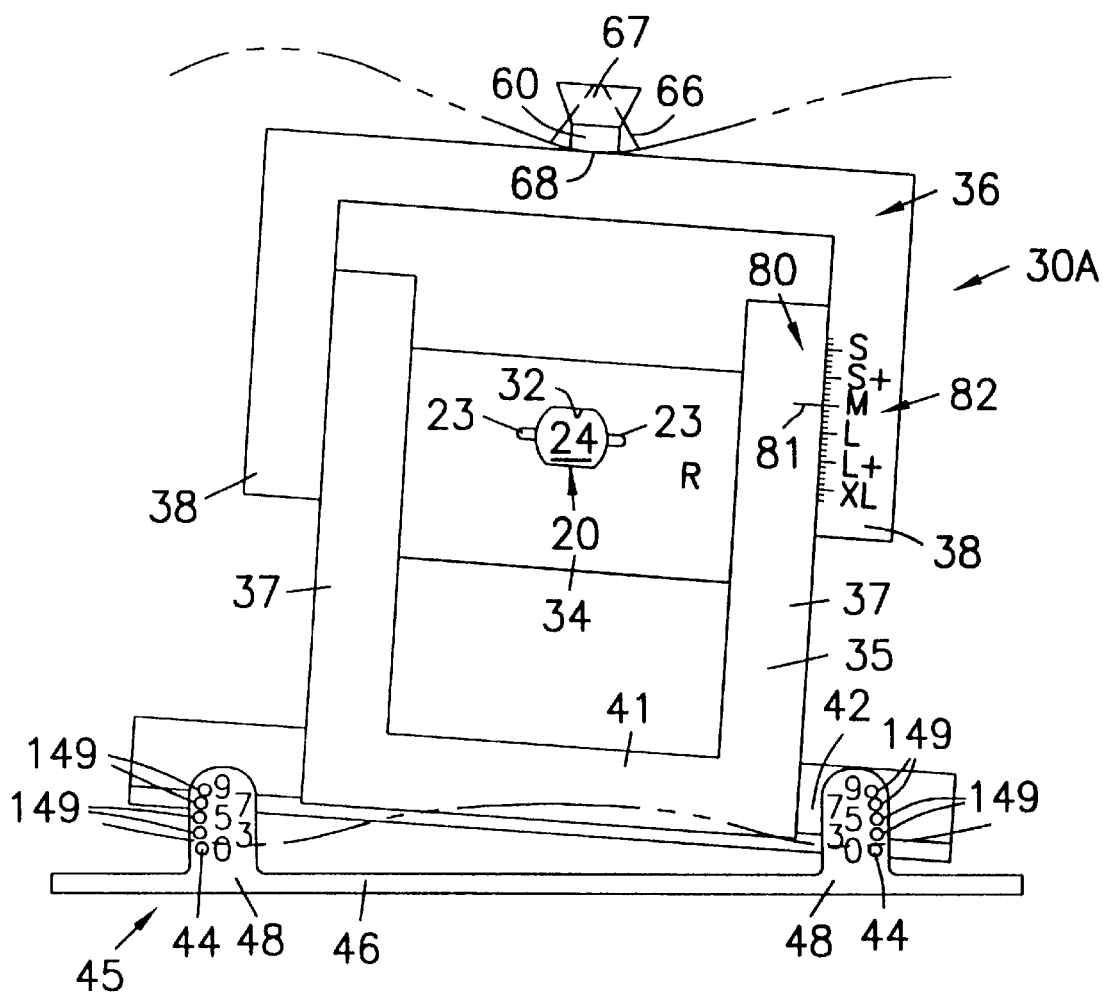
FIG. 15 shows the tool of FIG. 14 in a rotated state.

FIGS. 14 and 15 illustrate a second embodiment of a tool 30A which is a simpler version of the first embodiment of FIGS. 5–10 and wherein the same reference characters are used to designate like elements.

Essentially, the embodiment of the tool 30A of FIGS. 14 and 15 differs from that of FIGS. 5–10 in eliminating the rotatable sleeve 31 and directly engaging the stub 24 of rod 20 in bore 32 now provided directly in the slider 34. The slider 34 thus serves as the engaging means for the stub 24. The legs 48 on the caliper plate 46 are provided with spaced holes 149 instead of the continuous slot 49 of the embodiment of FIGS. 5–10 and angular markings 173 are provided adjacent to the holes 149 to indicate the magnitude of angle A between the caliper plate 46 and bar 42, serving as a measurement plate, when the pin 44 is in the respective hole 149. In the illustrated embodiment in FIGS. 14 and 15, the holes 149 are placed to provide angulations of 0, 3, 5, 7 and 9° left and right between bar 42 and caliper plate 46.

In operation, the stub 24 is engaged in the bore 32 in slider 34 and pins 44 are placed in the 0° holes in respective legs 48. The caliper feelers 47 are placed into tangential contact with the posterior surfaces of the medial and lateral condyles 6, 7 respectively. The pin 44 in the leg 48 corresponding to the medial condyle is then removed from the 0° hole and placed in the hole 149 corresponding to the desired angulation of the rod 20. This is shown in FIG. 15 where pin 44 is set in the hole 149 to angulate the bar 42, 7° relative to the caliper plate 46 and thereby relative to the plane T tangent to the medial and lateral condyles. By virtue of the slidable supported of slider 34 in legs 37 and the slidable support of cross leg 41 on bar 42, the tool 30A is capable of remaining in position on stub 24 and rotating around pin 44 at the posterior surface of the lateral condyle 7.

The measurement by the caliper means to determine the size of the prosthesis and the resected thickness $t_3$ at the lateral condyle is carried out in the same way as in the first embodiment and the planar cuts are then made on the condyles as previously described.

As was described for the first embodiment of tool 30, it is also possible to effect measurement with the tool 30A to determine thickness $t_1$ at the medial condyles and to utilize this thickness to establish the thickness $t_2$ distal cut 12.

Both the first and second embodiments have been described with regard to the intramedullary rod 20 with radial flutes 23 to embed the rod securely in the bore 21 in the femur 1 to establish the datum or benchmark position for attaching the cutting guide 60 to effect the distal end cut 12 and thereafter the AP cutting guide 100 to effect the anterior and posterior planar cuts 10, 11. However, other suitable means can be employed to secure the angular position of the rod instead of the flutes 23. Moreover, since the rod 20 is ultimately removed from the femur 1 after the planar cuts 10, 11, 12 have been made, the absence of the flutes 23 makes removal simpler.

Figure 16:
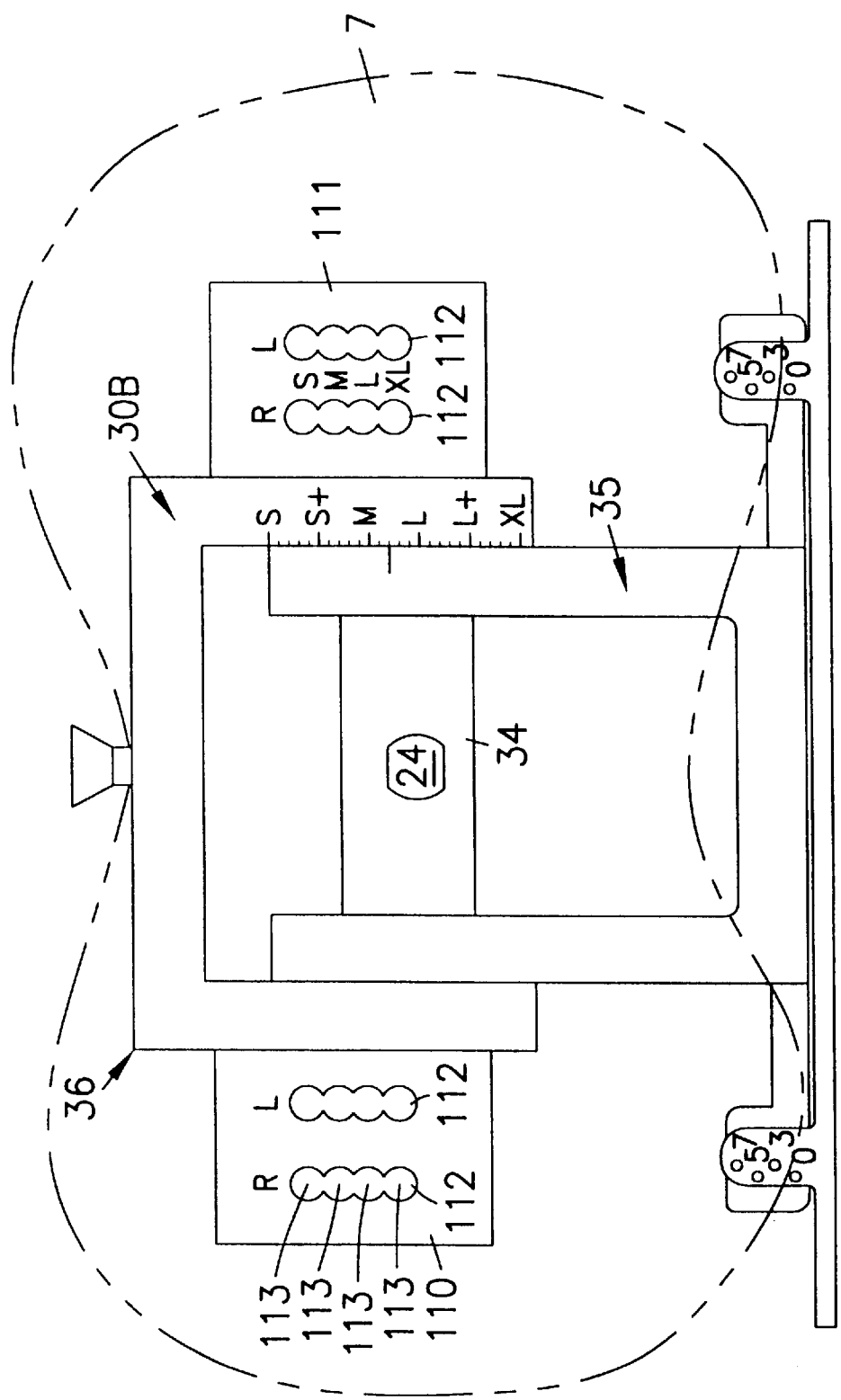
FIG. 16 is an end view similar to FIG. 6 of a third embodiment of the tool.
Figure 17:
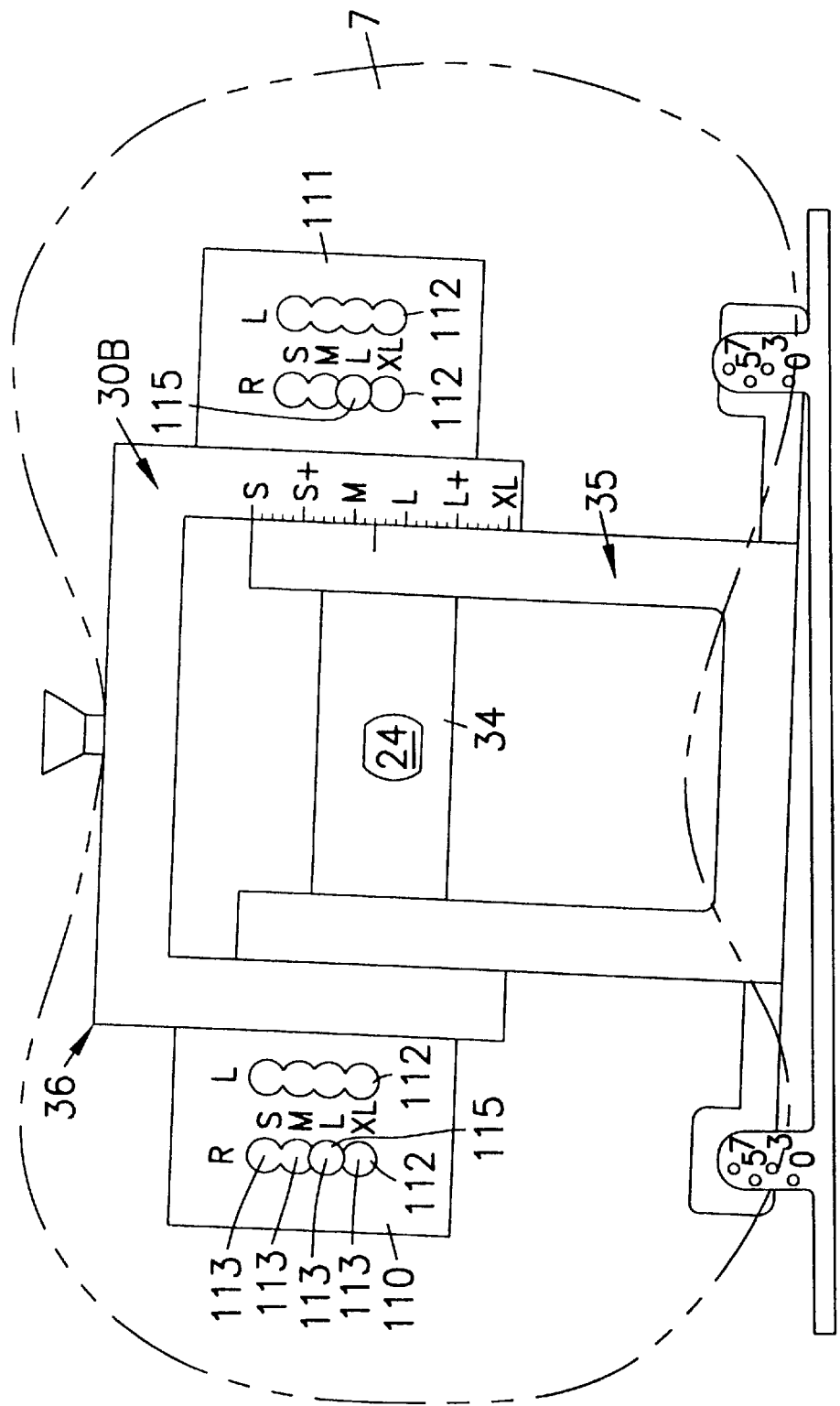
FIG. 17 shows the tool of FIG. 16 in a rotated state.

FIGS. 16 and 17 illustrate a third modified embodiment of the tool 30B which secures the angular datum position by use of a rod without flutes 23. The same reference characters as in the first two embodiments designate like elements.

In the third embodiment, the rod 20 is smooth and devoid of flutes 23. The rod 20 is rotated to its adjusted angular position, as in the first and second embodiments, and in order to secure an angularly adjusted datum position, lateral plates 110, 111 are secured to the legs 38 of the upper caliper half 36. Each plate 110, 111 contains two vertical rows 112 of overlapped holes 113. The rows 112 are designated for right and left femurs and the holes 113 are respectively graduated in size order from the scale 82. When the caliper means of the tool 30B has been rotated to the desired degree of angulation, pins 115 or similar fasteners are placed in the appropriate holes 113 in the lateral plates 110, 111 and secured in the distal ends of the medial and lateral condyles so that the pins 115 project from the distal ends of the condyles. The pins 115 establish an angular datum position representing the rotation of the tool. The steps of measurement of prosthesis size, and of effecting the planar cut with the guide 60 are carried out as in the previously described embodiments. However, after the distal end cut 12 is made, the tool 30B is removed leaving the pins 115 in place in the condyles, the rod 20 is removed from the femur 1, and a guide 100' is mounted on the pins 115 which serve to accurately position the guide 100' so that the slots 101–104 will be precisely located for exact placement of the cuts 10, 11, 105 and 106. The guide 100' has holes 116 to receive the pins 115 which are precisely located with regard to the slots 101–104 to insure accurate location of the cuts when the guide 100' is mounted on the pins 115. After the cuts have been made, the pins 115 are removed from the condyles. As evident from the above, the embodiment contemplates the use of the pins 115 as the means to provide the datum position for the cutting guide 100' in lieu of the rod 20. The use of the plates 110, 111 and of the pins 115 is applicable to the other embodiments as well.

Figure 18:
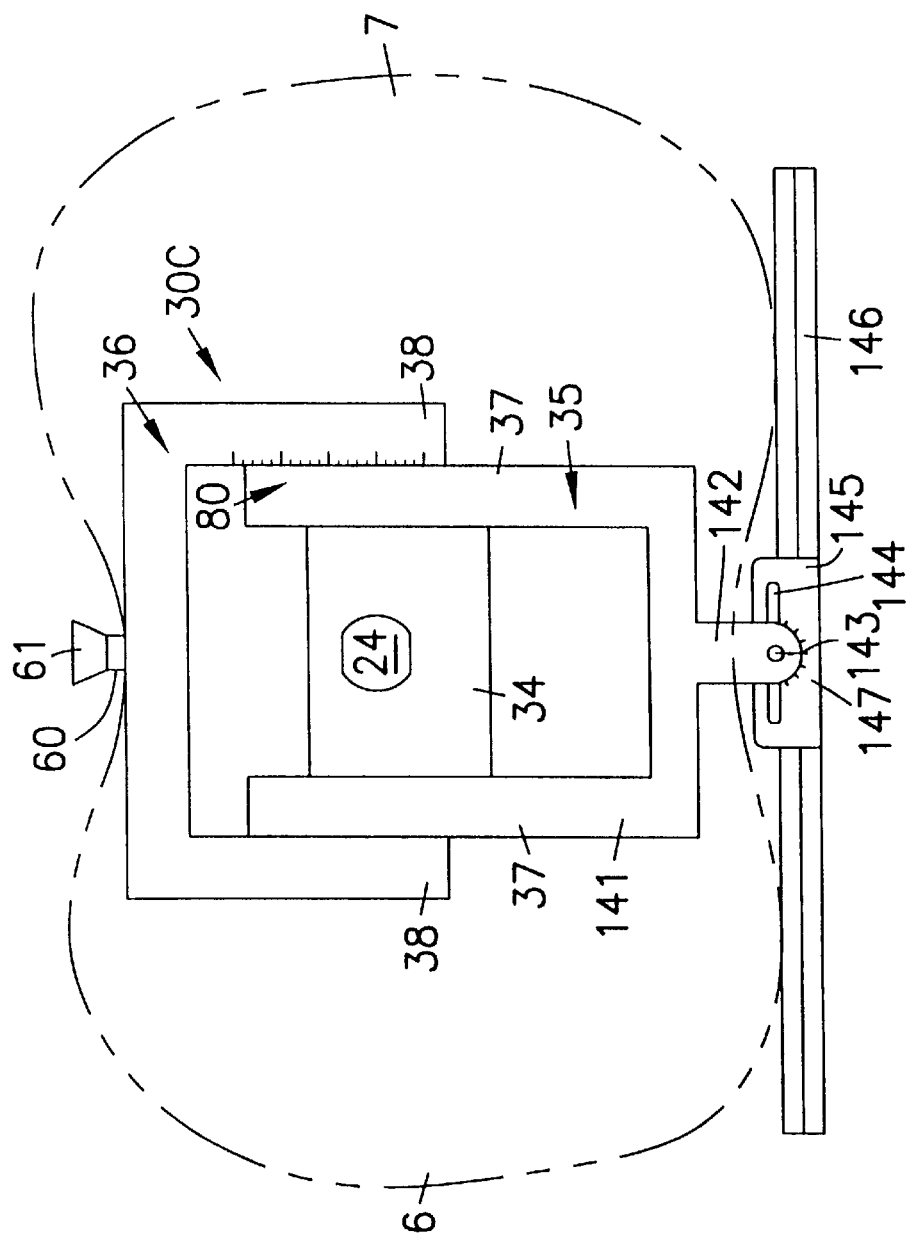
FIG. 18 is an end view similar to FIG. 6 of a fourth embodiment of the tool.
Figure 19:
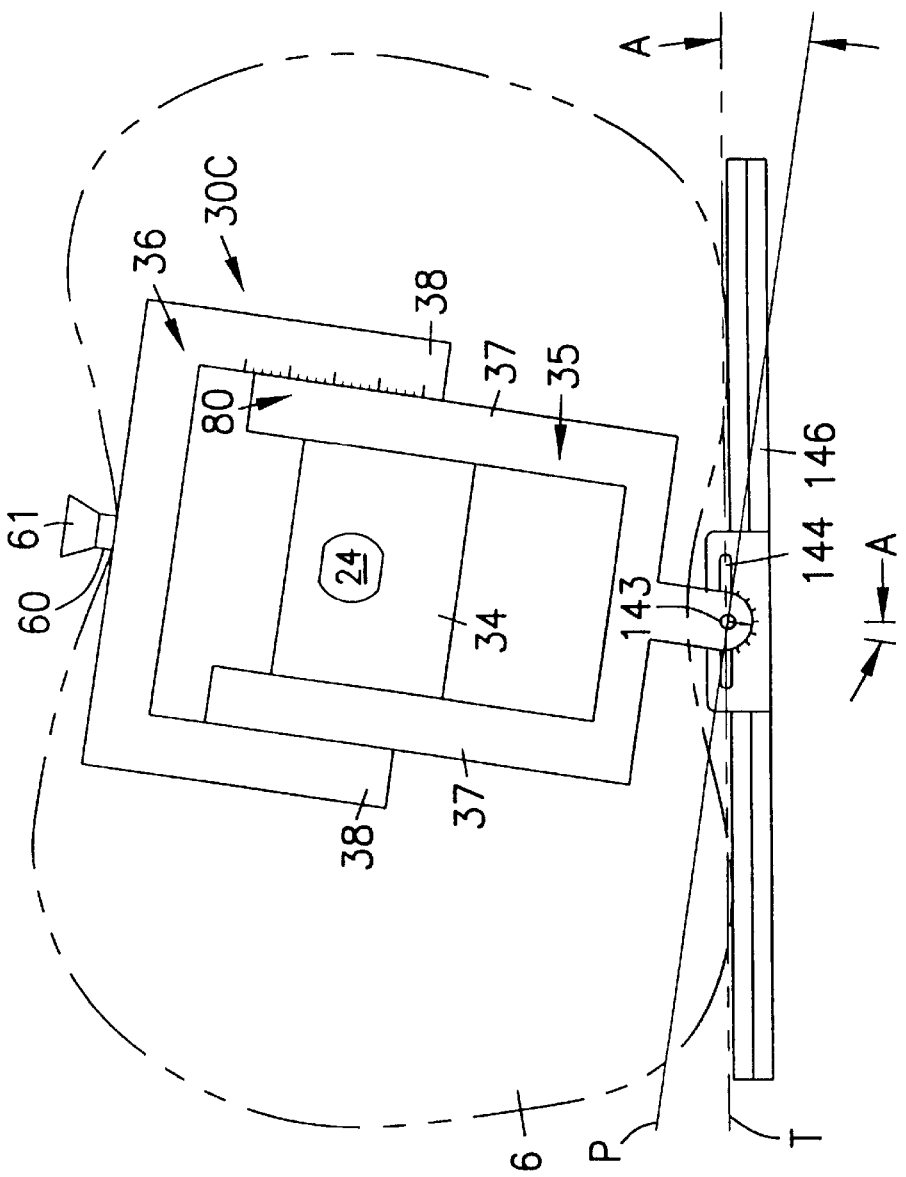
FIG. 19 shows the tool of FIG. 18 in a rotated state.
Figure 20:
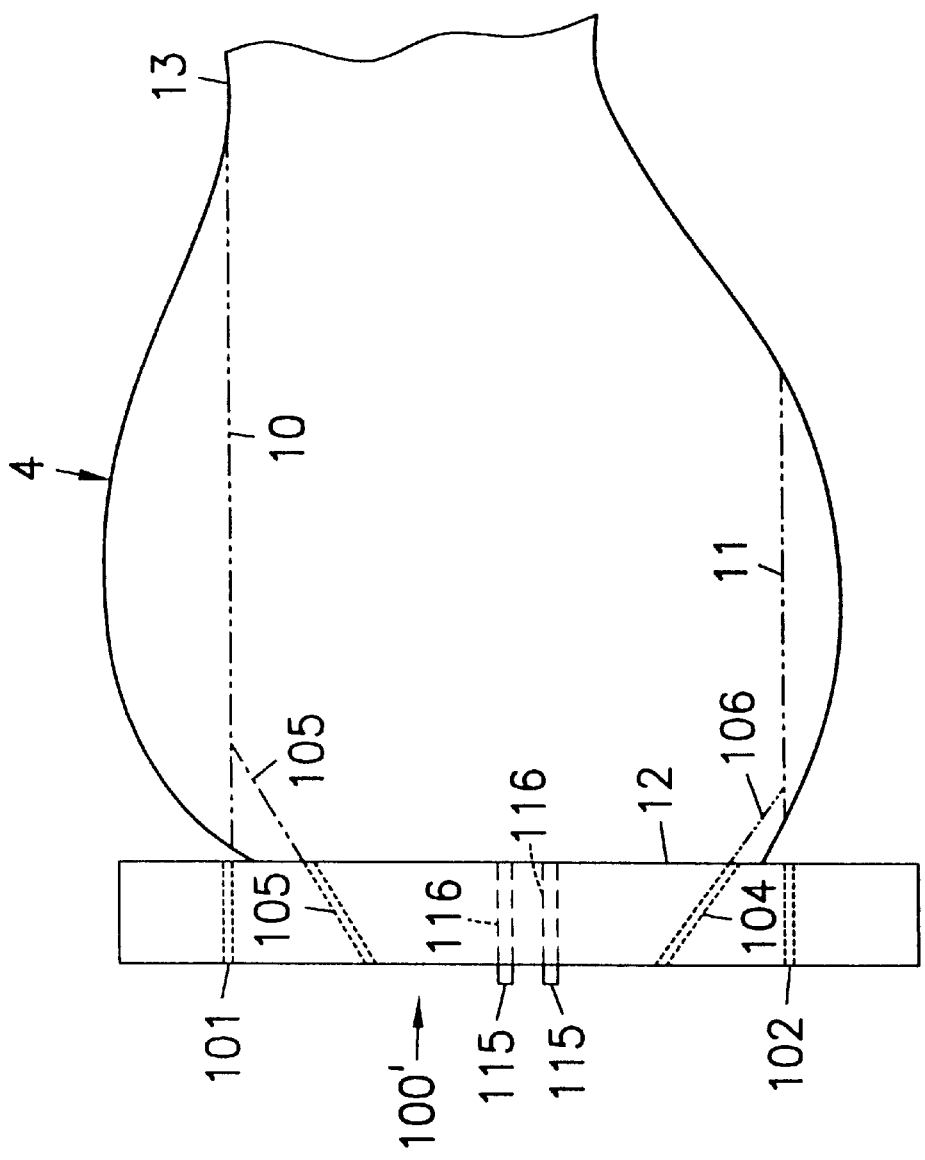
FIG. 20 is similar to FIG. 13 but shows a modification adapted to the embodiment of FIGS. 16 and 17.
Figure 21:
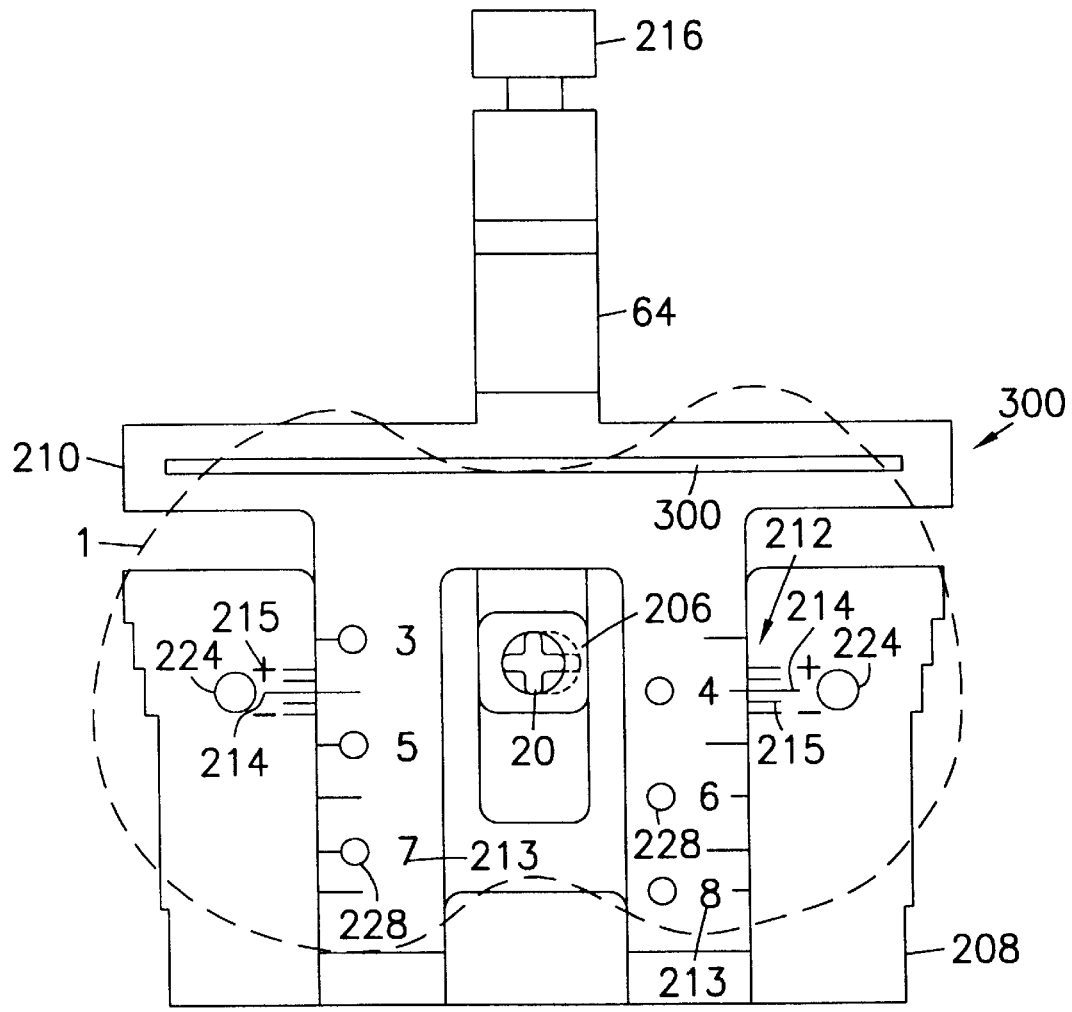
FIG. 21 is an end view similar to FIG. 6 of a fifth embodiment of the tool including an A-P measuring guide.

FIGS. 18 and 19 illustrate a fourth modified embodiment of the tool 30C which is a simplified version of the second embodiment of FIG. 14 and uses the same reference characters to designate like elements.

The tool 30C utilizes slider 34 which engages the rod end 24 and is slidably engaged in the legs 37 of the lower caliper half 35. The legs 37 of the lower caliper half 35 are slidably engaged with the legs 38 of the upper caliper half 36.

At its lower end, the lower caliper half 35 includes a cross bar 141 from which a leg 142 depends. The left 142 supports a pivot 143 which slidably rides in a slot 144 in a bracket 145 integral with posterior caliper plate 146. The posterior caliper plate 146 is similar to caliper plate 46 of the second embodiment and includes posterior caliper feelers for contacting the medial and lateral condyles 6 and 7. The slot 144 extends substantially parallel to the caliper plate 146 in the plane of tangential contact of the posterior feelers with the posterior surfaces of the medial and lateral condyles. An angle scale 147 is provided between the leg 142 and the bracket 145.

In the initial position of the tool, the slider 34 is fitted on the end 24 of the rod and the posterior feelers are brought into tangential contact with the medial and lateral condyles. The caliper means 35, 36 are rotated, while the rod 24 is held fixed, until the angle scale 147 reads zero. The pivot 143 is disposed in the slot 144 substantially in the plane T tangent to the posterior surfaces of the medial and lateral condyles. The tool 30C is then rotated to cause the end 24 to rotate through an angle A corresponding to the determined angle of rotation. The angle A is read on the angle scale 147. The pin 143 undergoes slidably movement in slot 144 while the slider 34 undergoes slidable movement in lower caliper half 35 to accommodate the rotation of the tool. The pin 144 remains in the tangential plane T. The scale 80 is a measure of the distance from the anterior feeler in contact with the anterior femoral cortex and the pin 143 along a perpendicular line from the anterior femoral cortex to a plane P passing through the pin 144 and inclined relative to posterior caliper plate 146 by the angle of rotation A of the tool. Any difference between the distance from pivot point 67 to the surface 68 of the sector plate 66 and the corresponding distance measured along the perpendicular to the incline plane P is negligible and even for an angle A of 12° the difference will be less than one-third mm.

As an alternative to the slot 144, the bracket 145 can be provided with a series of holes representing different angles of the caliper means 35, 36 relative to the plate 146, corresponding to different angles A, as in FIG. 14. The holes are provided along the axis of slot 144 in order to be in tangential plane T of the posterior feelers on the posterior surfaces of the condyles. When the pin 143 is secured in a respective hole the caliper means is secured at the angle designated by the associated hole. In the use of this alternative, with the tool not yet fitted on the end 24, the angle of the caliper means is set by inserting the pin 143 into the selected hole and the posterior feelers on plate 146 are brought into tangential contact with the condyles 6, 7. The tool is then fitted on the end 24 which now assumes the angle of the caliper means relative to the plate 146. The rod 20 is then driven into the femur 1 as before, or alternatively, as in the embodiment of FIGS. 16 and 17, pins 115 are installed in the condyles through holes in plates 110, 111 installed on the upper caliper half of the tool. The subsequent operations are the same as previously described.

FIGS. 21–33 illustrate a fifth modified embodiment of a tool 30D which is a simplified version of the first four embodiments of FIGS. 1–20 and wherein like reference characters are used to designate like elements. The tool 30D is specially adapted to be used in connection with a GENESIS II Total Knee System supplied by Smith & Nephew Richards, Inc. of Memphis, Tenn. It should be realized, however, that the tool 30D can be adapted to be used with knee systems of other manufacturers.

Figure 33:
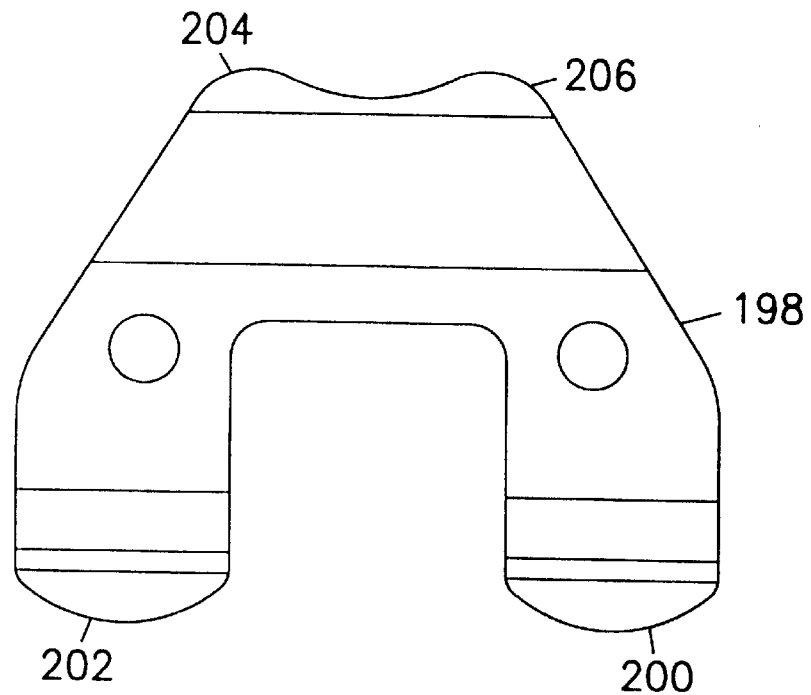
FIG. 33 is a front view of the preferred prosthesis to be used with the tool of FIG. 21.

Referring now to FIG. 33, there is shown a GENESIS II femoral prosthesis 198. The thickness of the distal femoral condyles of the prosthesis is about 9.5 mm (about 9–9.5 mm), i.e., the thickness of the distal medial femoral condyle 204 and the distal lateral femoral condyle 206 are about the same.

The prosthesis 198 has a 3° external rotation or varus angulation built therein. This is accomplished by altering the thickness of the femoral condyles posteriorly. For example, the thickness of the posterior lateral femoral condyle 200 of the prosthesis is about 3 mm thicker (about 2.5–3 mm) than the posterior femoral medial femoral condyle 202, assuming that the most prominent portions of the medial and lateral condyles are two inches apart. The difference of thickness of the posterior condyles of the prosthesis will vary directly with the distance between the condyles. The GENESIS II tibial prosthesis assembly, not shown, has a tibial baseplate (metal) thickness of about 2 mm and a tibial prosthesis (plastic) thickness of about 7.5 mm.

When using the tool 30D and the GENESIS II prosthesis 198, the joint line will be realigned parallel to the floor. This changes a normally 3° varus angle to 0°. A 3° angle amounts to approximately 1.5 mm per linear inch. Assuming the tibio femoral weight-bearing area is 2 inches apart on average, then 3 mm more laterally than medially must be resected from the tibia to achieve the resection parallel to the floor. To achieve a rectangular flexion and extension space, it follows that 3 mm more from the distal medial femoral condyle than the distal lateral femoral condyle must also be resected.

Referring now to FIGS. 21–33, once the bore 21 is formed longitudinally in the shaft 9 and in the condylar region 4 of the femur 1, the tool 30D is fitted over the rod 20 until it contacts the distal femur, i.e., the distal end of the femur 1. Before the tool 30D is fitted over the rod 20, the tool 30D is first fitted with a collet 206 which is similar to the stub 24. Like stub 24, collets having different angles varying about 5–7° may be provided and selection is made based on the anatomical condition and other conditions of the patient. The collet 206 is similar to the valgus angle bushing available from Smith & Nephew Richards, Inc.

The tool 30D is somewhat similar in structure to, but an improved version of, the valgus alignment guide and/or valgus alignment assembly available from Smith & Nephew Richards, Inc. The tool 30D includes a distal femoral sizer made up of a lower half 208 and an upper half 210 slidable in the lower half 208. When the distal femoral sizer is fitted with collet 206, collet 206 fixes the angle of the distal femoral sizer and may be referred to as a valgus alignment guide.

The lower half 208 includes a pair of posterior caliper feelers 47 for respectively contacting the posterior surfaces of the medial and lateral condyles. The caliper feelers 47 can be elongated to accommodate smaller and larger femurs, corresponding to prosthesis sizes 1–5 and 4–8 respectively.

The tool 30D includes a graduated scale 212. The graduated scale 212 includes markings 213 on the upper half 210 and a marker 214 on the lower half. The markings 213 on the graduated scale 212 indicate prosthetic sizes and hence is a measure of the distance D or S. For example, the markings 213 in FIG. 21 indicate prosthetic sizes 3–8. The upper half 210 can be adapted to indicate other prosthetic sizes as well.

Figure 34:
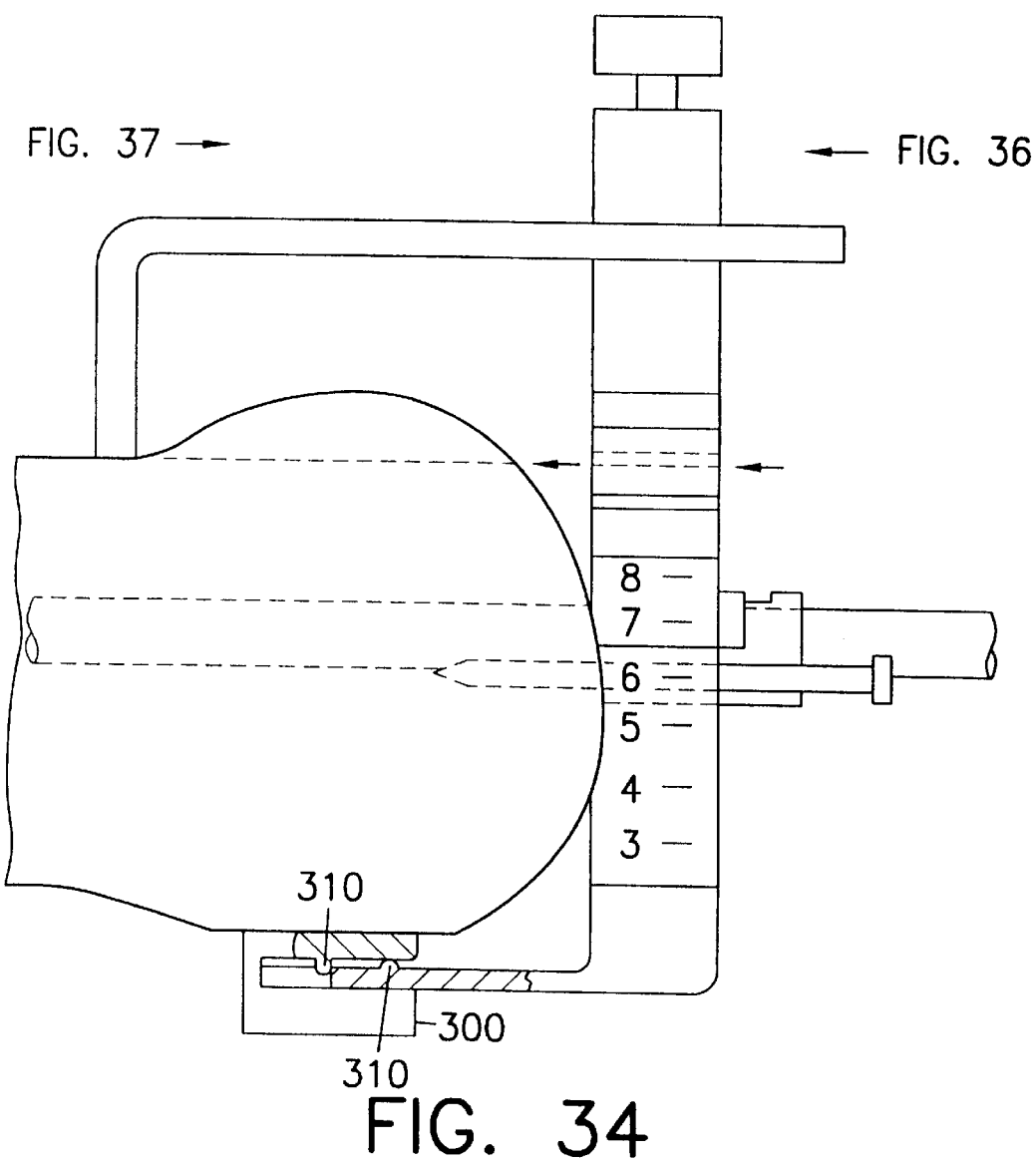
FIG. 34 is an alternative embodiment of the tool of FIG. 22, including posterior clips.
Figure 34A:
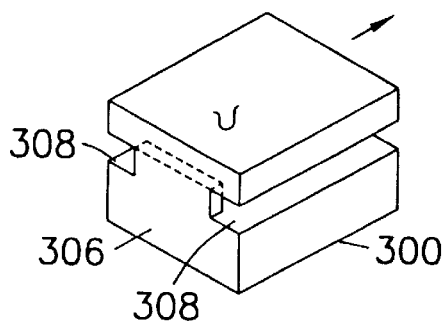
FIG. 34a is a rear perspective view of a posterior clip of FIG. 34.
Figure 34B:
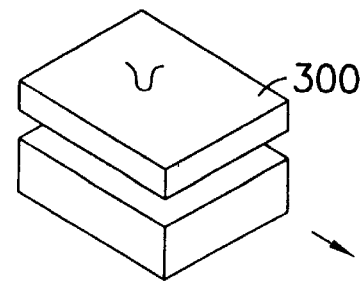
FIG. 34b is a front perspective view of a posterior clip of FIG. 34.
Figure 35:
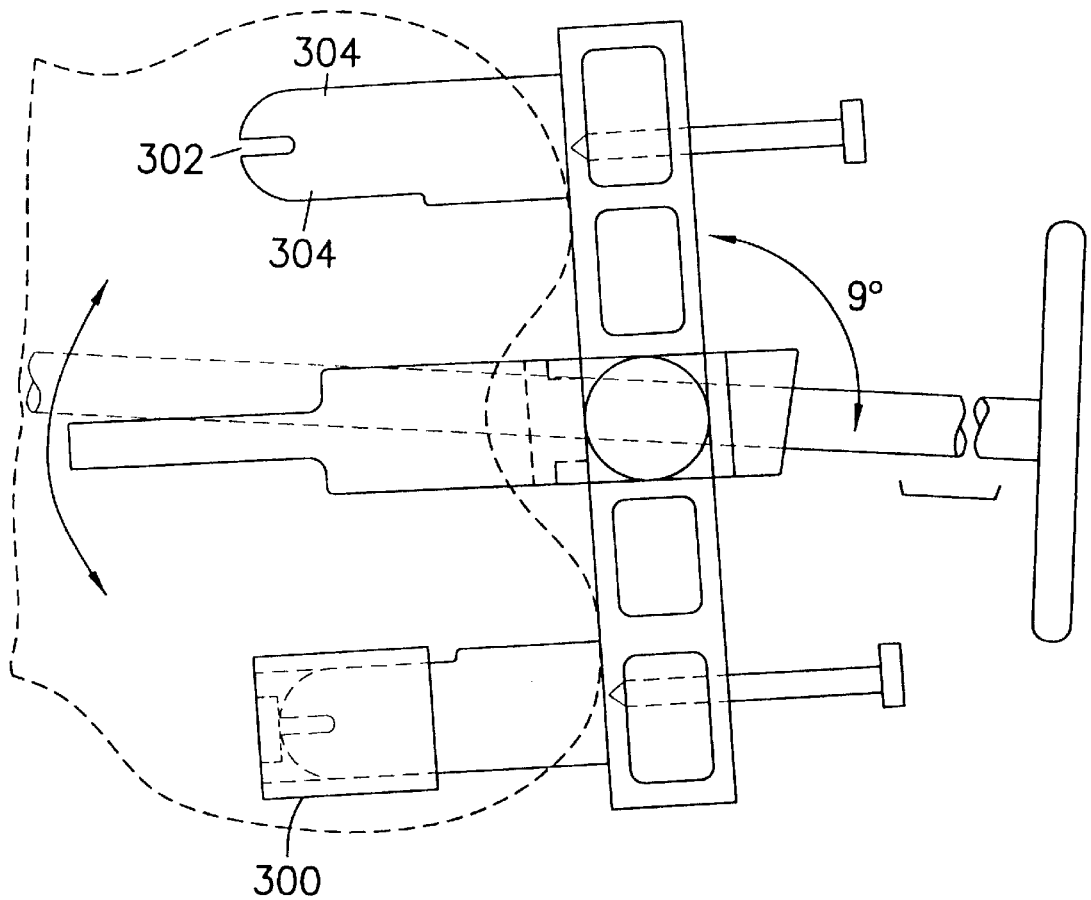
FIG. 35 is a top view of the tool of FIG. 34.
Figure 36:
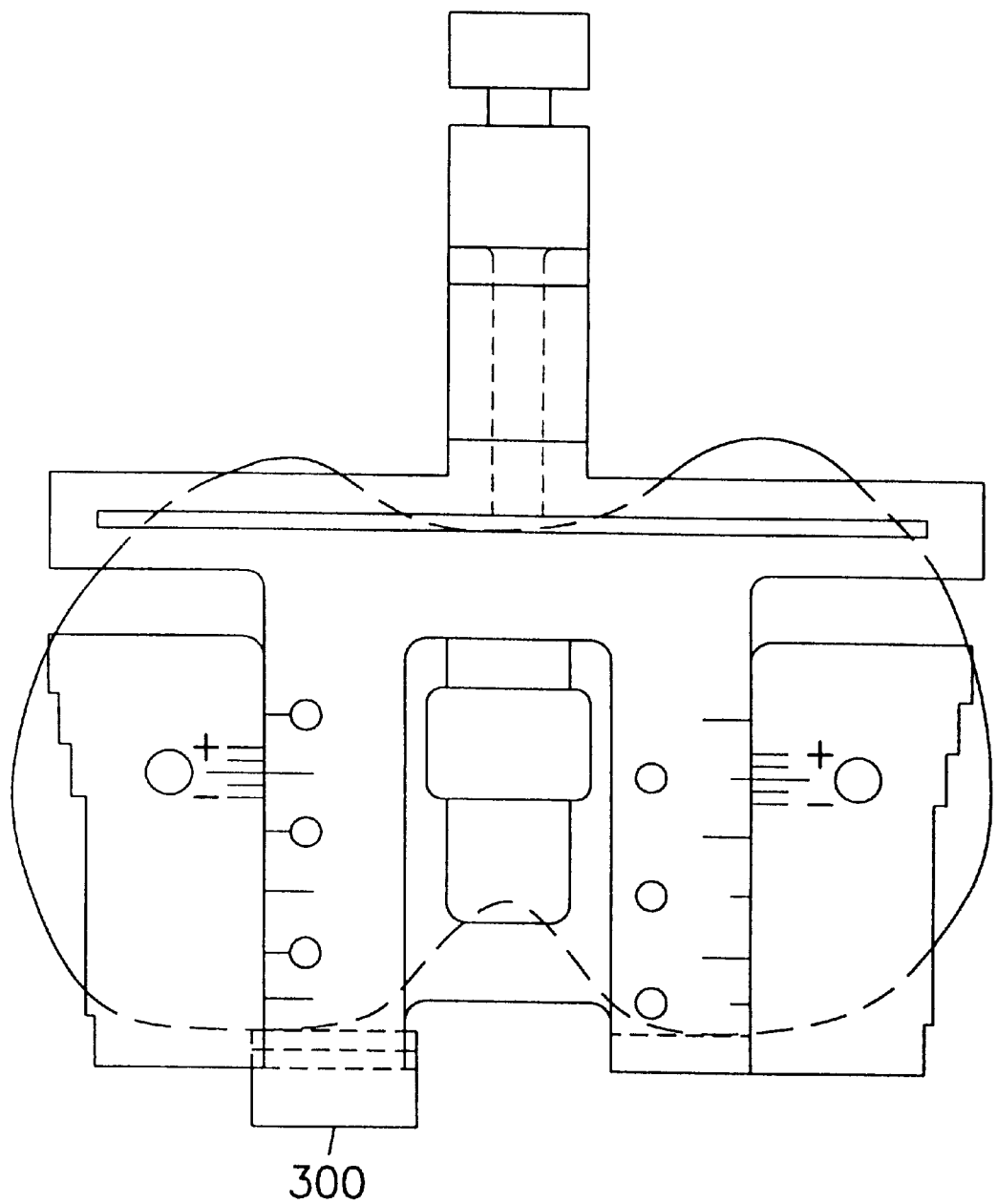
FIG. 36 is a front view of the tool of FIG. 34.
Figure 37:
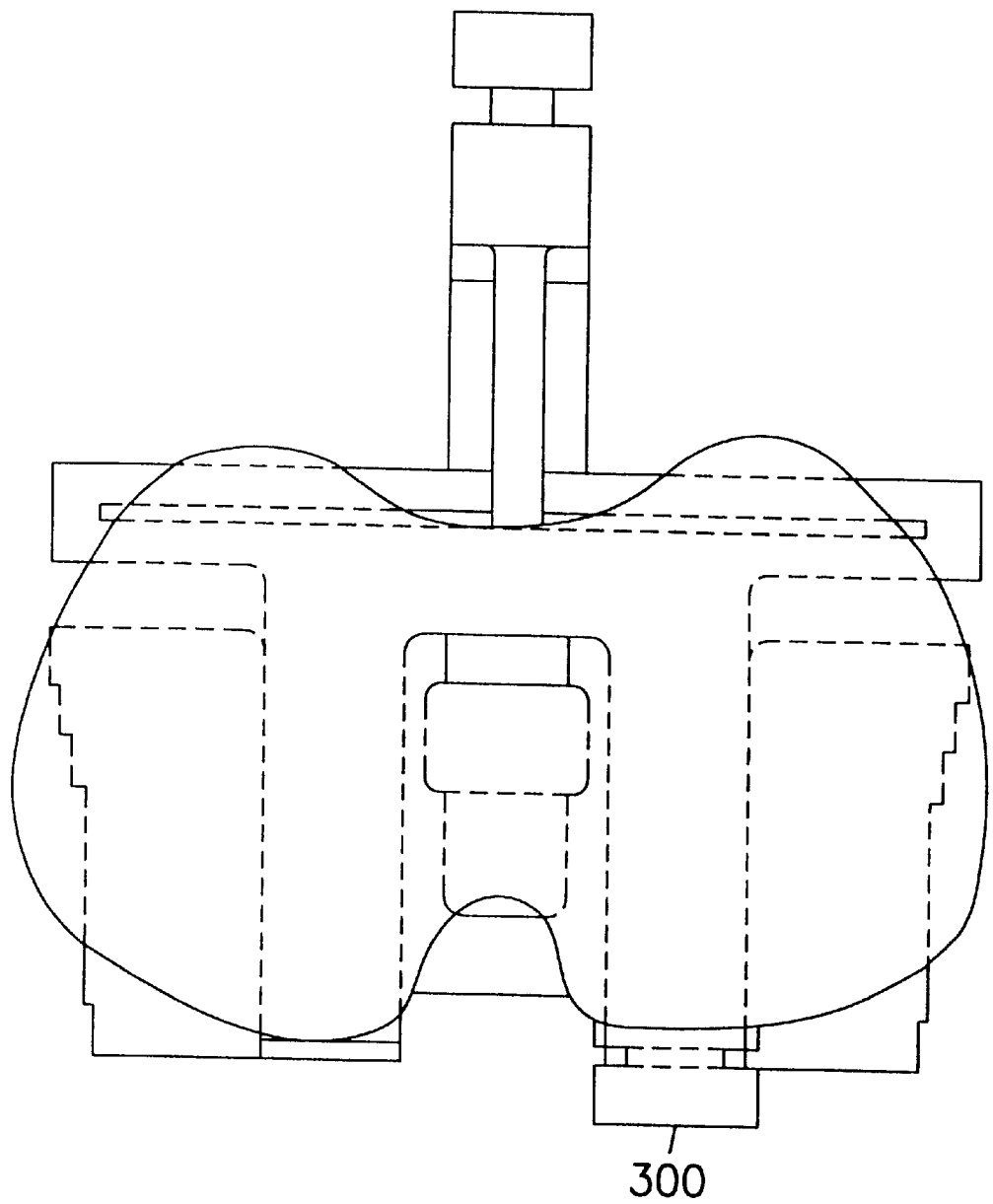
FIG. 37 is rear view of the tool of FIG. 34.

The lower half 208 includes scale 215 to indicate differences in size between respective prosthetic sizes, i.e., the number of millimeters over or under the prosthetic size. In a preferred embodiment, the scale 215 is calibrated in one millimeter increments. The calibration is such that when the marker 214 directly corresponds with a mark 213 on the scale 212 for a particular prosthesis, e.g., size 4, when this size 4 prosthesis is utilized, the difference between D and D' (the thickness $t_3$ resected at the posterior condyles and the distal femoral condyles) will be substantially equal to the thickness S (FIGS. 4 and 34) of the size 4 prosthesis to be inserted.

If the marker 214 falls between prosthesis markings 213 on scale 215, generally the smaller prosthesis size is selected and the resected thicknesses of the posterior condyles and the distal femur will be slightly increased accordingly. For example if the marker 214 falls one increment, i.e., one millimeter, beyond prosthesis size 4, then the resected thickness at the posterior condyles will be the average thickness of the posterior condyles of the size 4 prothesis (e.g., 19.5 mm) plus 1 mm. Similarly, the resected thickness of the distal femoral condyles may be electively increased 1 mm, i.e., 9.5 mm plus 1 mm.

It should be realized that if a surgeon were to choose the larger prosthesis, then the marker 214 and the scale 215 would indicate how much less thickness from the prosthetic size would be resected at the posterior and distal femoral condyles. In this case, appropriate compensation must be made on the distal femoral resection and possibly the proximal tibial resection depending on the deformity of the knee to achieve satisfactory motion and ligament balance.

The tool 30D includes an anterior-posterior (A-P) measuring guide or anterior caliper feeler 64 which along with the posterior caliper feelers 47 measure distance D'. The A-P measuring guide 64 includes a tab 216 which allows the A-P measuring guide to be releasably attached to the tool 30D.

The A-P measuring guide 64 is somewhat similar in structure to, but an improved version of, a femoral sizing guide available from Smith & Nephew Richards, Inc. The A-P measuring guide 64 includes a rod 63 and a sector plate 66 adapted to contact the anterior surface 13 of the femoral cortex. Unlike the tool 30 of the first preferred embodiment of FIGS. 1–3, the sector plate 66 need not be pivotally attached to the rod 63.

Figure 28:
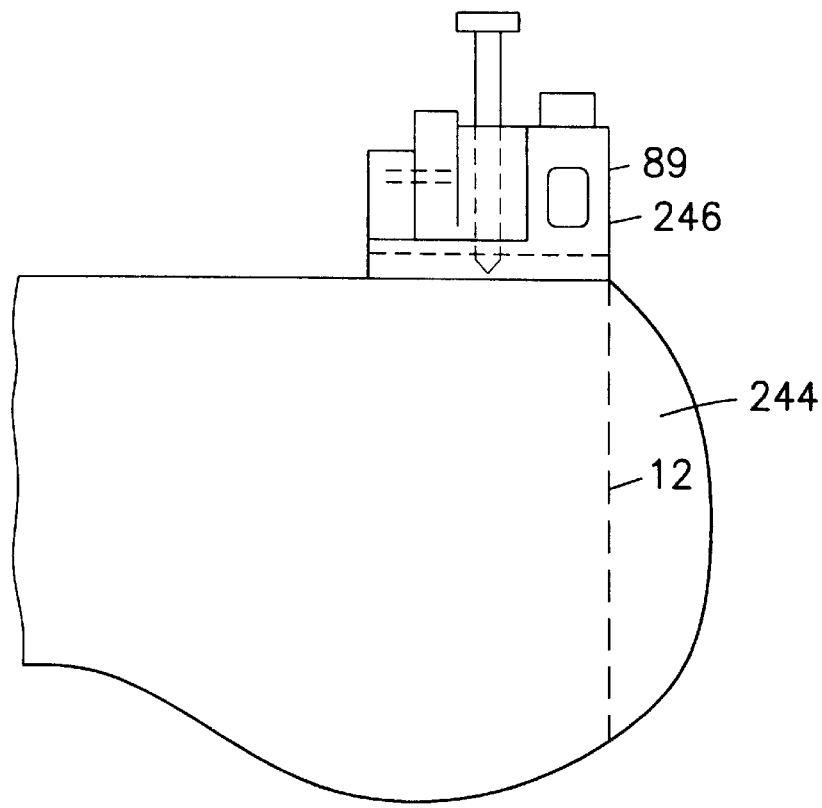
FIG. 28 is a side view of the femur with the distal cutting block mounted thereon.
Figure 32:
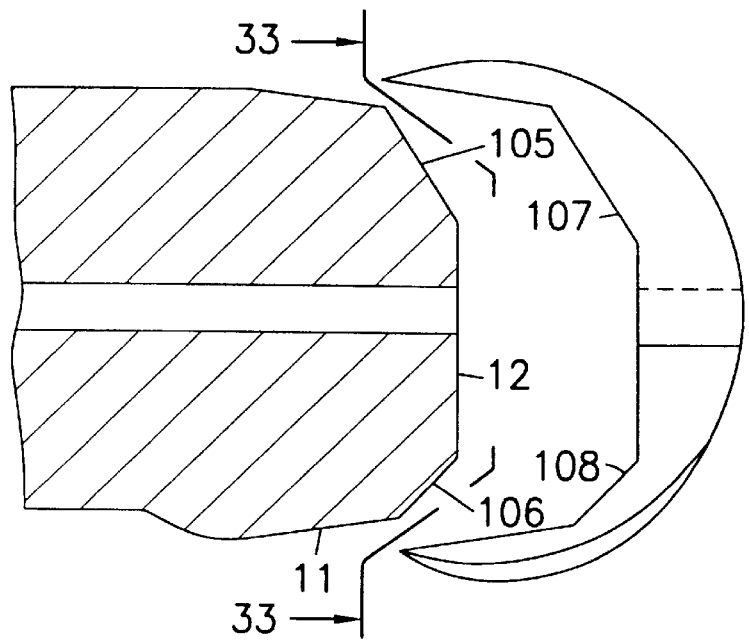
FIG. 32 is a side view of the distal end of a femur after it has been cut and a preferred prosthesis is ready to be mounted thereon.
Figure 29:
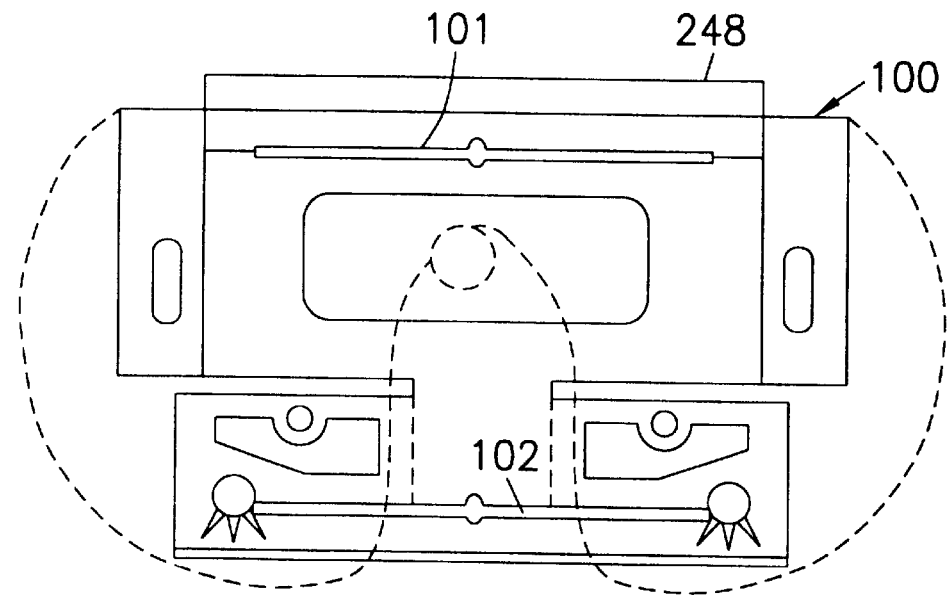
FIG. 29 is a top view of the A-P cutting block mounted on the distal femur.
Figure 30:
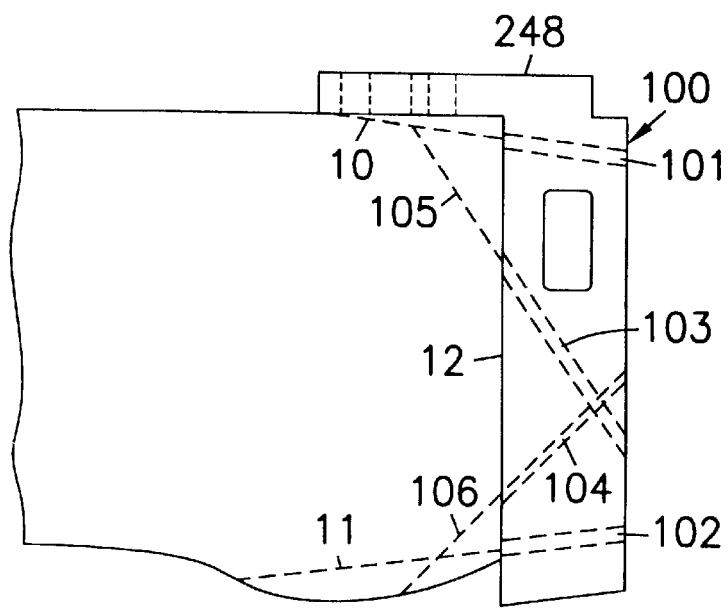
FIG. 30 is a view similar to FIG. 13 illustrating the distal end of the femur after the distal end has been cut and the A-P-cutting block has been mounted thereon.
Figure 31:
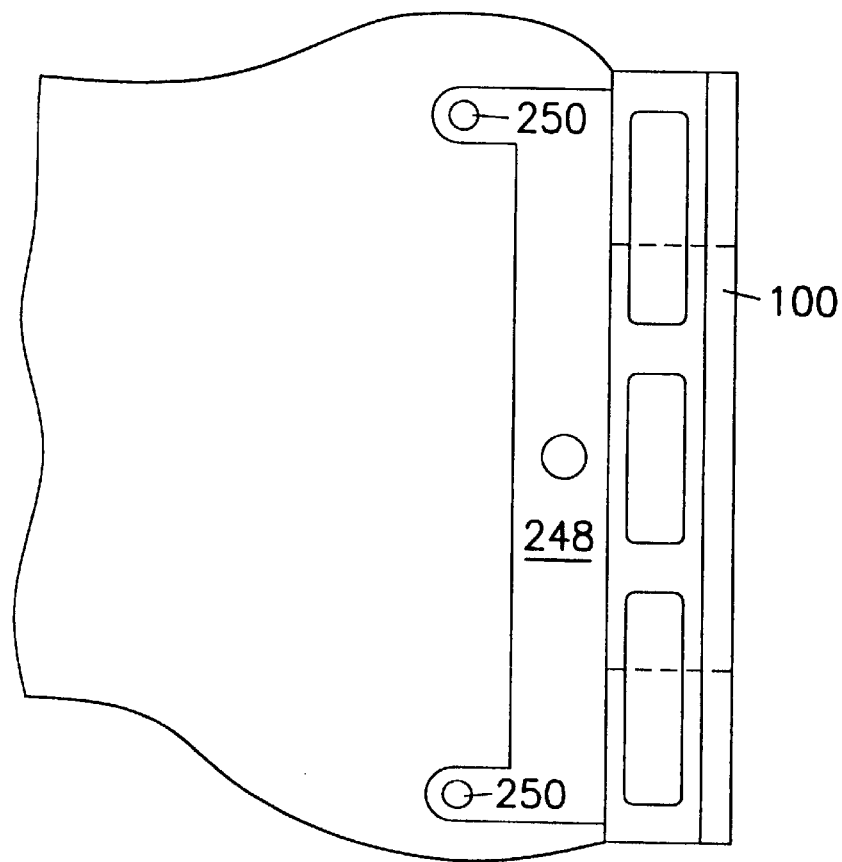
FIG. 31 is a top view of the A-P cutting block mounted on the distal end of the femur after the distal end has been cut and the A-P cutting block has been mounted thereon.
Figure 52:
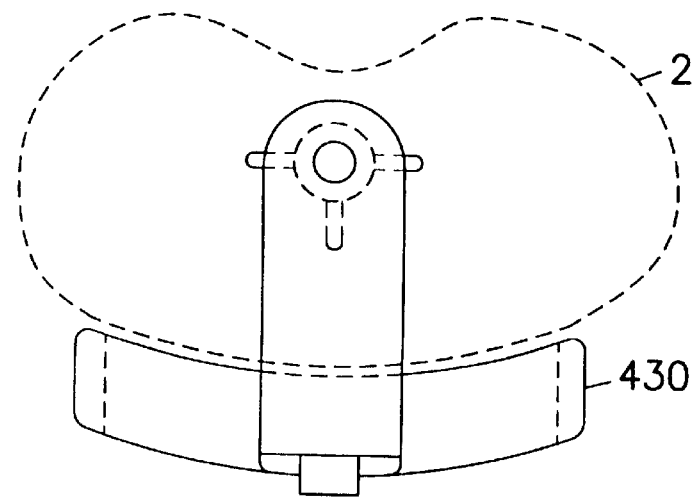
FIG. 52 is a top view of a tibial reresection guide of FIG. 50.

The tool 30D is also adapted to be used in connection with a distal femoral resection caliper 88, a distal femoral cutting block 89 (FIGS. 24–28) and an A-P cutting block 100 (FIGS. 29–31). The distal femoral cutting block 89 is used to resect the distal ends of the femur 1. The A-P cutting block 100 is used to resect the posterior medial and lateral condyles, to make the final anterior resection and to make the posterior and anterior chamfer resections as described above. The distal femoral cutting block 89 and the A-P cutting block 100 are somewhat similar in structure to, but an improved version of, the distal femoral resection stylus and cutting block, and the femoral A-P cutting block, respectively, available from Smith & Nephew Richards, Inc. Like the A-P measuring guide 64, the distal femoral cutting block 89 is releasably attached to tool 30D by tab 218.

Figure 26:
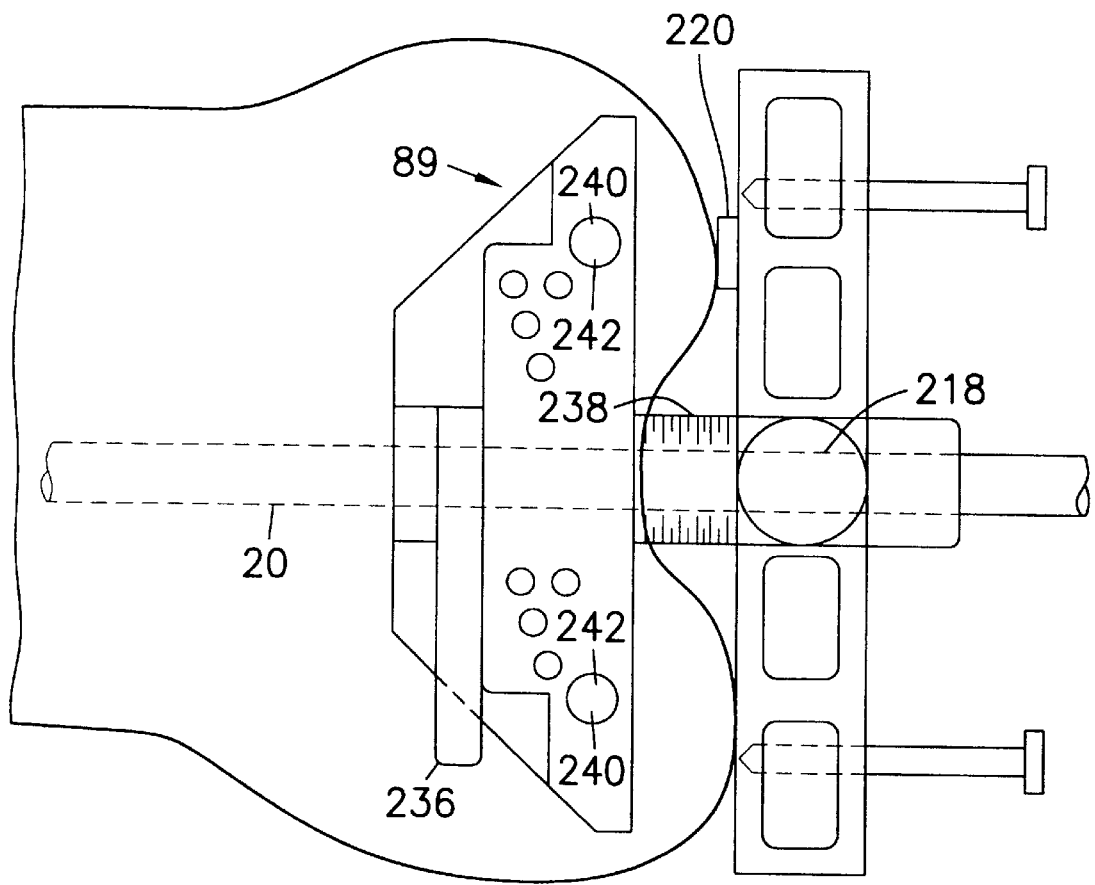
FIG. 26 is a top view of the tool of FIG. 25 mounted on the femur.

Referring now to FIGS. 21–33, in use, once the tool 30D with the properly angled collet 206 is fitted over the rod 20, which is inserted in the bone 21 of the femur 1, the tool 30D is made to contact the distal femur 1. As best seen in FIGS. 23 and 26, the side of tool 30D that contacts the distal femur 1 should include a 3 mm lateral offset 220 to contact the lateral surface of the distal femoral condyle. This ensures that the distal resection is substantially parallel to the proximal tibial resection in the medial lateral plane, and that the resultant distance between the tibial and femoral resections will be substantially equal to the thickness of the combined tibial and femoral prosthesis in flexion and extension.

In an alternative embodiment, if collet 206 is angled 8–10° instead of 5–7°, the 3 mm lateral offset 220 is not necessary. The 8–10° angulation is preferable because it reflects the true angulation of the distal femur.

Next, external rotation must be oriented from the posterior condyles (or any other consistent anatomic landmark). This requires adjustable posterior feelers or "feet" 47 to contact the posterior condyles at 3° of external rotation, or to be able to compensate for deformities and achieve posterior rotation.

To achieve the 3° external rotation, the tool 30D is then rotated so that the posterior caliper feelers 47 contact both corresponding posterior surfaces of the medial and lateral condyles (FIGS. 22 and 23) assuming equal or no bone substance loss. This sets the rotation or angle of the preliminary anterior resection 10 and the posterior resection 11 which is made by the A-P cutting block 100 (FIGS. 29–31), and equal amounts of substance will be resected from the medial and lateral posterior condyles. The rotation or angle of the posterior resection 11 is also set because an anterior portion 248 of the A-P cutting block 100 rests on the preliminary anterior resection 10 and thus sets the posterior resection 11 at the same rotation or angle as the anterior resection 10. Nails 222 should then be inserted in nail holes 224 to secure the lower half 208 to the distal femur.

If the posterior surfaces have unequal bone loss, the corresponding caliper feeler 47 should be made to contact the posterior surface with the least amount of bone loss. The tool 30D should then be rotated on the rod 20 so that the other caliper feeler 47 corresponding to the posterior condyle with the greater amount of bone loss is a distance away from that posterior condyle about equal to the amount of bone loss. This sets the rotation, or angle, of the preliminary anterior resection 10 and the posterior resection 11 which is made by the A-P cutting block 100 (FIGS. 29–31). Unequal amounts of substance will now be resected from the medial and lateral posterior condyles.

Referring now to FIGS. 34–38, in an alternative embodiment, clips 300 sized to make up for bone loss to the posterior condyles can be added to the posterior feelers 47. With clips 300, tool 30D does not need to be rotated as explained above to achieve the 3° external rotation. Preferably, clips 300 are made in 2, 4, 6, 10, and 12 mm sizes, although clip 300 can be made of any other appropriate size. The user of the tool 30D can estimate the amount of bone loss to the nearest clip size. In FIGS. 34–38, clip 300 is attached to the posterior feeler 47 corresponding to the medial posterior condyle because the medial posterior condyle suffered bone loss.

If both the medial and lateral condyles suffer bone loss, then the user of tool 30D uses the appropriately sized clip 300 based upon relative bone loss between the medial and lateral condyles. For example, if the medial posterior condyle suffers 6 mm bone loss and the lateral posterior condyle suffers 2 mm bone loss, then a 4 mm clip 300 will be attached to posterior feeler 47 corresponding to the medial posterior condyle.

The clips 300 can be attached to the posterior feelers 47 by any of the known methods. Preferably, posterior feelers 47 include a slot 302 and edges 304 which receive a tab 306 and grooves 308, respectively, formed in clip 300. Clips 300 may even include a spring activated post 310 or the like to secure clip 300 to posterior feelers 47 once slot 302 and edges 304 of the posterior feelers 47 receive tab 306 and grooves 308 of clip 300. Posterior feelers 47 may also include posts 310 to even more securely attach clips 300 to posterior feeler 47.

In the first preferred embodiment of the invention, the scale 71 should be set to rotate the sleeve 31 and thereby the rod 20 through angle A at 1° for every millimeter of bone loss. For example if the surgeon determines that there is 2 mm bone loss at one of the posterior condyles, the index marker should be set to correspond to a 2° angle or the angle scale 73. The sleeve 31 is then rotatable locked in the slider 34 and the rod 20 is driven in the bone 21 of the femur 1 to be angularly secured thereon in the desired rotational position relative to the plane T targeted to the portion surface of the medial and lateral condyles. See FIG. 9.

In order to set the caliper means in position to measure the distance D', the nuts 50 on pins 44 are loosened and the upper and lower caliper halves 36 and 37 are rotated as a unit around pin 44 at the lateral femoral condyle until the index marker 72 returns to its zero setting on the scale 73 as shown in FIG. 10. The nuts 50 are then tightened and the caliper halves are now in a position to measure distances perpendicular to the plane P tangent to the posterior surface of the lateral condyle.

In the fourth preferred embodiment of the invention, the tool 30C is rotated to cause the end 24 to rotate through angle A corresponding to the 2° angle of rotation. The angle A is read in the angle scale 147.

It should be realized that as explained above, if a prosthesis other than a GENESIS II prosthesis is used, i.e., a symmetrical prosthesis, the posterior condyles will be resected asymmetrically to reflect the 3° external rotation that was otherwise built into the GENESIS II prosthesis. This angulation may be greater than or less than 3° to compensate for any bone loss posteriorly.

Figure 22:
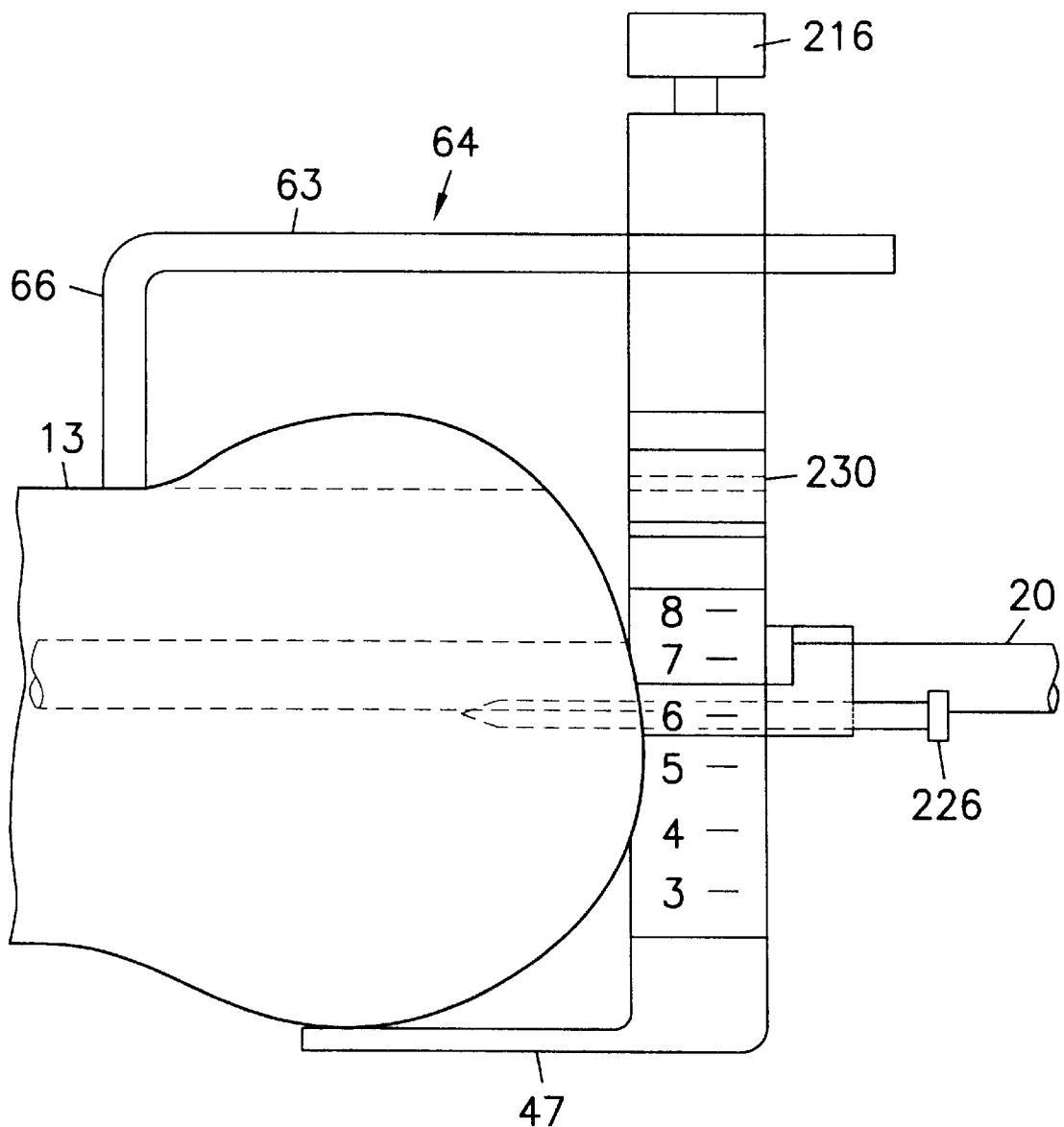
FIG. 22 is a side view similar to FIG. 5 of the tool of FIG. 21 mounted on the distal femur.
Figure 23:
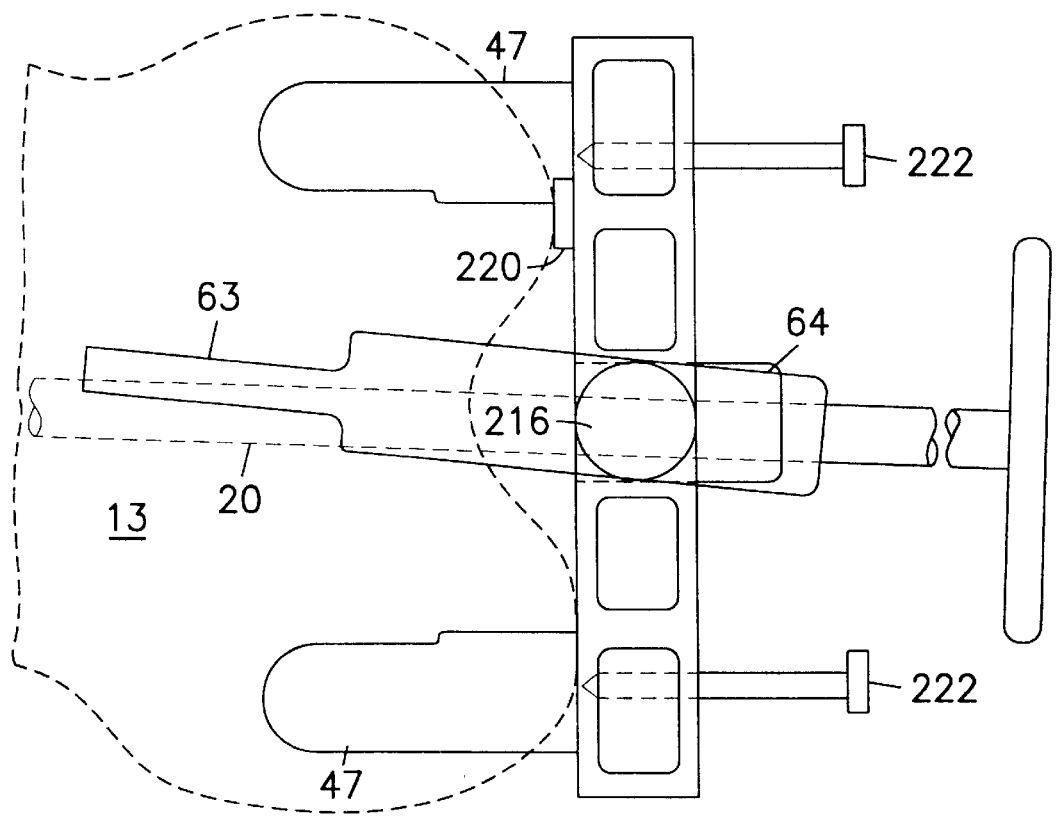
FIG. 23 is a top view of the tool of FIG. 21 mounted on the distal femur.
Figure 25:
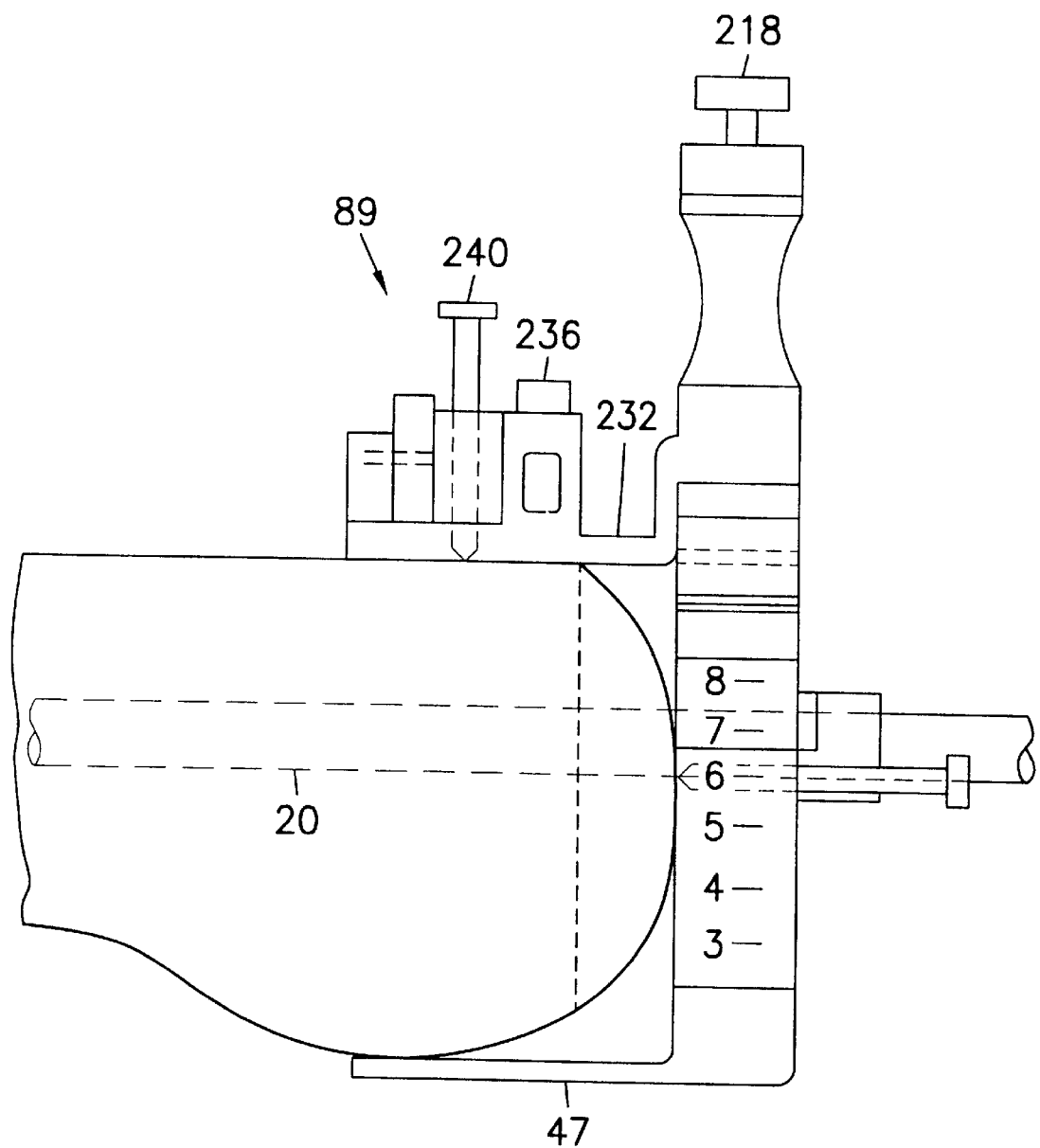
FIG. 25 is a side view of the tool of FIG. 21 mounted on the femur installed with the distal cutting block.

Referring back now to tool 30D, in order to set the caliper means in position to measure the distance D', the upper half 210 of the tool 30D fitted with the anterior caliper feeler 64 is then lowered until the sector plate 66 of the anterior caliper feeler 64 contacts the lateral portion of the anterior cortex, i.e., the sector plate 66 should contact the lateral side of the anterior cortex (FIGS. 22 and 23). The marker 214 then indicates a prostheses size S or distance D. If the marker 214 falls between two prosthetic sizes, normally the smaller prosthetic size is chosen. The upper half 210 is then fixed to the distal femur by inserting a nail 226 in the nail hole 228 that corresponds to the smaller chosen prosthetic size.

A measurement is now made to determine the appropriate size A-P cutting block 100 to later be used to resect the posterior medial and lateral condyles. The approximate size cutting block 100 corresponds to the chosen prosthetic size. If the marker 214 fell between two prosthetic sizes and the smaller size is chosen, i.e., anterior referencing, a measurement must be made to determine how many millimeters extra would be resected posteriorly (i.e., the thickness of the prosthesis posteriorly plus the number of mm over resection). This measurement is then taken from the scale 215 and is equal to the number of millimeters the marker 214 is away from the smaller prosthetic size. This measurement is then added to the average thickness of the posterior condyles of the prosthesis to determine the posterior resections. Each type of prosthesis has its own average thickness. For example, if the marker 214 indicates 1 mm greater than prosthetic 198 size 3, 1 mm extra will be resected posteriorly. The total posterior resection would then be the average thickness of the posterior condyles of the prosthesis 198 (e.g., 8.5 mm) plus 1 mm for a total thickness of 9.5 mm.

With the tool 30D still mounted on the rod 20, the anterior caliper feeler 64 is removed from the upper half 210 by depressing the tab 216. A saw blade, not shown, is then inserted into guides or slot 230 to make a preliminary cut of the anterior condyles to meet the surface of the anterior cortex in proper rotational alignment in the mediolateral plane.

The distal femoral cutting block 89 is then attached to the upper half 210 of tool 30D. Distal femoral resection caliper 88 is releasably attached to distal femoral cutting block 89 through a channel 234 fixed therein. Distal femoral resection caliper 88 is secured to distal femoral cutting block 89 by a cam mechanism 236 and to the upper half 210 by tab 218.

The distal femoral resection caliper 88 includes a sliding scale 238 that is calibrated at one millimeter increments from the average size or thickness of the distal femoral condyles of the prosthesis. The average size or thickness of the distal femoral condyles of a prosthesis ranges from about 6 mm to 12 mm depending on the particular prosthesis chosen. A typical thickness of the distal femoral condyles of prosthesis 198 is about 9.5 mm.

The distal femoral cutting block 89 should be inserted on the upper half 210 until it abuts the resected surface of the anterior cortex (FIG. 29). The cutting block should then be set at "size" plus (or minus) the previously taken measurement of how many extra (or fewer) millimeters would be resected posteriorly, i.e., 1 mm, at the surgeons discretion. "Size" equals the average of the expected resection of the medial and lateral distal femoral condyles. This equals 9.5 mm assuming normal anatomy. This will resect 11 mm from the distal medial femoral condyle and 8 mm from the distal lateral femoral condyle assuming a two inch distance between the two, i.e., the two most prominent portions of the distal femoral condyles.

The distal femoral cutting block 89 is then locked into place on sliding scale 238 by the cam mechanism 236. The distal femoral cutting block 89 is then secured to the anterior cortex by nails 240 through nail holes 242.

The rod 20 is then removed from the tool 30D. The cam mechanism 236 is disengaged and the distal femoral resection caliper 88 and the tool 30D should be removed from the distal femoral cutting block 89. only the distal femoral cutting block 89 should remain on the femur 1 (FIG. 28).

The distal femur should then be resected along the mediolateral plane 244 of the distal end 246 of the distal femoral cutting block 89. The preliminary anterior and final distal cuts 10 and 12, respectively, have now been made.

The plane 246 or cut 12 should be substantially parallel in the mediolateral plane to the proximal tibial resection, i.e., parallel to the floor, assuming normal ligament balance. If the ligaments are not normally balanced, then the ligaments should be released by any of the known methods until the planes are parallel in the mediolateral direction.

Figure 38:
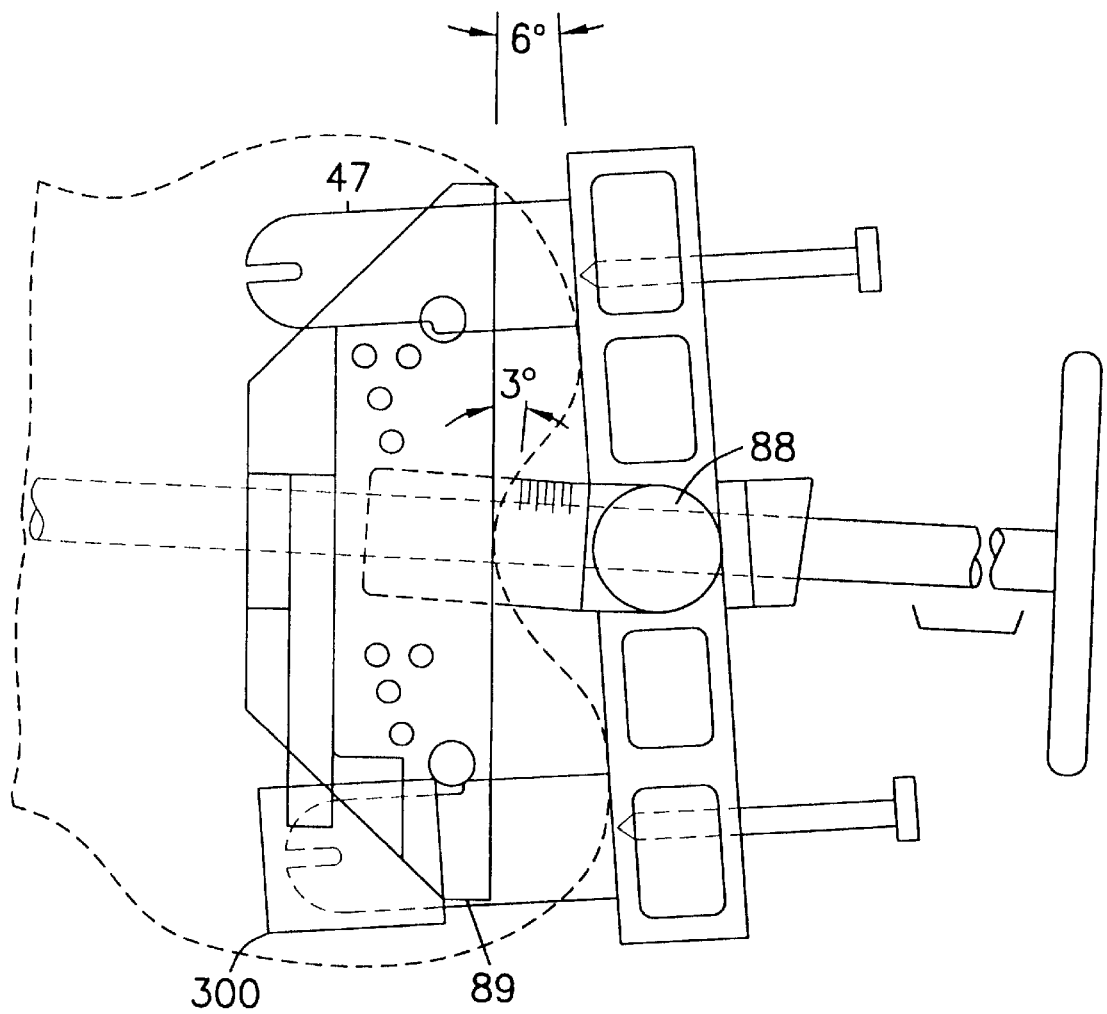
FIG. 38 is a top view of the tool of FIG. 34 mounted on the femur installed with a distal femoral cutting block and a distal femoral resection caliper.

Referring now to FIGS. 38–41 in an alternative embodiment, if collet 206 is angled 8–10° and the 3 mm lateral offset 220 is not used as explained above, distal femoral resection caliper 88 must compensate for the 3° increase in the angle of collet 206. Preferably, distal femoral resection caliper 88 compensates for the increase in the angle of collet 206 by itself being angled 3° as shown in FIGS. 38, 39, 41. For the left femur as shown in FIG. 38, distal femoral resection caliper 88 is angled 3° laterally as shown in FIG. 41 (i.e., follows the direction of the intramedullary rod). For the right femur, not shown, distal femur resection caliper 88 is angled 3° laterally as shown in FIG. 41 (and would also follow the direction of the intramedullary rod). The angulation of the distal femoral resection caliper 88 insures that the angle of the distal femoral resection corresponds to the medio-lateral plane of the tibial resection in a normal knee. Thus if one of the distal condyles suffers bone loss, the distal resection will remain at the proper level. In FIG. 38, there is shown a collet 206 angled 90°. Using distal femoral resection caliper 88 angled at 3° insures that the distal femoral resection is made 3° less, or 6°.

Referring now to FIGS. 29–32, the distal femoral cutting block 89 should be removed from the distal femur, and the appropriately sized A-P cutting block 100 should be inserted thereon. The A-P cutting block 100 is used to make the final anterior resection 10 and to resect the posterior surfaces of the medial and lateral condyles 11. If the flexion space is of concern, perform the preliminary anterior resection, distal femoral resection, and posterior condylar resection. Then test the flexion and extension spacing or "balance" with the appropriately-sized spaces before continuing.

The A-P cutting block 100 is placed onto the distal femur secured by angled nails through the sides of the cutting block 100, not shown. The A-P cutting block 100 includes an anterior portion 248 that sits flush with the anterior cortex of the femur 1. If desired, the A-P cutting block 100 can also be secured to the distal femur by nails (not shown) in nail holes 250). The A-P cutting block 100 should now sit flush with the cut anterior surface 10 and the distal surface 12.

The A-P cutting block 100 includes slots 102 and 101 which are precisely placed for guiding a resector or cutting blade to produce the final posterior and anterior cuts 11, 10 respectively. Because of the asymmetric buildup of metal on the posterior condyles of the GENESIS II femoral prosthesis 198, e.g., about 2.5–3 mm thicker on the posterior lateral condyle, the posterior femoral resection 11 must be altered to accommodate this difference. The resultant posterior femoral condylar joint line should be parallel to the resultant tibial joint line, i.e., parallel to the floor.

The posterior femoral resection 11 should be approximately 3° of varus in the mediolateral plane referenced from the horizontal assuming no wear or equal wear posteriorly. The A-P cutting block 100 assures this due to its alignment with the preliminary anterior femoral condyle resection 10.

The A-P cutting block 100 is so aligned because the anterior portion 248 rests on the preliminary anterior cut 10 which has already been resected at the desired rotation or angle. The posterior condylar resection will be equal posterior medially and posterior laterally assuming no wear or equal wear of the posterior condyles. Moreover, the posterior cut 11 will be made in a constant relationship, e.g., diverge 3 degrees, from the proximal tibial resection. In other words there will be an opening wedge laterally.

As explained above, if there is no or equal wear, then tool 30D would have been rotated appropriately to account for the asymmetric loss of substance. The posterior resections will not be equal posterior medially and laterally under this circumstance.

The A-P cutting block 100 also includes angular slots 103 and 104 to form chamfer cuts 105, 106 which also match corresponding angular surfaces 107, 108 on the prosthesis 198. Preferably, the femur 1 should be resected in the following order: the posterior resection 11, the posterior chamfer 106, the final anterior resection 10 and the anterior chamfer 105. The A-P cutting block 100 is then removed and the prothesis 198 is installed on the distal femur by any of the known methods.

As shown above, since the prosthetic femoral condylar dimensions were 9.5 mm distally and posteriorly, a "standard" resection would be set to resect 11 mm from the distal medial and posteromedial condyles, and 8 mm from the distal lateral and posterolateral condyles. This would then produce a 9.5 mm resection at the midline. When combined with the tibial resection, explained below, this would give a 19 mm rectangular space to receive the prosthetic components.

Preferably, the instrument system of the present invention is for femoral resection and replacement, tibial resection and replacement and patellar resection and replacement, i.e., a total knee replacement system. Preferably, in the total knee replacement system of the present invention, the tibia is resected before the femur and the tibia then reresected, if necessary, to properly articulate the tibial and femoral prosthesis. It should be realized, however, by those skilled in the art that the tibia and femur can be resected and replaced in any order.

Figure 44:
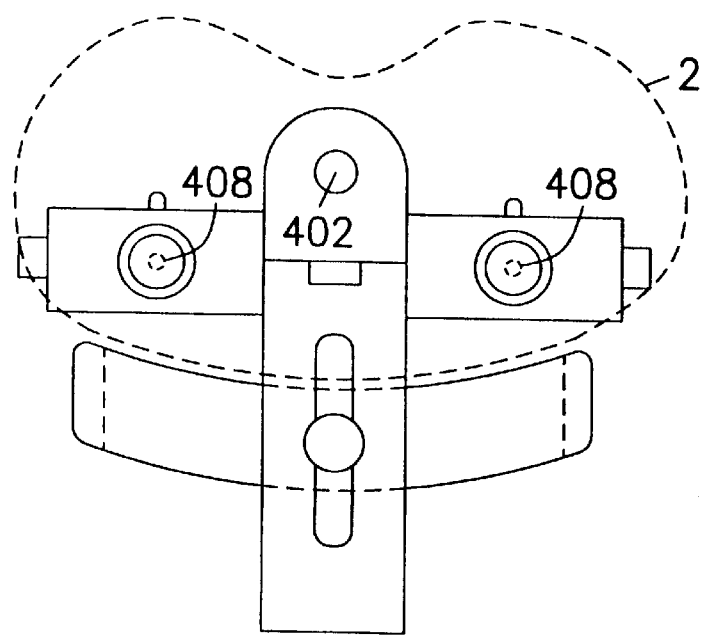
FIG. 44 is a top view of the tibial resection guide of FIG. 42.
Figure 42:
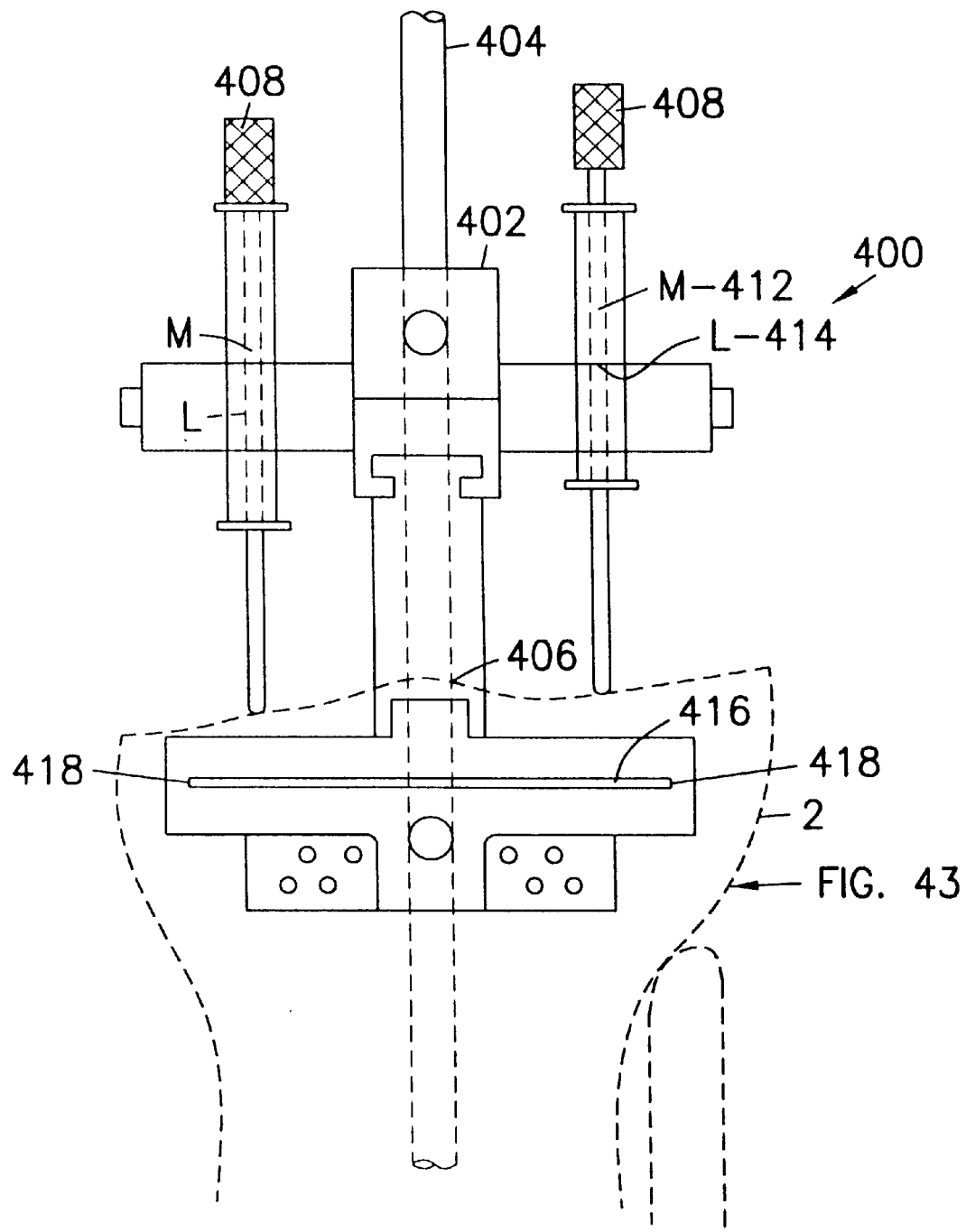
FIG. 42. is a front view of a tibial resection guide of the present invention mounted on a tibia.
Figure 43:
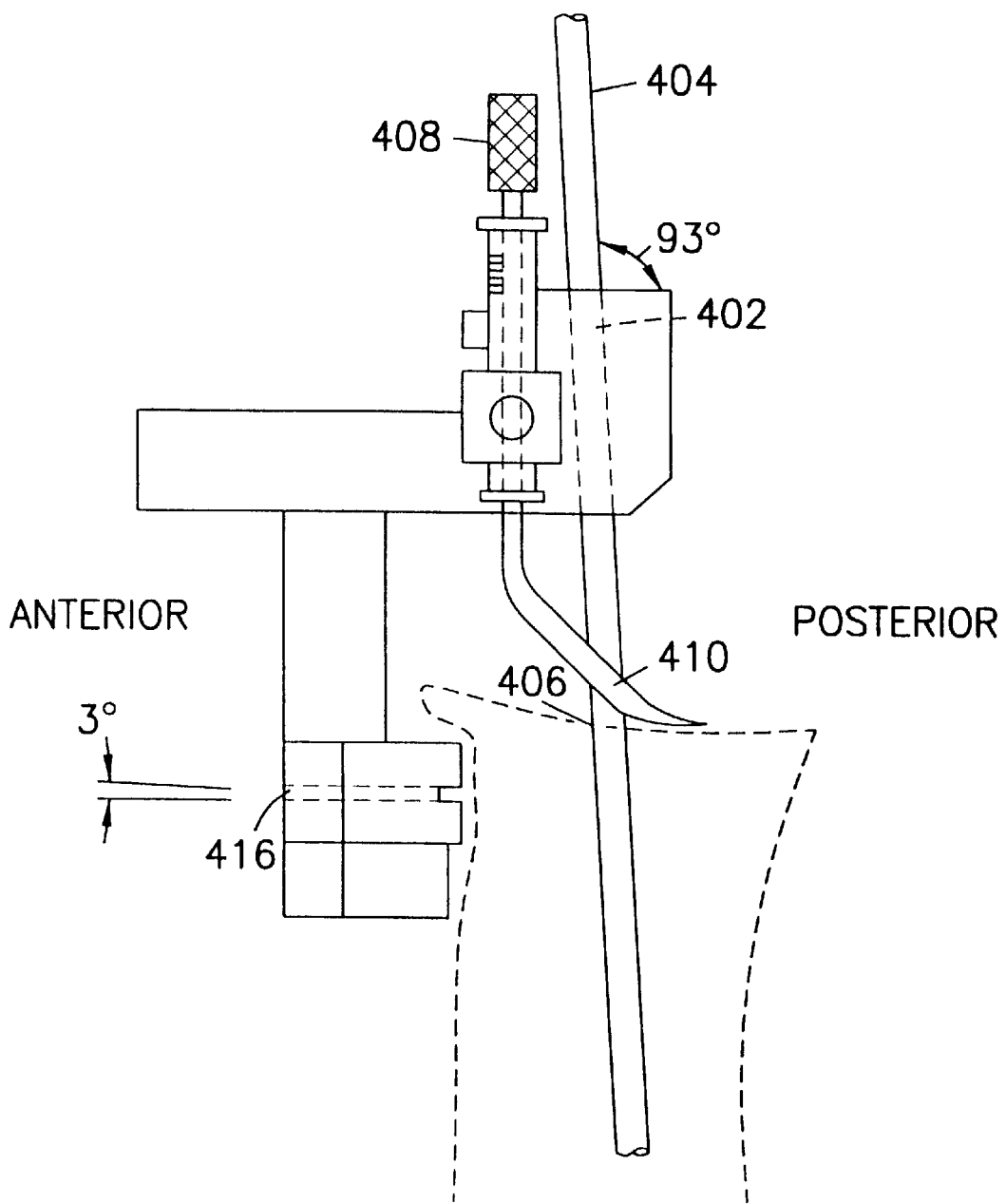
FIG. 43 is a side view of the tibial resection guide of FIG. 42.

Referring now to FIGS. 42–44, there is shown a tibial resection guide 400 of the present invention mounted on tibia 2. Tibial resection guide 400 is similar to, but an improved version of, the tibial alignment assembly marketed by Smith & Nephew Richards, Inc., in Memphis, Tenn. under the PROFIX® total knee system and adapted to GENESIS II prosthetic dimensions and specifications.

Tibial resection guide 400 includes a bore 402 for receiving a reamer rod 404 therethrough. Bore 402 is drilled in tibial resection guide 400 at a 3° posterior tilt, i.e. tilted down from the anterior to posterior, or down from the horizontal, 3°. Tibial resection guide 400 is mounted on tibia 2 by any of the known methods.

Initially, the knee should be exposed in the standard fashion exerting the patella. The anterior cruciate ligament should be released. If the PCL must be released, release it now. Remove the medial osteophytes. Preferably, using a standard femoral drill, e.g., ⅜", the proximal tibial medullary canal 406 is opened just posterior to the tibial attachment of the anterior cruciate ligament. An intramedullary or reamer rod 402 is then placed in the drilled tibial shaft just anterior to and between the tibial spines by any of the known methods.

Tibial resection guide 400 is mounted on rod 404 in the manner shown in FIGS. 42–44. Tibial resection guide 400 includes a pair of styluses 408 rotatable in tibial resection guide 400. Preferably, the styluses are spaced about 2 inches apart. Styluses 408 are independently rotatable so they can contact the highest, or the most intact side, of the tibial plateau. Styluses 408 include angled or curved foot extensions 410. Preferably foot extensions 410 are angled so they extend approximately 3–4 mm further posterially than reamer rod 404.

Once a stylus 408 is made to contact the most intact or highest point on the tibial plateau, that particular stylus 408 remains stationary while tibial resection guide 400 is moved up or down rod 404 until it coincides with "M" marking 412 if the most intact side is the medial side, or with "L" marking 414 if the most intact side is the lateral side. It is not necessary to use both styluses. Tibial resection guide 400 is then secured in that position by for example tightening a sliding screw. The markings 412, 414 set the proper tibial resection. Preferably, for a tibial prosthesis 9.5 mm thick, the proper resection corresponding to the "L" marking 414 is 11 mm and 8 mm for the "M" marking 412, thus representing a 3 mm difference between the markings, assuming the styluses are two inches apart. One millimeter or more markings can be utilized therebetween. For prostheses with differing thicknesses, the resection lengths for the markings 412, 414 are adjusted taking into account that the tibial plateau varies approximately 1.5 mm per inch. Thus, the thickness of the prosthesis, e.g., 9.5 mm, should represent an average thickness between the medial lateral resection, namely 8 mm and 11 mm, respectively.

Tibial resection guide 400 is now in the proper position to remove the desired amount of bone described above, i.e., resect at 8 mm medially or 11 mm laterally. At this time it is preferable to protect the posterior cruciate ligament (PCL) if still intact.

To resect the bone, a resector is inserted through slot 416 by any of the known methods. Because of the 3+ proximal medio-lateral varus tilt of the tibia, the bone is resected on a 3° valgus medio-lateral tilt relative to the tibial plateau. Regardless of the tilt, using either an intramedullary or extramedullary rod, the resection of the tibial plateau in the medio-lateral plane must be parallel to the floor.

Referring now to FIG. 43, because bore 402 is drilled in tibial resection guide 400 at a 3° posterior tilt, i.e. tilted down from the anterior side to the posterior side 3°, tibia 2 is resected 3° down from the horizontal, i.e., tilted higher anteriorally than posteriorly.

Preferably, slot 416 of tibial resection guide 400 extends through most of its width, and does not include a stop in the center like tibial resection apparatus of the prior art. Without such a center stop, better access is afforded to the tibia.

In a preferred embodiment, tibial resection guide 400 includes stops 418 at the ends thereof. Stops 418 protect the patellar tendon and the medial and lateral ligaments.

Figure 45:
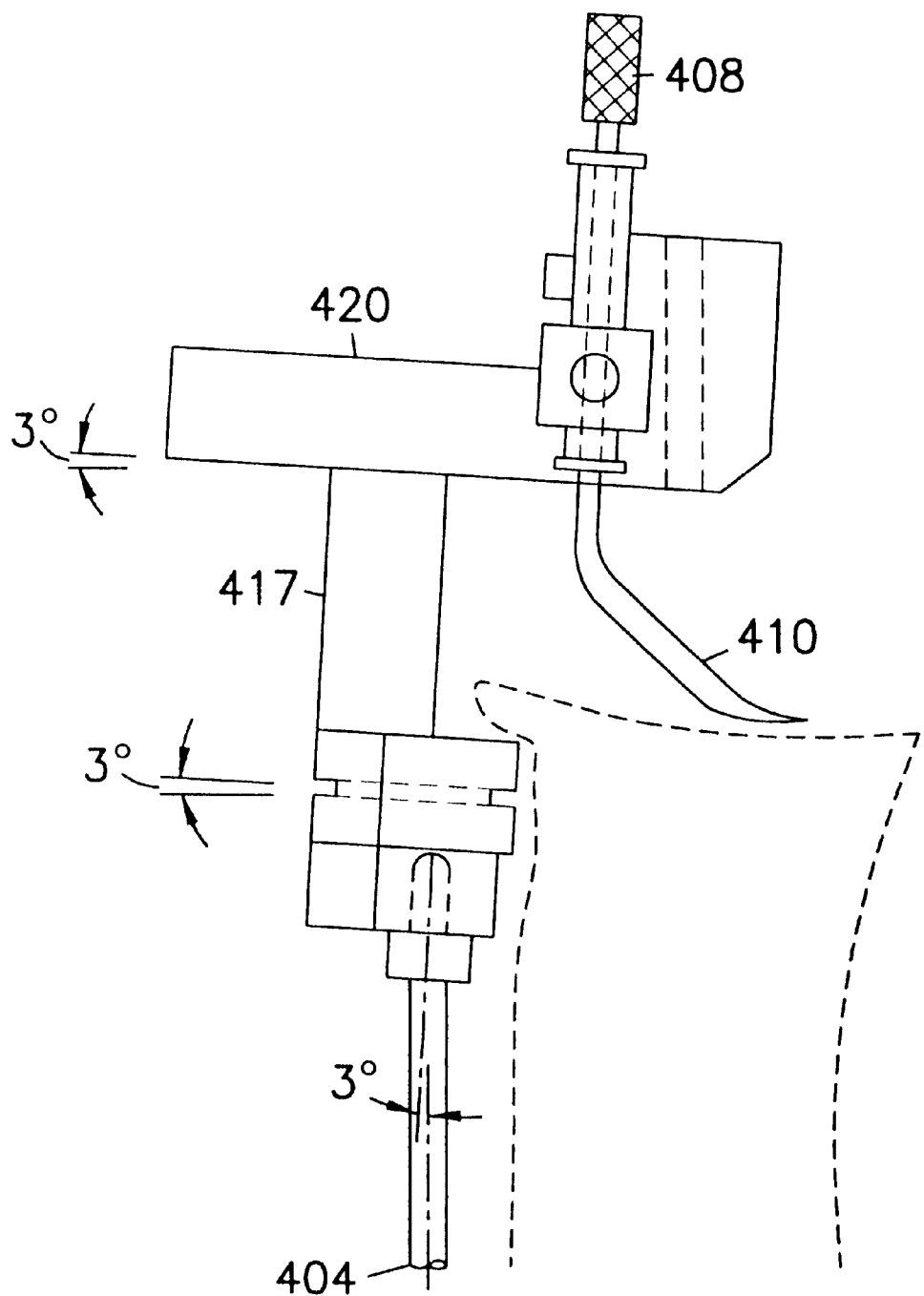
FIG. 45 is a side view of a tibial external resection guide of the present invention mounted on a tibia.

Referring now to FIG. 45 there is shown an alternative embodiment to the present invention. FIG. 45 shows a tibial external alignment guide 420. Preferably, rod 404 should be angled 3° to account for the 3° posterior tilt bored into tibial resection guide 400 as explained above. Tibial external alignment guide 420 is otherwise constructed, and resects tibia 2, in the same way as tibial resection guide 400.

Now that tibia 2 and preferably femur 1 have been resected, tibial secondary finishing apparatus is employed to achieve a properly articulated knee in flexion and extension. For example, tibial resection guide 422, FIG. 50, can be used to downsize tibia 2, versus downsizing femur 1, to gain increased flexion if the knee is tight following the femoral and tibial resections.

Referring now to FIGS. 46–47, there is shown spacer apparatus which is used to check the space between the tibial and femoral surfaces in flexion and extension after the appropriate femoral and tibial resections. The spacer apparatus is typically necessary only in cases where the spacing is put in question, e.g., where the knee has a complex deformity or a severe loss of motion. The goal is to cut off the least amount of bone and have proper ligament balance medially and laterally in flexion and extension. The ligament balance should be solid in extension and slightly loose in flexion. The spacer apparatus is advantageous because it determines how much additional bone to resect before the bone is actually resected.

Referring now to FIG. 46, spacer apparatus includes paddle 424 having an extension spacer 426 and a flexion spacer 428 located at opposite ends thereof. As shown in FIG. 46A, flexion spacer 428 tapers from 10.5 to 7 mm in thickness. As shown in FIG. 46B, extension spacer 426 is uniformly 7 mm thick.

Paddle 424 can be used in connection with snap-on spacers, not shown, which are available from any of the know suppliers and can be secured to paddle 424 by any of the known methods. The snap-on spacers are used to increase the thickness of extension and flexion spacers 426, 428. The snap-on spacers come in sizes of 2–16 mm, and typically are available in 2 mm increments, e.g., 2, 4, 6 mm etc.

Heretofore paddles of the prior art had extension spacers 19 mm thick and flexion spacers that tapered from 19–20 mm in thickness. These paddles are disadvantageous because they can not be used in spaces less than 19 mm thick.

Paddle 424 and snap-on spacers are used in accordance with known methods to ensure a properly articulated knee in flexion and extension and proper ligament balance.

Figure 50:
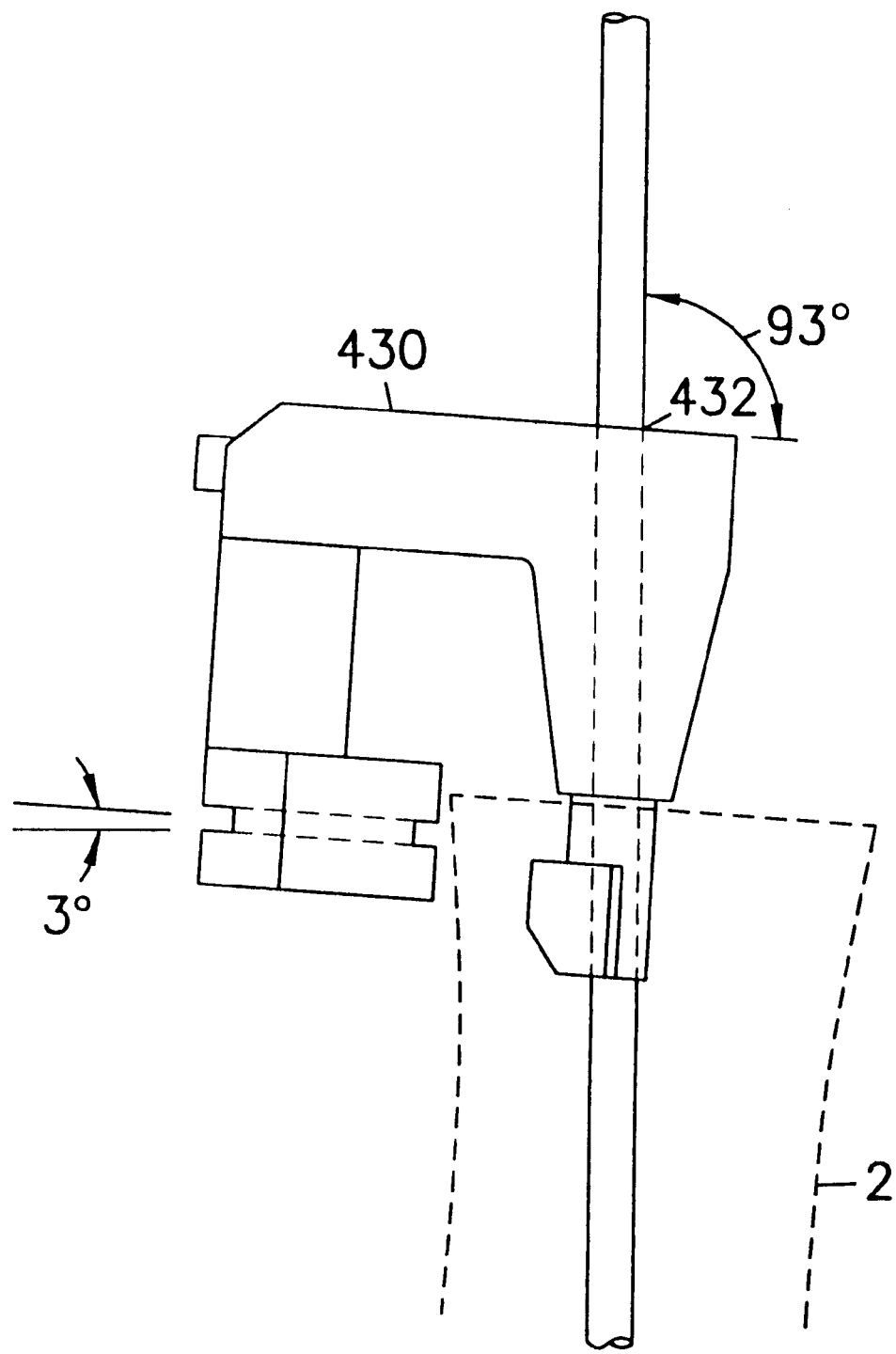
FIG. 50 is a side view of a tibial reresection guide in accordance with the present invention mounted on a tibia.
Figure 51:
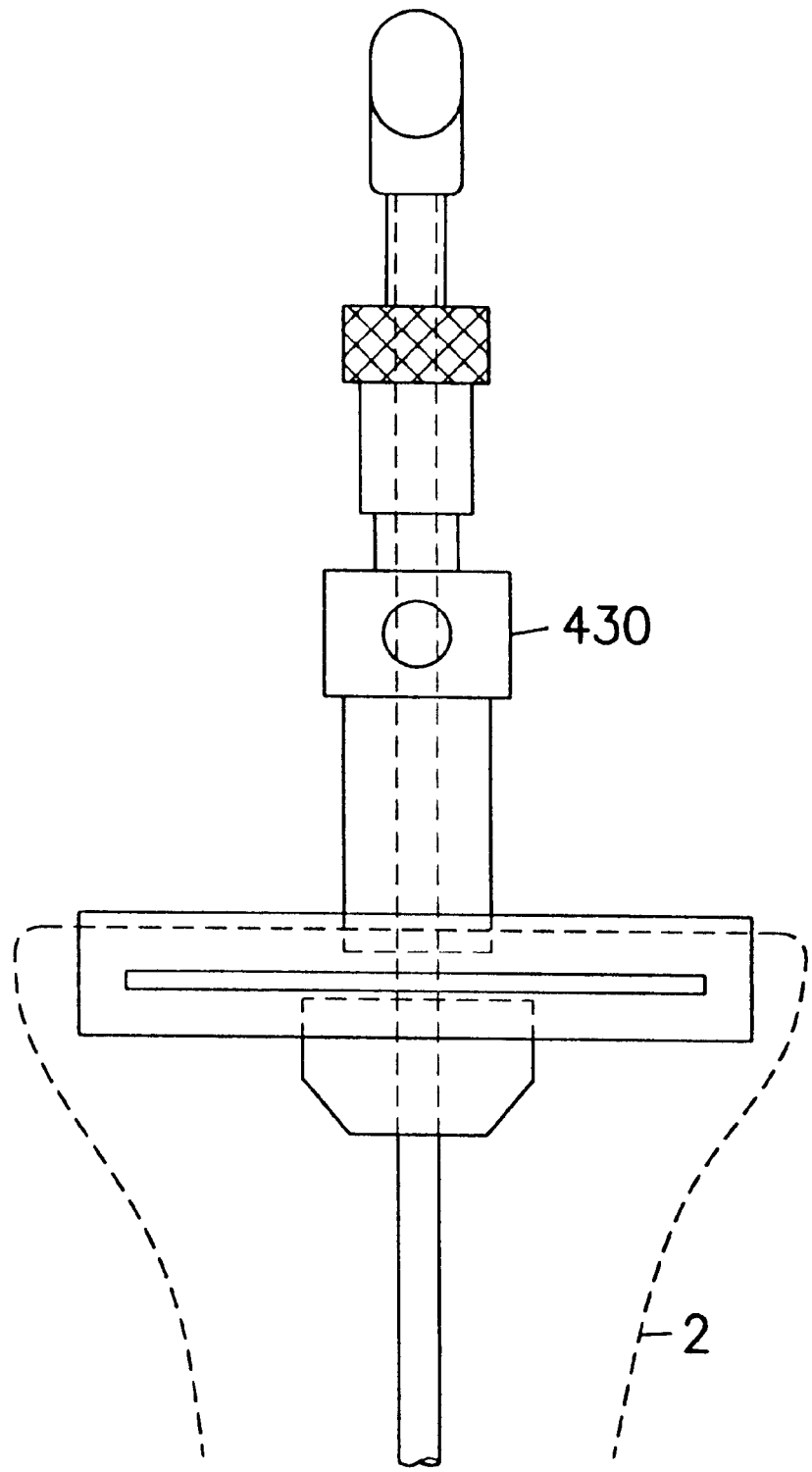
FIG. 51 is a front view of the tibial reresection guide of FIG. 50.

Referring now to FIG. 50, there is shown a tibial reresection guide 430 that is used to take additional bone off of tibia 2 if, for example, this is found to be necessary as a result of using the spacer apparatus described above. Tibial reresection guide 430 is similar to, but an improved version of, the tibial secondary prep guide marketed by Smith & Nephew Richards, Inc., in Memphis, Tenn. under the PROFIX® total knee system.

Like tibial resection guide 400, tibial reresection guide 430 includes a bore 432 drilled in the reresection guide at a 3° posterior tilt, i.e. tilted down from the anterior to posterior, or down from the horizontal, 3°. Tibia 2 is reresected an appropriate amount using any of the known methods.

Referring now to FIGS. 53–57, there is shown apparatus in accordance with the present invention for patellar replacement. The apparatus of the present invention allows for medialization of the patella and offers the following advantages:

containment with circumferential bone
load sharing with the "intact" patella
maintenance of the patellar ridge
"replaced" surface conforming to trochlear notch
minimal sacrifice of the patellar bone.

Figure 53:
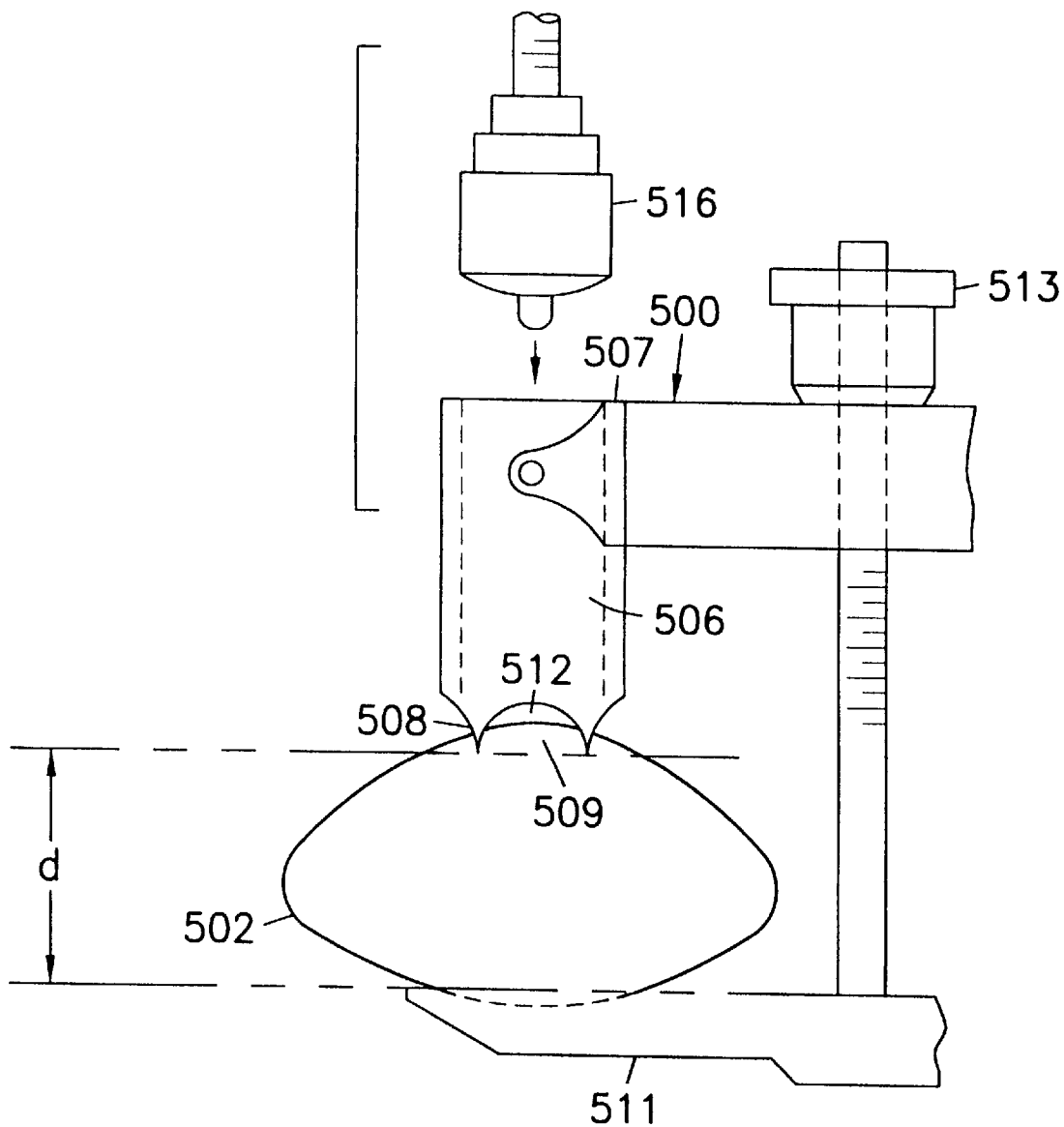
FIG. 53 is a partial side view of a patellar clamp in accordance with the present invention, fully shown in FIG. 55, measuring the thickness of a patella.

Referring now to FIG. 53, a patellar clamp 500 is shown therein. The knee must first be fully extended and 66 the patella completely exposed on the tendinous surface. The patella is then inverted and the patellar clamp 500 placed on the lateral aspect of the patella. Patellar clamp 500 is similar to, but an improved version of, the patellar clamp marketed by Smith & Nephew Richards, Inc., in Memphis, Tenn. under the PROFIX® total knee system.

Figure 57:
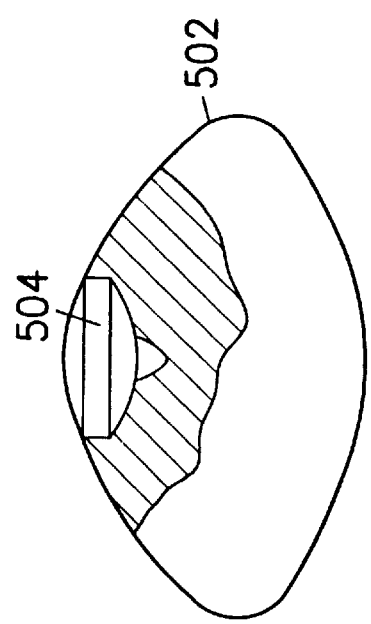
FIG. 57 is a side partially broken away view of a patella having a patella insert fitted therein.

Patellar clamp 500 is first used to measure the thickness of patella 502 so the surgeon knows how much of patella 502 will be left while accommodating the patellar insert 504, FIG. 57. It is undesirable to leave too little bone. It is desirable to have patellar insert 504 well contained and stable in the patellar bone supporting it circumferentially.

To measure the thickness of patella 502, the patellar is placed between an appropriately sized collet 506 and a base plate 511. Collet 506 has four prongs 508 equally spaced around and over the peak 509 of the patella 502. Prongs 508 are separated by an arcuate section 512. Collet 506 is then centered over the patellar ridge and patellar clamp 500 is tightened by a thumb screw 513 or by any of the known methods.

The thickness of patella 502 for purposes of the present invention is a distance d between where prongs 508 intersect the patellar, and base plate 511. As a result, patella 502 is reamed or drilled from where prongs 508 intersect patella 502.

Figure 54:
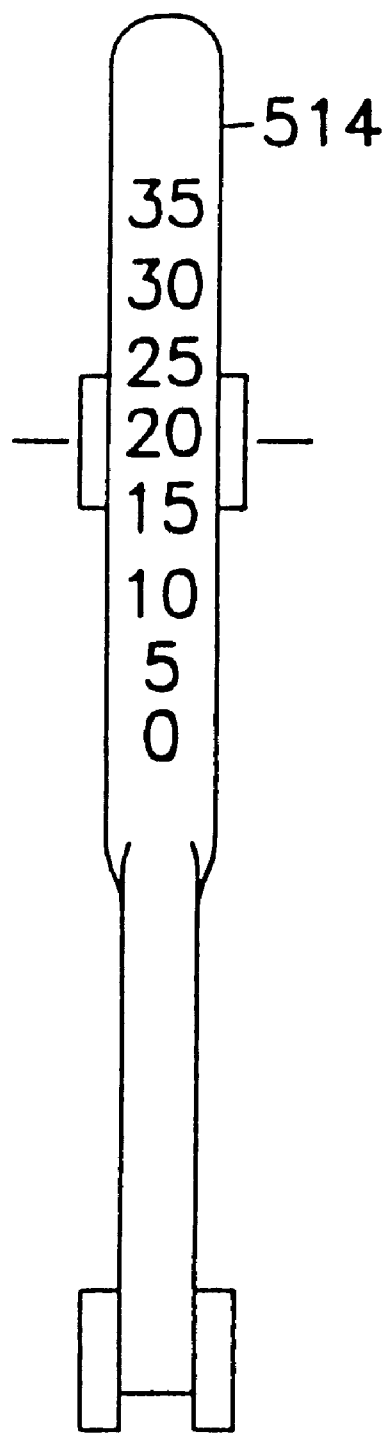
FIG. 54 is an end view of the patellar clamp of FIG. 53 showing a scale to measure the patella thickness.

Patellar clamp 500 includes a scale 514 located at an end thereof which measures distance d. The scale determines if patella 502 is thick enough for reaming. In FIG. 54, distance d is determined to be 20 mm.

Next, patellar reamer 516 corresponding in size to collet 506, is placed in patellar collet 506 to drill or ream away the required amount of patella 502 from where prongs 508 intersect patella 502 to accommodate patellar insert 504 by any of the known methods. In a preferred embodiment, patellar reamer 516 includes a depth scale 518 located therein to indicate how much patellar reamer 516 reams or drills into patella 502. Preferably, markings 518 correspond to the thickness of patellar insert 504, e.g., 8 mm or 12 mm.

Figure 55:
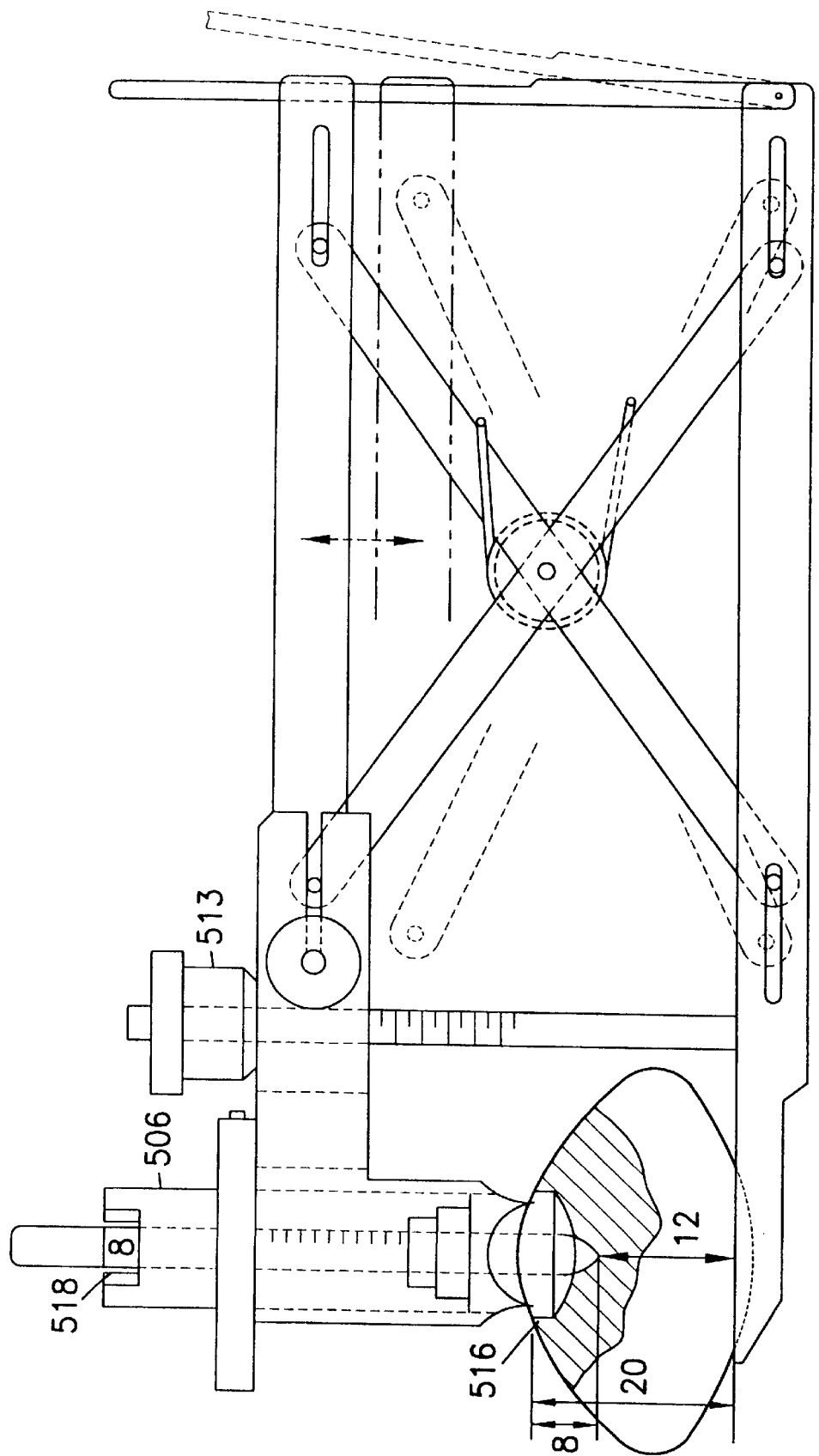
FIG. 55 is a side view of a patellar clamp in accordance with the present invention shown reaming a patella.
Figure 56:
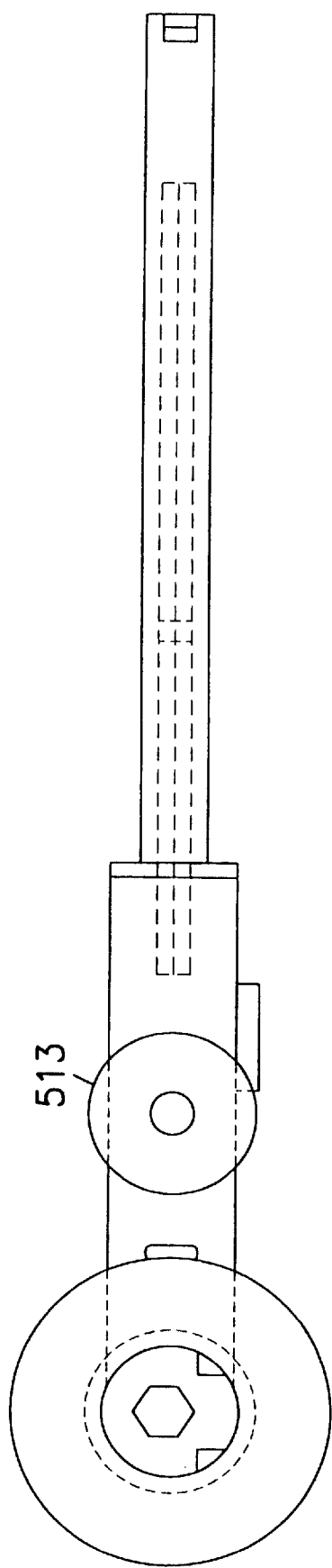
FIG. 56 is a top view of the patellar clamp of FIG. 55 reaming a patella.

By way of example, in FIGS. 55–56, scale 514 measured a patellar thickness of 20 mm. As a result, if a surgeon decides to use an 8 mm patellar insert 504, and accordingly ream patella 502 8 mm's, he then knows there will be 12 mm of bone left, which is a sufficient amount left for reaming and to accommodate patellar insert 504. As there is a significant amount of intratendonous patella distally, at least a 4–5 mm margin superiorly (if possible) should be left.

The surgeon would than ream patella 502 8 mm from where prongs 508 intersect patella 502 or until depth scale 518 indicates 8 mm. Preferably, it is recommended to rongeur the excess substance superiorly and interiorly to the level off the patella. The surgeon would then insert patellar insert 540 by any of the known methods, FIG. 57.

Figures 58, 59:
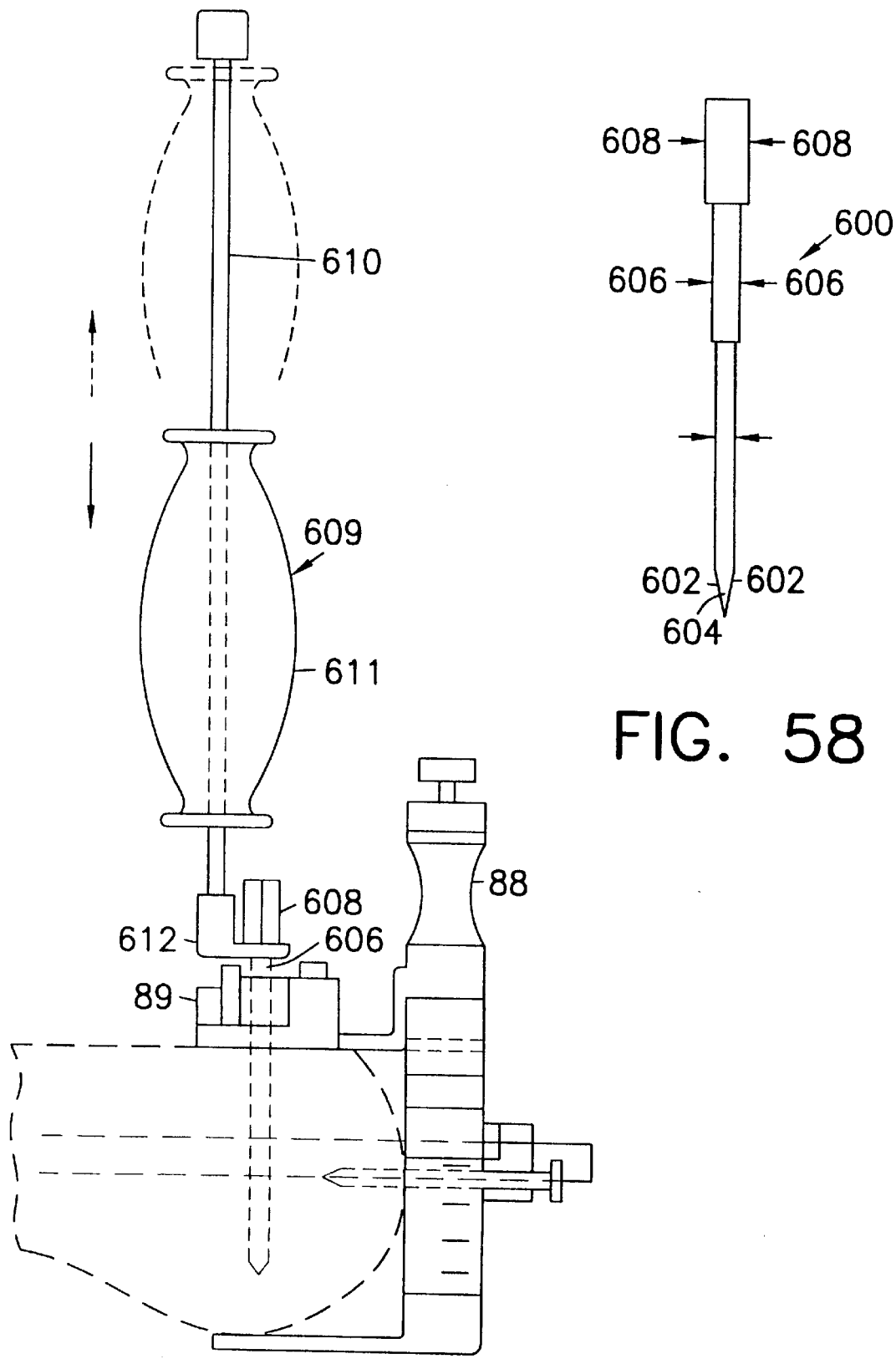
FIG. 58 is a side view of an improved nail in accordance with the present invention.
FIG. 59 is a side view of the tool of FIG. 34 mounted on a femur installed with a distal femoral cutting block and a distal femoral resection caliper of the present invention, showing the nail of FIG. 58 being removed from the femur in accordance with an improved slap hammer of the present invention.

Referring now to FIGS. 58–59, there is shown an improved nail and slap hammer apparatus of the present invention. FIG. 58 shows an improved nail 600 of the type to secure apparatus, e.g., distal femoral cutting block 89, FIG. 59, to femur 1, or tibia 2. Nail 600 includes two flat sides 602 adjacent two round sides 604. This allows nail 600 to be drilled rather than hammered into the bone. Preferably, nail 600 is lengthened ½–¾", and includes a stop 606 to prevent nail 600 from being drilled too far into the apparatus. This leaves sufficient room between the head 608 of the nail and the apparatus for a slap hammer 608 to remove nail 60 as shown in FIG. 59. Nail 600 further includes a hexagonal head 608 so the nail can be used in connection with a quick-release chuck.

Referring now to FIG. 59, slap hammer 608 includes a flat shaft 610 which creates a path of travel for a head 610 to travel up and down. Preferably, shaft 610 should be flat, and a channel in head 610 similarly shaped, to prevent head 610 from spinning on shaft 610. Preferably, slap hammer 608 should include a claw like end 612 to more easily secure nail 600 and remove it from the bone.

As mentioned above, an objective of the apparatus of the present invention is to maintain the prosthetic joint line as near anatomic as possible. For example, assuming the above prosthetic dimensions for the GENESIS II femoral prosthesis 198, 8 mm must be resected from the medial tibial condyle or 11 mm from the lateral tibial condyle. This will give a 9.5 mm resection at the midpoint at 0°. With the tibial insert of 9.5 mm replaced, the joint level will be elevated 1.5 mm medially and lowered 1.5 mm laterally, but the patellofemoral joint level will be near anatomic. It follows then that 11 mm from the medial femoral condyle and 8 mm from the lateral femoral condyle (both distally and posteriorly) must be resected to achieve the desired 19 mm bony resection to accommodate the 19 mm dimensions of the prosthetic implants.

The surgeon must decide whether to resect the thickness of the combined tibial-femoral prosthesis (i.e., 19 mm) from either the medial or lateral side of the femur 1. The most intact side, least affected or the convex side should be chosen.

When calculating the amount to be resected for the convex side, the surgeon should include an estimate of the "millimeters" of convex ligament laxity. Otherwise, a thicker than necessary tibial prosthesis may be necessary.

Normally the distal femoral resection guide i.e., the lower half 208 of tool 30D (FIG. 21) will contact the medial femoral condyle and be approximately 3 mm off the lateral femoral condyle. In this situation, 11 mm would be resected from the medial femoral condyle. If the knee is in varus and the distal femoral resection guide contacts the lateral femoral condyle, only 8 mm of bone from the lateral femoral condyle must be excised. Therefore, the medial side must be under-resected by 3 mm. Any measurements between these extremes can be easily calculated.

Resecting more than 8 mm medially or 11 mm laterally from the tibial plateau (proximal tibia) may detach or significantly weaken the posterior cruciate ligament ("PCL") insertion more than is compatible with useful function. A tibial plateau that compensates for a lost PCL may be necessary. Also, lowering the tibial resection may place the tibial prosthesis on to a less supportive cancellous surface.

It is important to achieve proper ligament balancing and not equal flexion-extension spacing. The "normal" knee is stable in full extension and has some laxity in flexion. A surgeon should allow an extra 2–3 mm of laxity in flexion to accommodate the normal laxity. If the knee has full unhindered motion, resection in flexion and extension are equal. If flexion is limited, however, an extra few mm in flexion must be resected. (See "Loss of Flexion" situation described below).

A 1 mm resection is approximately equal to 5° increased motion in both flexion and extension. Although this varies slightly from smaller patients to larger patients, the results are relatively consistent. This also implies that if the femur 1 is under-resected distally by 1 mm or over-resected posteriorly by 1 mm, 5° extra flexion should be achieved.

When checking range of motion before closing, at least 10° of laxity is required in flexion and extension. When arthroscoping a knee, initially the joint is quite snug. After "wrestling" with the knee for 5–10 minutes, the joint seems to "loosen up". This can be attributed to "stretching" the ligamentous structures around the knee. There is no normally organized elastin or reticulin in the soft tissues surrounding the knee, but these structures are capable of approximately lengthening by approximately 10% before failure (i.e., loss of elastic deformation and recovery). Generally, this is approximately 2 mm, which translates to approximately 10° of motion lost after closure.

Any varus or valgus malalignment must be compensated by removal of osteophytes and by appropriate medial or lateral ligament and soft tissue release, (i.e., concave balancing). Flexion and extension deformities are managed with a combination of bony resection, soft tissue release, and possibly posterior cruciate release.

The placement of the tibial plateau is also important. Aside from establishing proper rotation, posterior placement of the tibial plateau may be useful to:

1) compensate for shortening of the femur by allowing the tibia to move posteriorly under the femur;

2) decrease posterior impingement and roll-back;

3) decrease posteromedial tibial wear;

4) decrease posterior soft tissue impingement;

5) allow for maintenance of the posterior cruciate ligament if the femur is shortened only a few millimeters; and 6) decrease patellofemoral pressure by anteriorly placement of the tibial tubercle relative to the femur.

If the femur 1 is shortened more than approximately 4 mm from "anatomic," a surgeon should consider releasing the posterior cruciate ligament to allow the tibial prosthesis to fall back under the femoral prosthesis in flexion. In addition, releasing the posterior cruciate ligament allows increased laxity in flexion. Generally, up to 4–5 mm of extra space can be achieved in flexion and 0–2 mm in extension.

If the posterior cruciate ligament is left intact, flexion often causes posterior impingement (i.e. the "kinetic conflict"). The PCL must be released if:

1) There is significant deformity (varus, valgus, flexion, extension).

2) It has become significantly contracted.

3) There has been a patellectomy.

4) The jointline is elevated or femur shortened greater than or equal to 4 mm.

5) The patient has an inflammatory arthritis.

6) Flexion under anesthesia is less than 115°.

If the knee is unstable in flexion, consider under resection of the proximal tibia. A thicker plastic insert can also be inserted to make up for the laxity.

If the collateral ligaments are compromised, a more constrained knee may be indicated. Care must be taken not to create a patella infera. If this is of concern, then one must pre-operatively determine the proper combination of under resection of the femur and/or under resection of the tibia.

If the knee is stable in flexion or lacks full flexion, under resect the distal femur 1 mm per 5. If too tight, more can be resected after trialing. If too loose, then a slightly thicker plastic insert can be inserted with a corresponding loss of flexion.

Preferably, the instrumentation system of the present invention should correspond to the protocol described below.

The following standard protocol can be followed if a simple procedure is desired.

Standard Protocol

Resect proximal tibia. Measure from most intact or convex side (least affected)

Evaluate and "replace" for asymmetric loss of bone from the posterior condyles

Measure AP size

Resect distal femur

Downsize femur and resect condyles and chamfers

Maintain PCL

Resect posterior osteophytes

If in a knee there is 0°–15° lack of extension and 115°—full flexion, then:
1. Resect proximal tibia at standard
2. Measure AP and downsize to next smaller size
3. Resect distal femur ≦3 mm extra as needed
4. Leave PCL and resect posterior osteophytes
5. Downsize to next smaller femur
6. If tight in flexion, release PCL and ream for PCL substitution A more advanced protocol for more specific knee conditions is described below.

Advanced Protocol

"Solving" the Flexion Space

In order to get "full" (i.e., 130°) flexion, the surgeon must balance the size of the prosthesis, bony resection, soft tissue releasing, proper rotation and proper relationship to the extension space.

If we assume the parameters of PCL release=4 mm, and 5° gain motion=1 mm bone resection, then it is not difficult to produce an adequate flexion space with an "anatomic" 2–3 mm laxity.

The following situations maintain the jointline between 3 mm distally and or 4 mm proximally staring with flexion from 90°–130° and extension from 55°–0°. The above measurements and parameters will allow for a resultant range of motion of 0°–130° in most patients.

Initial Observations re: Measurement Variations

As the radius of curvature of the prosthetic condyles increase, the amount of motion gained decrease with:
 a. 1 mm bony resection
 b. PCL release
 c. Posterior capsular release PCL Resection I have found this allows 3–7 mm of flexion space laxity. This seems to be inverse relationship to the AP size of the distal femur (i.e., size 8=3 mm laxity, size 4–5=4 mm laxity, size 203=5–6 mm. I have left the calculation at 4 mm of "gained" space.

1 mm resection=5° gained motion.

I have found that 1 mm resection allows 3°–6° of increased motion. This too seems to be in inverse relationship to the AP size of the distal femur. This then is similar to the motion gained with PCL release.

Therefore, for simplicity, I allow 4 mm of gained space for PCL resection and 5°/1 mm bone resection. If tight at the end of the procedure, it is simple matter to resect an extra 1–2 mm from proximal tibia.

Flexion Contracture

I find that I underestimate a flexion contracture by about 10° consistently. Therefore, if it looks like 20°, I release and resect for 30°.

Posterior capsular release gives consistently 20° increase extension and occasionally up to 35°. The amount seems to vary inversely with the size and laxity of the patient.

For the following situations, follow the outlined procedures.

0°–15° lack of extension and 95°–105° flexion
1. Resect proximal tibia at standard
2. Measure, AP, femoral size
3. Under-resect distal femur 3 mm
4. Downsize to next smaller femur—Resect only posterior condyles now.
5. Release the PCL
6. Release posterior capsule as needed
7. Re-resect tibia ≦3 mm as needed if tight in flexion
8. Check flexion and extension spaces. Make sure the flexion space is ample and that extension is stable at 0°–10° hyperextension.
9. Resect distal femur as needed
10. Resect posterior and anterior condyle
11. Ream for PCL substitution and resect chamfer 15°–25° lack of extension and full flexion
1. Resect tibia as needed
2. Measure AP femoral size
3. Resect distal femur per standard
4. Upsize to next larger femur
5. Release PCL
6. Release posterior capsule and osteophytes
7. Measure extension space and re-resect distal femur as necessary
8. Resect anterior and posterior condyles
9. Ream for PCL substitution and resect chamfers 15°–25° lack of extension and 115°–120° flexion
1. Resect tibia as indicated
2. Measure AP femoral size
3. Resect distal femur per standard
4. Downsize to next smaller femur
5. Release PCL
6. Resect anterior and posterior condyles
7. Release posterior capsule and osteophytes
8. Measure extension space with blocks
9. Re-resect distal femur as necessary
10. Ream for PCL substitution and resect chamfers 15°–25° lack of extension and 95°–115° flexion
1. Resect tibia as indicated
2. Measure AP femoral size
3. Under-resect distal femur 3 mm
4. Downsize to next smaller femur
5. Release PCL
6. Resect posterior condyles
7. Release posterior capsule and osteophytes
8. Measure extension space with blocks
9. Re-resect proximal tibia as needed
10. Re-resect proximal distal femur as needed
11. Ream for PCL substitution and resect chamfers 25°–40° lack of extension >120° flexion
1. Resect tibia as indicated
2. Measure distal femoral AP size
3. Resect distal femur as standard
4. Upsize to next larger femur
5. Resect posterior condyles
6. Release posterior capsule PCL and osteophytes
7. Measure extension space with blocks
8. If full extension not achieved, over-resect distal femur ≦3 mm and/or proximal tibia as needed
9. Complete resection of anterior condyles
10. Ream for PCL substitution and resect chamfers 25°–40° lack of extension and 105°–115° flexion
1. Standard resection of tibia
2. Standard resection of distal femur 3. Measure AP size of femur
4. Downsize to next smaller femur
5. Resect posterior condyles
6. Release posterior capsule PCL
7. Measure extension with spacer block
8. Re-resect distal femur ≦3 mm if full extension not achieved and/or proximal tibia as needed
9. Re-resect posterior and anterior condyles, if needed
10. Ream for PCL substitution and resect chamfers 25°–40° lack of extension and 90°–105° flexion
1. Resect tibia <3 mm as needed (choose amount as needed to accommodate flexion or extension)
2. Measure AP size of femur
3. Resect distal femur as standard
4. Downsize to next smaller femur and resect posterior condyles
5. Release PCL
6. Release posterior capsule
7. Check flexion—extension space with blocks
8. Re-resect distal femur <3 mm if full extension not achieved
9. Complete resection of anterior and posterior condyles
10. Ream for PCL substitution and resect chamfers 40°–55° lack of extension and full flexion
1. Resect tibia as needed
2. Measure AP size of femur
3. Resect distal femur as standard
4. Upsize to next larger femur
5. Resect posterior condyles
6. Release posterior capsule PCL and osteophytes
7. Measure extension with spacer block
8. Resect ≦4 mm if from distal femur if needed
9. a. If full extension, resect anterior condyles and proceed
   b. If still not extending, and soft tissue has been released, re-resect proximal tibia 3≦mm. Then complete resection of anterior and posterior condyles
10. Ream for PCL substitution and resect chamfers 40°–55° lack of extension and 115°–120° flexion
1. Resect tibia as indicated
2. Measure distal femoral AP size
3. over-resect distal femur 4 mm
4. Downsize to next smaller femur
5. Resect posterior condyles
6. Release posterior capsule PCL and osteophytes
7. Measure extension with spacer block
8. If still not extending and soft tissue has been released, re-resect Proximal tibia ≦3 mm
9. Ream for PCL substitution and resect chamfers and anterior condyles 40°–55° lack of extension and 105°–115° flexion
1. Resect proximal tibia
2. Measure AP size of femur
3. Resect distal femur at standard
4. Downsize to next smaller femur
5. Resect posterior condyles
6. Resect PCL and release posterior capsule
7. Measure extension and flexion space with spacer block
8. a. Re-resect proximal tibia ≦3 mm if tight in both flexion and extension. Then re-resect distal femur ≦4 mm if still not extended.
   b. If flexion ok and lack full extension, re-resect distal femur ≦4 mm
9. Complete resection of anterior and posterior condyles
10. Ream for PCL substitution and complete chamfers 40°–55° of extension and 90°–105° flexion
1. Resect proximal tibia plus ≦3 mm extra resection as needed
2. Measure AP size of femur
3. Resect distal femur at standard minus over-resection of tibia.
4. Downsize to next smaller femur
5. Resect posterior condyles
6. Resect PCL
7. Release posterior capsule and resect osteophytes
8. Measure flexion-extension space with spacer block
9. Re-resect distal femur as necessary
10. Complete resection of anterior and posterior condyles
11. Ream for PCL substitution and complete chamfers Hyperextension Deformity 1. If the knee is unstable in flexion, consider under-resecting the proximal tibia. A thicker plastic insert can also be inserted to make up for the laxity. If the collateral ligaments are compromised, a more constrained knee may be indicated. Care must be taken not to create a patella infera. If this is of concern, then one must pre-operatively determine the proper combination of under-resection of the femur and/or under-resection of the tibia.
2. If the knee is stable in flexion or lacks full flexion, under-resect the distal femur 1 mm per 5°. If too tight, more can be resected after trialing. If too loose, then a slightly thicker plastic insert can be inserted with a corresponding loss of flexion.
3. If there is and initial hyperextension deformity, leave the knee in neutral at the end and not in 10° hyperextension.

Varus or Valgus Laxity

Pre-operative assessment of medial or lateral laxity is important. If on standing films one can ascertain excess laxity on the convex side of the knee, then appropriate compensation must be made.

1. If there is full flexion, then under-resect the distal femur 2–3 mm
2. If there is a lack of full flexion, under-resect the distal femur 2–3 mm and consider releasing the PCL If there is significant instability, consider a more constrained knee.

It should be realized that to achieve better results with total knee replacement, orthopedic surgeons must:

1) have accurate measurements;
2) have coordinated measurements;
3) maintain an "anatomic" joint line;
4) have access to dimensions of components; and
5) have the ability to compensate for deformities with a minimum of soft tissue release and bony resection.

Although the invention has been described with reference to specific embodiments thereof, it will become apparent to those skilled in the art that numerous modifications and variations can be made within the scope and spirit of the invention as defined in the attached claims.

What is claimed is:

1. An apparatus enabling the formation of planar resections on the medial and lateral condyles of a femur to provide seating surfaces to receive a femoral prosthesis, the apparatus comprising:

a measuring system for indicating a thickness of a prospective planar resection from the posterior of the medial and lateral condyles and which is initiated along a line parallel to a plane tangent to the posterior surfaces of the medial and lateral condyles, the measuring system including an anterior contacting element adapted to contact the anterior surface of the femoral cortex;

a posterior contacting element adapted to simultaneously contact the posterior surfaces of both of the medial and lateral condyles when no bone loss or equal bone loss is present from the posterior surfaces of the medial and lateral condyles; and a graduated scale between the anterior contacting element and the posterior contacting element and including graduated markings to represent a range of prosthesis sizes and to indicate a distance between the anterior surface of the femoral cortex and a plane tangent to the posterior surfaces of the medial and lateral condyles, and to indicate intermediate distances between adjacent prosthetic sizes so that a difference between a prosthetic size and the distance between the anterior surface and the tangent plane can be measured to determine the thickness of the prospective planar resection.

2. The apparatus as recited in claim 1, wherein the anterior contacting element and the posterior contacting element include respective legs slidably relative to one another.

3. The apparatus as recited in claim 1, wherein the anterior contacting element is an anterior caliper feeler.

4. The apparatus as recited in claim 1, wherein the posterior contacting element is a measurement plate.

5. The apparatus as recited in claim 4, wherein the measurement plate includes two feeler members adapted to contact corresponding posterior surfaces of the medial and lateral condyles.

6. The apparatus as recited in claim 1, further comprising a longitudinal rod adapted to be inserted into a femur, the measuring system being loosely mountable and rotatable on the rod for establishing an angle of rotation of the prospective planar resection relative to the plane tangent to the posterior surfaces of the medial and lateral condyles so as to account for unequal bone loss from the medial and lateral condyles relative to each other.

7. The apparatus as recited in claim 6, further comprising at least one clip for attachment to the medial or the lateral side of the posterior contacting element to account for unequal bone loss from posterior surfaces of the medial and lateral condyles relative to each other.

8. The apparatus as recited in claim 7, wherein the clip has a thickness approximately equal to an amount of bone loss of a posterior surface of the medial or lateral condyles.

9. The apparatus as recited in claim 7, wherein the clip has a thickness which is approximately equal to a relative bone loss between the posterior surfaces of the medial and lateral condyles.

10. The apparatus as recited in claim 7, wherein the clip is between about 2–12 mm thick.

11. The apparatus as recited in claim 7, wherein the clip is one of a series of incrementally sized clips.

12. The apparatus as recited in claim 1, further comprising a longitudinal rod adapted to be inserted into a femur, the measuring system being loosely mountable and rotatable on the rod for establishing at least one plane through which the planar resections are to be made.

13. The apparatus as recited in claim 12, further comprising a cutting guide mountable on the measuring system while the measurement system is mounted on the rod, the cutting guide for guiding a planar resection from the distal ends of the condyles.

14. The apparatus as recited in claim 13, wherein the measuring system further includes a sizer for positioning the cutting guide, the sizer including a graduated scale formed by markings corresponding to the prosthetic sizes and also indicating intermediate distances between prosthetic sizes, the markings also corresponding to the markings on the scale between the anterior caliper feeler and the measurement plate.

15. The apparatus as recited in claim 14, wherein the measuring system includes a mechanism to detach the anterior contacting element from the measuring system to thereby attach the sizer.

16. The apparatus as recited in claim 12, wherein the measuring system is adapted to contact the distal surface of the medial femoral condyle while being spaced approximately 3 mm from the distal surface of the lateral femoral condyle absent any unequal bone loss from the distal surfaces of the medial and lateral condyles relative to each other.

17. The apparatus as recited in claim 16, further comprising a lateral offset of about 3 mm thick to contact the distal surface of the lateral condyle.

18. The apparatus as recited in claim 17, wherein the measuring system includes a collet angled about 5–7° with respect to a plane which is tangent to the distal surface of the medial and lateral condyles for receiving the rod.

19. The apparatus as recited in claim 12, wherein the measuring system includes a collet angled about 8–10° with respect to a plane which is tangent to the distal surface of the medial and lateral condyles for receiving the rod.

20. The apparatus as recited in claim 1, further comprising a tool to guide an anterior resection from the medial and lateral condyles and the prospective planar resection from the posterior surface of the medial and lateral condyles, the anterior resection and the prospective planar resection being guided by the tool to be initiated along lines which are parallel to each other and to the plane tangential to the posterior surfaces such that an amount to be resected from the posterior medial condyle is substantially equal to an amount to be resected from the posterior lateral condyle when no or equal bone loss is present from the posterior medial and lateral condyles.

21. The apparatus as recited in claim 1, wherein the measuring system includes a guide slot for guiding a preliminary anterior resection along a plane flush with the anterior surface of the femoral cortex.

22. The apparatus as recited in claim 1, wherein the apparatus is designed to be used to prepare the femur to receive a femoral prosthesis having a 3° varus angulation built therein at the posterior surface of the condyles.

23. An apparatus for enabling planar resections to be made on the medial and lateral condyles of a femur of a knee joint to form seating surfaces to receive a femoral prosthesis, the apparatus comprising:

means for obtaining a measurement of the femur at the knee joint based on a plane tangent to the posterior surfaces of both the medial and lateral condyles when no bone loss or equal bone loss is present from the posterior medial and lateral condyles, and for selecting a suitable prosthesis size to be received onto the femur based on the obtained measurement; and means for measuring a difference between the selected prosthesis size and the obtained measurement so as to determine a thickness to be resected from the posterior of the medial and lateral condyles along a plane initiated along a line parallel to the tangent plane.

24. The apparatus as recited in claim 23, further comprising means for accounting for unequal bone loss from the posterior surfaces of the medial and lateral condyles relative to each other.

25. The apparatus as recited in claim 23, further comprising means for guiding a planar anterior resection from the medial and lateral condyles initiated along a line parallel to the tangent plane and the plane in which the posterior of the medial and lateral condyles are to be resected.

26. The apparatus as recited in claim 23, further comprising means for determining a plane along which the distal ends of the medial and lateral condyles are to be resected in accordance with the selected prosthesis size, and for guiding the distal planar resection.

27. A method for reconstructing a knee joint by forming planar resections on the medial and lateral condyles of a femur to form seating surfaces to receive a femoral prosthesis and to properly articulate with a tibial prothesis and a patellar prosthesis, the method comprising the steps of:

providing a measuring system including a sizing instrument having a graduated scale;

using the sizing instrument to measure for the size of the femoral prosthesis to be received by determining a first distance between an anterior surface of the femoral cortex and a plane tangent to the posterior surfaces of the medial and lateral condyles of a femur as determined when no or equal amounts of bone loss are present from the posterior surfaces;

comparing the first distance to at least two standard sizes of femoral protheses using the graduated scale on the sizing instrument;

measuring a second distance between the first distance and the size of the smaller standard femoral prosthesis when the first distance falls between two femoral prosthesis sizes; and measuring a thickness or thicknesses to be resected from the posterior surfaces of the medial and lateral condyles of the femur by adding an average thickness of the posterior condyles of the smaller standard femoral prosthesis and the second distance, such that when no bone loss or equal bone loss is present from the posterior medial and lateral condyles, the thickness to be resected from the posterior medial condyle is measured to be substantially equal to the thickness to be resected from the posterior lateral condyle and the thickness is to be resected along a plane initiated at a line parallel to the plane tangent to both the posterior medial and lateral condyles.

28. The method as recited in claim 27, further comprising the step of positioning the sizing instrument at an angle corresponding to the plane along which the posterior surfaces of the medial and lateral condyles are to be resected relative to the plane tangent to the posterior surfaces of the medial and lateral condyles so as to account for unequal bone loss from the posterior medial and the posterior lateral condyles relative to each other.

29. The method as recited in claim 27, further comprising the step of resecting from the anterior surfaces of the medial and lateral condyles along a plane substantially flush with the anterior surface of the femoral cortex and parallel to the plane tangent to the posterior medial and lateral condyles.

30. The method as recited in claim 29, further comprising the step of resecting the measured thickness or thicknesses from the posterior surfaces of the medial and lateral condyles of the femur.

31. The method as recited in claim 30, wherein the measuring system further includes a distal sizer having a graduated scale corresponding to the graduated scale on the sizing instrument, the method further comprising the steps of:

using the distal sizer having the graduated scale to measure thicknesses to be resected from the distal ends of the medial and lateral condyles, the thicknesses being determined so as to accommodate the smaller-sized standard femoral prosthesis and to produce a substantially horizontal joint line in the medial-lateral direction in extension when in an upright position; and resecting the distal ends of the medial and lateral condyles at the measured thicknesses.

32. The method as recited in claim 31, wherein the measuring system further includes a tibial measuring guide, the method further comprising the step of using the tibial measuring guide to measure a thickness to be resected from the proximal end of a tibia so that the resected tibial surface is substantially horizontal in the medial-lateral direction when in an upright position.

33. The method as recited in claim 31, wherein the measuring system further includes a tibial measuring guide, the method further comprising the steps of using the tibial measuring guide to measure a thickness to be resected from the proximal end of a tibia so that an average joint line level of the femoral and tibial prostheses is substantially at an anatomic knee level of a patient receiving the prostheses; and resecting the measured thickness from the proximal end of the tibia.

34. The method as recited in claim 33, wherein a resected space between the tibia and the femur in full extension is substantially rectangular.

35. The method as recited in claim 34, wherein a medial width of the resected space in extension substantially equals the combined thickness of a medial portion of the tibial prosthesis and the distal medial condyle of the femoral prosthesis.

36. The method as recited in claim 34, wherein a lateral width of the resected space in extension substantially equals the combined thickness of a lateral portion of the tibial prosthesis and the distal lateral condyle of the femoral prosthesis.

37. The method as recited in claim 33, wherein a medial width of the resected space in flexion between the tibia and the femur equals the combined thickness of a medial portion of the tibial prosthesis and the posterior medial condyle of the femoral prosthesis plus a width approximately corresponding to a normal medial anatomic laxity in flexion.

38. The method as recited in claim 37, wherein the width approximately corresponding to the medial laxity in flexion is about 2 mm.

39. The method as recited in claim 37, wherein a lateral width of the resected space in flexion equals the combined thickness of a lateral portion of the tibial prosthesis and the posterior lateral condyle of the femoral prosthesis plus a width approximately corresponding to a normal lateral anatomic laxity in flexion, wherein the width corresponding to the lateral laxity in flexion is equal to or greater than the width corresponding to the medial laxity in flexion.

40. The method as recited in claim 39, wherein the width corresponding to the lateral laxity is about one millimeter greater than the width corresponding to the medial laxity.

41. The method as recited in claim 33, wherein the femur and tibia are resected so as to provide greater laxity between the femoral and tibial prostheses in flexion than in extension when the resected femur and tibia are respectively fitted with the femoral and tibial protheses.

42. The method as recited in claim 33, further comprising the step of resecting at least one of the tibia and the femur to accommodate a motion range in flexion or extension.

43. The method as recited in claim 31, further comprising the step of removing osteophytes from the medial and lateral condyles.

44. The method according to claim 33, wherein the measuring system further comprises a patella reaming apparatus having a clamp and a graduated scale to measure a depth reamed from a patella, the method further comprising resecting the patella to receive the patellar prosthesis, wherein the step of resecting the patella includes the steps of:

measuring a thickness of the patella at a location to be reamed;

securing the patella in the patellar clamp;

reaming the patella to a predetermined depth to accommodate the patellar insert using the graduated scale on the patella reaming apparatus.

45. A method for reconstructing a knee joint by forming planar resections on the medial and lateral condyles of a femur to form seating surfaces to receive a femoral prosthesis with a built-in varus angulation and to properly articulate with a tibial prosthesis and a patellar prosthesis, the method comprising:

providing a measuring system including a sizing instrument having a graduated scale;

using the sizing instrument to measure for the size of the femoral prosthesis to be received by determining a first distance between an anterior surface of the femoral cortex and a plane tangent to the posterior surfaces of the medial and lateral condyles of a femur as determined when no or equal amounts of bone loss are present from the posterior surfaces;

comparing the first distance to at least two standard sizes of femoral prostheses using the graduated scale on the sizing instrument;

choosing the femoral prosthesis having the larger standard size when the first distance falls between two femoral prosthesis sizes;

measuring a second distance between the first distance and the size of the larger femoral prosthesis;

measuring a thickness to be resected from the posterior surfaces of the medial and lateral condyles of the femur by subtracting the second distance from an average thickness of the posterior condyles of the larger femoral prosthesis, such that when no bone loss or equal bone loss is present from the posterior medial and lateral condyles, the thickness to be resected from the posterior medial condyle is measured to be substantially equal to the thickness to be resected from the posterior lateral condyle, and the thickness is to be resected along a plane initiated at a line parallel to the plane tangent to both the posterior medial and lateral condyles.

46. The method as recited in claim 45, further comprising the step of resecting from the anterior surfaces of the medial and lateral condyles along a plane substantially flush with the anterior surface of the femoral cortex and parallel to the plane tangent to the posterior medial and lateral condyles.

47. The method as recited in claim 46, further comprising the step of resecting the measured thickness from the posterior surfaces of the medial and lateral condyles.

48. The method as recited in claim 47, wherein the measuring system further includes a distal sizer having a graduated scale corresponding to the graduated scale on the sizing instrument, the method further comprising the steps of:

using the distal sizer having the graduated scale to measure thicknesses to be resected from the distal ends of the medial and lateral condyles, the thicknesses being determined so as to accommodate the larger-sized standard femoral prosthesis and to produce a substantially horizontal joint line in the medial-lateral direction in extension when in an upright position; and resecting the distal ends of the medial and lateral condyles at the measured thicknesses.

49. The method as recited in claim 48, wherein the measuring system further includes a tibial measuring guide, the method further comprising the steps of using the tibial measuring guide to measure a thickness to be resected from the proximal end of a tibia so that an average joint line level of the femoral and tibial prostheses is substantially at an anatomic knee level of a patient receiving the prostheses; and resecting the measured thickness from the proximal end of the tibia.

50. A method for reconstructing a knee joint by forming planar resections on the medial and lateral condyles of a femur of a knee to form seating surfaces to receive a femoral prosthesis and to properly articulate with a tibial prosthesis and a patellar prosthesis, the method comprising the steps of:

measuring a thickness to be resected by a prospective planar resection to be made from the posterior surfaces of the medial and lateral condyles of a femur at which a distance between an anterior surface of the femoral cortex and the prospective planar resection is substantially equal to an interior dimension of a femoral prosthesis to be fitted on the femur, the prospective planar resection producing resection of the medial and lateral condyles from the posterior surfaces of respective thicknesses which are substantially equal and which is initiated along a line parallel to a plane tangent to the posterior surfaces of the medial and lateral condyles when no bone loss or equal bone loss is present from the posterior surfaces of the medial and lateral condyles;

resecting from the anterior surfaces of the medial and lateral condyles along a plane substantially flush with the anterior surface of the femoral cortex and parallel to the prospective planar resection, and then resecting along the prospective planar resection; and resecting a distal end of the medial and lateral condyles along a plane which produces respective resected thicknesses at the medial and lateral condyles so that a distal femoral surface resulting from the distal resection is substantially level or horizontal in extension.

51. The method as recited in claim 50, further comprising the steps of measuring a thickness or level of a proximal tibial resection such that an average joint line height of the fitted femoral prosthesis is at or near an anatomic knee height of a patient being fitted with the femoral prosthesis; and resecting the proximal end of the tibia at the measured thickness.

52. The method as recited in claim 51, wherein a resected space between the proximal tibial surface and the femur of the knee in full extension is substantially rectangular.

53. A method for reconstructing a knee joint by forming planar resections on the anterior, posterior, and distal surfaces of the medial and lateral condyles of a femur to form seating surfaces to receive a femoral prosthesis and to properly articulate with a tibial prosthesis and a patellar prosthesis, the method comprising:

providing a measuring system including
an anterior contacting element adapted to contact the anterior surface of the femoral cortex,
a posterior contacting element adapted to simultaneously contact the posterior surfaces of both of the medial and lateral condyles when no bone loss or equal bone loss is present from the posterior surfaces of the medial and lateral condyles,
a graduated scale between the anterior contacting element and the posterior contacting element,
a distal sizer having a graduated scale with graduated markings corresponding to the graduated scale between the anterior contacting element and the posterior contacting element, and
a tibial measuring guide;

measuring for the size of the femoral prosthesis to be received by contacting the anterior contacting element to the anterior surface of the femoral cortex and by placing the posterior contacting element along a plane tangent to the posterior surfaces of the medial and lateral condyles element to determine a first distance between therebetween, the tangent plane being determined according to a condition when no or equal amounts of bone loss are present from the posterior surfaces;

using the graduated scale between the anterior contacting element and the posterior contacting element to compare the first distance to at least two standard femoral prosthesis sizes;

measuring a second distance between the first distance and the size of the smaller standard femoral prosthesis using the graduated size scale between the anterior contacting element and the posterior contacting element when the measured size falls between the at least two standard femoral prosthesis sizes;

determining a thickness to be resected at the posterior surface of the medial and lateral condyles of the femur by adding the thickness of the smaller femoral prosthesis and the second distance, such that the respective thicknesses to be resected from the posterior surface of the medial condyle and from the posterior surface of the lateral condyle are substantially equal to each other and is initiated along a line parallel to the plane tangent to the posterior surfaces of the medial and lateral condyles when no bone loss or equal bone loss is present from the posterior surfaces of the condyles;

resecting the medial and lateral condyles along a plane at the anterior surfaces thereof substantially flush with the anterior surface of the femoral cortex and parallel to the prospective planar resection, and then along the determined parallel plane at the posterior surfaces of the medial and lateral condyles;

measuring thicknesses to be resected from the distal ends of the medial and lateral condyles using the graduated scale on the distal sizer, the thicknesses of the distal resections being determined so as to accommodate the smaller-sized standard femoral prosthesis and so that a distal femoral surface resulting from said distal resection is substantially level or horizontal in extension;

resecting the distal ends of the medial and lateral condyles along the measured thicknesses;

using the tibial measuring guide to measure a thickness of a proximal tibial planar resection so as to place the average level of the joint line of the femoral prosthesis substantially at anatomic level; and resecting along the measured proximal tibial resection.

54. The method as recited in claim 53, wherein the angle of the planar resection at the distal surface of the medial and lateral condyles corresponds to the medial-lateral plane of the tibial resection.

55. The method according to claim 53, further comprising checking the space between the resected tibial and femoral surfaces in both flexion and extension to ensure proper ligament balance medially and laterally, such that the balance is solid in extension and slightly loose in flexion.

* * * * *

UNITED STATES PATENT AND TRADEMARK OFFICE
CERTIFICATE OF CORRECTION

PATENT NO.    : 6,024,746  
DATED         : February 15, 2000  
INVENTOR(S)   : Lawrence Katz Page 1 of 1

Figure 4A:
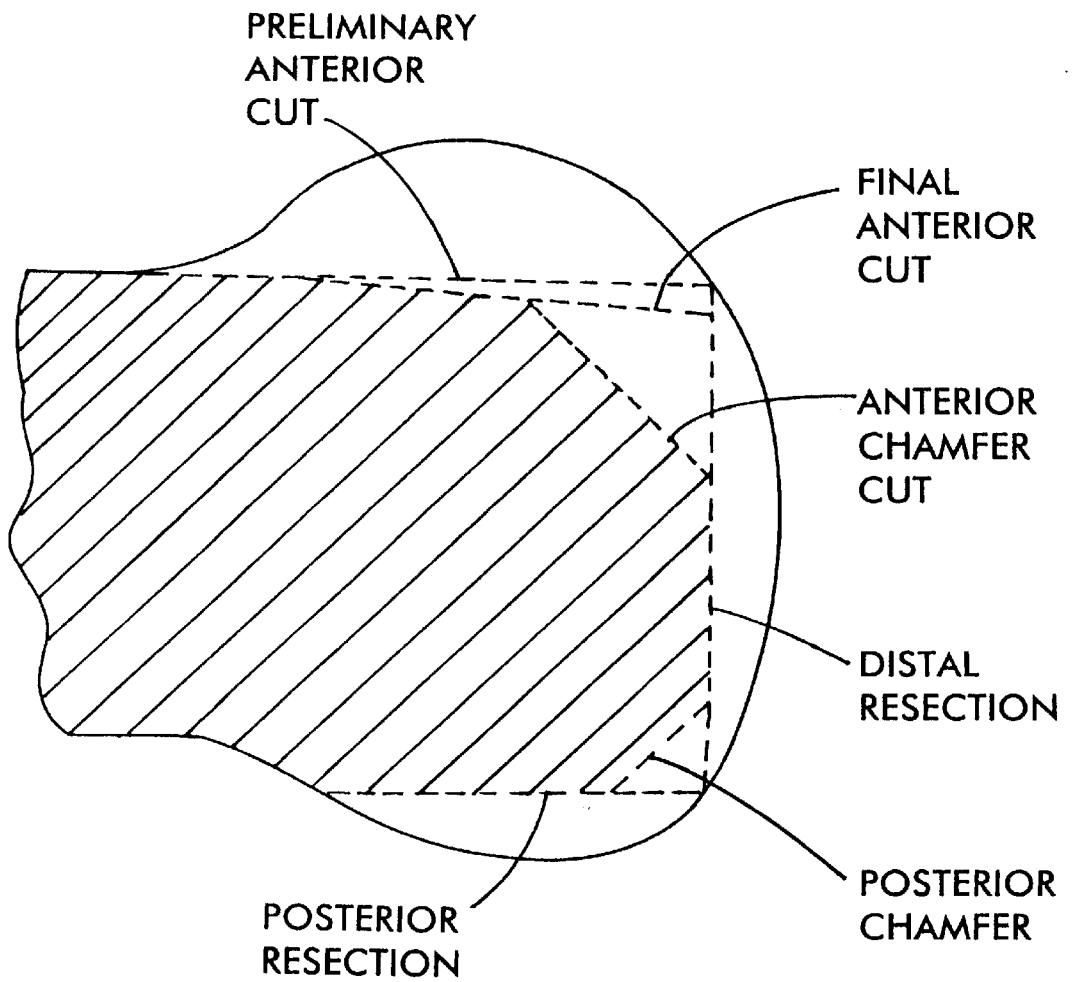
Figure 6:
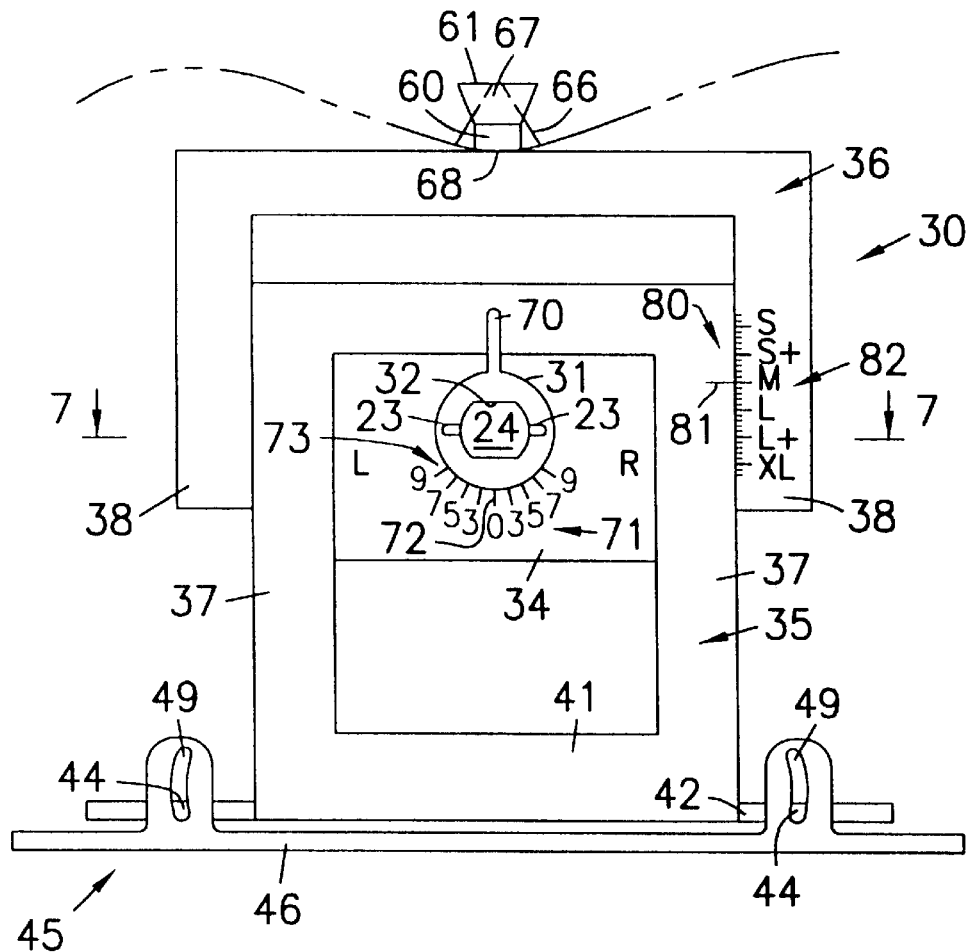
FIG. 6 is an end view of the tool taken in the direction of arrow 6—6 in FIG. 5.

It is certified that error appears in the above-identified patent and that said Letters Patent is hereby corrected as shown below:

Specifications:

Column 5,
Between lines 30 and 31, insert the following: -- Fig. 4a is a side view identifying each of the cuts made to the femur. --;

Column 20,
Line 6, change "respectively," to -- as illustrated in Figs.1 and 4a, --;

Column 21,
Line 21, after "105", insert -- (see Fig. 4a) --.

Amend claims 13 and 32 as follows:
Claim 13,
Line 3, (Column 32, line 6). Change "measurement" to -- measuring --;

Claim 32,
Line 7 (column 34, line 27), after "when", insert -- the tibia is -- .

Signed and Sealed this

Eleventh Day of September, 2001

Attest:

NICHOLAS P. GODICI  
Attesting Officer   Acting Director of the United States Patent and Trademark Office